United States Patent
Brams et al.

(10) Patent No.: US 6,413,771 B1
(45) Date of Patent: *Jul. 2, 2002

(54) NEUTRALIZING HIGH AFFINITY HUMAN MONOCLONAL ANTIBODIES SPECIFIC TO RSV F-PROTEIN AND METHODS FOR THEIR MANUFACTURE AND THERAPEUTIC USE THEREOF

(75) Inventors: Peter Brams, San Diego; Phillip R. Morrow, Carlsbad, both of CA (US)

(73) Assignee: IDEC Pharmaceuticals Corporation, San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 35 days.

This patent is subject to a terminal disclaimer.

(21) Appl. No.: 09/335,697

(22) Filed: Jun. 18, 1999

Related U.S. Application Data

(60) Continuation of application No. 08/770,057, filed on Dec. 19, 1996, now Pat. No. 5,958,765, which is a division of application No. 08/488,376, filed on Jun. 7, 1995, now Pat. No. 5,811,524.

(51) Int. Cl.[7] .............................. C12N 5/06; C12Q 1/70; G01N 33/53; C12P 21/08; A61K 39/42

(52) U.S. Cl. .......................... 435/339; 435/5; 435/7.1; 530/388.3; 424/147.1; 424/159.1; 424/192.1; 424/211.1

(58) Field of Search .................... 530/388.3; 424/147.1, 424/159.1, 192.1, 211.1; 435/5, 7.1, 339

(56) References Cited

U.S. PATENT DOCUMENTS

| | | | |
|---|---|---|---|
| 5,411,749 A | 5/1995 | Mayo et al. | 424/578 |
| 5,476,997 A | 12/1995 | Kaneshima et al. | 800/2 |

FOREIGN PATENT DOCUMENTS

| | | |
|---|---|---|
| WO | WO 93/05796 | 4/1993 |
| WO | WO 93/19197 | 9/1993 |

OTHER PUBLICATIONS

Uchibayashi, N. et al., *Hybridoma*, 14:313–321 (1995).
Carlsson, R. et al., *J. Immunol.*, 148:1065–1071 (1992).
Satoh, N. et al., *Immunol. Lett.*, 47:113–119 (1995).
Kudo, T. et al., *Tohoku J. Exp. Med.*, 168:323–327 (1992).
Kudo, T. et al., *Tohoku J. Exp. Med.*, 171:327–338 (1993).
Ifversen, P. & Borrebaeck, C.A.K., *Seminars in Immunol.*, 8:243–248 (1996).
Ware, C.F. et al., *J. Immunol. Meth.*, 85:353–361 (1995).

*Primary Examiner*—Hankyel T. Park
(74) *Attorney, Agent, or Firm*—Robin L. Teskin

(57) ABSTRACT

A highly efficient method for generating human antibodies in particular which are specific to be RSV fusion protein which combines in vitro priming of human spleen cells and antigen boosting in SCID mice is taught. This method provides for very high human antibody titers which are predominantly of the IgG isotype which contain antibodies of high specificity and affinity to desired antigens. This method is well suited for generating human monoclonal antibodies for therapeutic and diagnostic applications as well as for rescue of human cells for generation of combinational human antibody gene libraries. Two human monoclonal antibodies, RF-1 and RF-2 which each possess an affinity for RSV F-protein $\leq 2\times10^{-9}$ Molar are taught as well as their corresponding amino acid and DNA sequences. These antibodies are to be used therapeutically and prophylactically for treating or preventing RSV infection, as well as for diagnosis of RSV in analytes.

7 Claims, 17 Drawing Sheets

FIG. 7a

```
Frame 1  D   I   Q   M   T   Q   S   P   S   S   L   S   A   S   V   G   D   R   V   T
         GAC ATC CAG ATG ACC CAG TCT CCA TCC TCC CTG TCT GCA TCT GTC GGA GAC AGA GTC ACC
         9                   18                  27                  36                  45                  54

I   T   C   R   A   G   Q   R   I   A   S   Y   L   N   W   Y   Q   H   K   P   G   K
         ATC ACT TGC CGG GCA GGT CAG AGG ATT GCT AGT TAT TTA AAT TGG TAT CAG CAC AAA CCA GGG AAA
                          69                  78                  87                  96                  105                 114                 123

A   P   K   L   L   I   Y   A   G   S   N   L   H   R   G   V   P   S   R   F   S   G
         GCC CCT AAG CTC CTG ATA TAT GCT GGA TCC AAT TTG CAC CGT GGG GTC CCG TCA AGG TTC AGT GGC
                          135                 144                 153                 162                 171                 180                 189

G   G   S   G   T   D   F   T   L   T   I   N   S   L   Q   P   E   D   F   A   T   Y
         GGT GGA TCT GGG ACA GAT TTC ACT CTC ACC ATC AAC AGT CTG CAA CCT GAA GAT TTT GCA ACT TAC
                          201                 210                 219                 228                 237                 246                 255

Y   C   Q   Q   A   Y   S   T   P   W   T   F   G   P   G   T   K   V   E   I   K
         TAT TGT CAA CAG GCT TAC AGT ACC CCC TGG ACT TTC GGC CCA GGG ACC AAG GTG GAA ATC AAA
                          267                 276                 285                 294                 303                 312                 321
```

FIG. 7b

```
Frame 1  Q   V   Q   L   Q   E   S   G   P   A   L   V   K   P   T   Q   T   L   T   L
         CAG GTA CAG TTG CAG GAG TCT GGT CCT GCG CTG GTA AAA CCC ACA CAG ACC CTC ACA CTG
         9                   18                  27                  36                  45                  54

T   C   T   F   S   G   F   S   L   S   T   R   G   M   S   V   N   W   I   R   Q   P
         ACC TGC ACC TTC TCT GGG TTC TCA CTC AGC ACC AGA GGA ATG AGT GTG AAC TGG ATC CGT CAG CCC
         69                  78                  87                  96                  105                 114                 123

P   G   K   A   L   E   W   L   A   R   I   D   W   D   D   D   T   F   Y   S   A   S
         CCA GGG AAG GCC CTG GAA TGG CTA GCC CGC ATT GAT TGG GAC GAT GAT ACA TTC TAC AGC GCT TCT
         135                 144                 153                 162                 171                 180                 189

L   K   T   R   L   S   I   S   K   D   T   S   K   N   Q   V   V   L   R   M   T   N
         CTG AAG ACT AGG CTC AGC ATC TCC AAG GAC ACC TCC AAA AAC CAG GTG GTC CTC AGA ATG ACC AAC
         201                 210                 219                 228                 237                 246                 255

V   D   P   V   D   T   A   T   Y   F   C   A   R   A   S   L   Y   D   S   D   S   F
         GTA GAC CCT GTG GAC ACA GCC ACA TAT TTT TGT GCA CGG GCC TCA CTA TAT GAC AGT GAT AGT TTC
         267                 276                 285                 294                 303                 312                 321

Y   L   F   Y   H   A   Y   W   G   Q   G   T   V   V   T   V   S   S
         TAC CTC TTC TAC CAT GCC TAC TGG GGC CAG GGA ACC GTG GTC ACC GTC TCC TCA
         333                 342                 351                 360                 369                 378
```

FIG. 8a

```
Frame 1  D   I   Q   M   T   Q   S   P   S   S   L   S   A   S   V   G   D   R   V   T
         GAC ATC CAG ATG ACC CAG TCT CCA TCC TCC CTG TCT GCA TCT GTC GGA GAC AGA GTC ACC
                         9                  18                  27                  36                  45                  54

I   T   C   R   A   S   Q   S   I   A   S   Y   V   N   W   Y   Q   Q   K   P   G   K
         ATC ACT TGC CGG GCA AGT CAG AGC ATT GCC AGT TAT GTA AAT TGG TAT CAA CAG AAA CCA GGG AAA
                         69                  78                  87                  96                  105                 114                 123

A   P   K   V   L   I   F   A   S   A   N   L   V   S   G   V   P   S   R   F   S   G
         GCC CCT AAA GTC CTC ATT TTT GCT TCA GCC AAT TTG GTG AGT GGG GTC CCA TCA AGA TTC AGT GGC
                         135                 144                 153                 162                 171                 180                 189

S   G   S   G   T   V   F   T   L   T   I   S   N   L   Q   P   E   D   F   A   T   Y
         AGT GGA TCT GGG ACA GTT TTC ACC CTC ACC ATC AGC AAT CTG CAA CCT GAA GAT TTT GCA ACC TAC
                         201                 210                 219                 228                 237                 246                 255

F   C   Q   Q   S   Y   T   N   F   S   F   G   Q   G   T   K   L   E   I   K
         TTC TGT CAG CAG AGT TAC ACT AAT TTC AGT TTT GGC CAG GGG ACC AAG CTG GAA ATC AAA
                         267                 276                 285                 294                 303                 312
```

FIG. 8b

```
Frame 1  Q   V   Q   L   Q   E   S   G   P   V   V   V   K   P   T   E   T   L   T   L
         CAG GTG CAG TTG CAG GAG TCT GGT CCT GTG GTG GTG AAA CCC ACA GAG ACC CTC ACG CTG
             9               18              27              36              45              54

T   C   T   V   S   G   F   S   L   S   N   P   R   M   G   V   T   W   I   R   Q   P
         ACC TGC ACC GTC TCT GGG TTC TCA CTC AGC AAC CCT AGA ATG GGT GTG ACC TGG ATC CGT CAG CCC
                     69              78              87              96              105             114             123

P   G   K   A   L   E   W   L   G   N   I   F   S   S   D   E   K   S   F   S   P   S
         CCC GGG AAG GCC CTA GAA TGG CTT GGA AAC ATT TTT TCG AGT GAC GAG AAG TCC TTC AGT CCT TCT
                     135             144             153             162             171             180             189

L   K   S   R   L   T   T   S   Q   D   T   S   R   S   Q   V   V   L   S   L   T   N
         CTG AAG AGC AGA CTC ACC ACC TCC CAG GAC ACC TCC AGA AGC CAG GTG GTC CTA AGC TTG ACC AAC
                     201             210             219             228             237             246             255

V   D   P   V   D   T   A   T   Y   Y   C   A   R   V   G   L   Y   D   I   N   A   Y
         GTG GAC CCT GTG GAC ACA GCC ACA TAT TAC TGT GCA CGG GTA GGA CTG TAT GAC ATC AAT GCT TAT
                     267             276             285             294             303             312             321

Y   L   Y   Y   L   D   Y   W   G   Q   G   T   L   V   T   V   S   S
         TAC CTA TAC TAC CTG GAT TAT TGG GGG CAG GGA ACC CTG GTC ACC GTC TCC TCA
                     333             342             351             360             369             378
```

```
ATG GAG ACC CCT GCT CAG CTC CTG GGG CTC CTG CTA CTC TGG CTC CGA     48
Met Glu Thr Pro Ala Gln Leu Leu Gly Leu Leu Leu Leu Trp Leu Arg
 1               5                  10                  15

GGT GCC AGA TGT GAC ATC CAG ATG ACC CAG TCT CCA TCC TCC CTG TCT     96
Gly Ala Arg Cys Asp Ile Gln Met Thr Gln Ser Pro Ser Ser Leu Ser
            20                  25                  30

GCA TCT GTC GGA GAC AGA GTC ACC ATC ACT TGC CGG GCA GGT CAG AGG    144
Ala Ser Val Gly Asp Arg Val Thr Ile Thr Cys Arg Ala Gly Gln Arg
        35                  40                  45

ATT GCT AGT TAT TTA AAT TGG TAT CAG CAC AAA CCA GGG AAA GCC CCT    192
Ile Ala Ser Tyr Leu Asn Trp Tyr Gln His Lys Pro Gly Lys Ala Pro
    50                  55                  60

AAG CTC CTG ATA TAT GCT GGA TCC AAT TTG CAC CGT GGG GTC CCG TCA    240
Lys Leu Leu Ile Tyr Ala Gly Ser Asn Leu His Arg Gly Val Pro Ser
65                  70                  75                  80

AGG TTC AGT GGC GGT GGA TCT GGG ACA GAT TTC ACT CTC ACC ATC AAC    288
Arg Phe Ser Gly Gly Gly Ser Gly Thr Asp Phe Thr Leu Thr Ile Asn
                85                  90                  95

AGT CTG CAA CCT GAA GAT TTT GCA ACT TAC TAT TGT CAA CAG GCT TAC    336
Ser Leu Gln Pro Glu Asp Phe Ala Thr Tyr Tyr Cys Gln Gln Ala Tyr
            100                 105                 110

AGT ACC CCC TGG ACT TTC GGC CCA GGG ACC AAG GTG GAA ATC AAA CGT    384
Ser Thr Pro Trp Thr Phe Gly Pro Gly Thr Lys Val Glu Ile Lys Arg
        115                 120                 125

ACG GTG GCT GCA CCA TCT GTC TTC ATC TTC CCG CCA TCT GAT GAG CAG    432
Thr Val Ala Ala Pro Ser Val Phe Ile Phe Pro Pro Ser Asp Glu Gln
    130                 135                 140

TTG AAA TCT GGA ACT GCC TCT GTT GTG TGC CTG CTG AAT AAC TTC TAT    480
Leu Lys Ser Gly Thr Ala Ser Val Val Cys Leu Leu Asn Asn Phe Tyr
145                 150                 155                 160

CCC AGA GAG GCC AAA GTA CAG TGG AAG GTG GAT AAC GCC CTC CAA TCG    528
Pro Arg Glu Ala Lys Val Gln Trp Lys Val Asp Asn Ala Leu Gln Ser
                165                 170                 175

GGT AAC TCC CAG GAG AGT GTC ACA GAG CAG GAC AGC AAG GAC AGC ACC    576
Gly Asn Ser Gln Glu Ser Val Thr Glu Gln Asp Ser Lys Asp Ser Thr
            180                 185                 190

TAC AGC CTC AGC AGC ACC CTG ACG CTG AGC AAA GCA GAC TAC GAG AAA    624
Tyr Ser Leu Ser Ser Thr Leu Thr Leu Ser Lys Ala Asp Tyr Glu Lys
        195                 200                 205

CAC AAA GTC TAC GCC TGC GAA GTC ACC CAT CAG GGC CTG AGC TCG CCC    672
His Lys Val Tyr Ala Cys Glu Val Thr His Gln Gly Leu Ser Ser Pro
    210                 215                 220

GTC ACA AAG AGC TTC AAC AGG GGA GAG TGT TGA                        705
Val Thr Lys Ser Phe Asn Arg Gly Glu Cys *
225                 230                 235
```

FIG. 9a

```
ATG GGT TGG AGC CTC ATC TTG CTC TTC CTT GTC GCT GTT GCT ACG CGT      48
Met Gly Trp Ser Leu Ile Leu Leu Phe Leu Val Ala Val Ala Thr Arg
            240                 245                 250

GTC CTG TCC CAG GTG CAG TTG CAG GAG TCT GGT CCT GTG GTG GTG AAA      96
Val Leu Ser Gln Val Gln Leu Gln Glu Ser Gly Pro Val Val Val Lys
            255                 260                 265

CCC ACA GAG ACC CTC ACG CTG ACC TGC ACC GTC TCT GGG TTC TCA CTC     144
Pro Thr Glu Thr Leu Thr Leu Thr Cys Thr Val Ser Gly Phe Ser Leu
            270                 275                 280

AGC AAC CCT AGA ATG GGT GTG ACC TGG ATC CGT CAG CCC CCG GGG AAG     192
Ser Asn Pro Arg Met Gly Val Thr Trp Ile Arg Gln Pro Pro Gly Lys
            285                 290                 295

GCC CTA GAA TGG CTT GGA AAC ATT TTT TCG AGT GAC GAG AAG TCC TTC     240
Ala Leu Glu Trp Leu Gly Asn Ile Phe Ser Ser Asp Glu Lys Ser Phe
300             305                 310                 315

AGT CCT TCT CTG AAG AGC AGA CTC ACC ACC TCC CAG GAC ACC TCC AGA     288
Ser Pro Ser Leu Lys Ser Arg Leu Thr Thr Ser Gln Asp Thr Ser Arg
            320                 325                 330

AGC CAG GTG GTC CTA AGC TTG ACC AAC GTG GAC CCT GTG GAC ACA GCC     336
Ser Gln Val Val Leu Ser Leu Thr Asn Val Asp Pro Val Asp Thr Ala
            335                 340                 345

ACA TAT TAC TGT GCA CGG GTA GGA CTG TAT GAC ATC AAT GCT TAT TAC     384
Thr Tyr Tyr Cys Ala Arg Val Gly Leu Tyr Asp Ile Asn Ala Tyr Tyr
            350                 355                 360

CTA TAC TAC CTG GAT TAT TGG GGG CAG GGA ACC CTG GTC ACC GTC TCC     432
Leu Tyr Tyr Leu Asp Tyr Trp Gly Gln Gly Thr Leu Val Thr Val Ser
365             370                 375

TCA GCT AGC ACC AAG GGC CCA TCG GTC TTC CCC CTG GCA CCC TCC TCC     480
Ser Ala Ser Thr Lys Gly Pro Ser Val Phe Pro Leu Ala Pro Ser Ser
380             385                 390                 395

AAG AGC ACC TCT GGG GGC ACA GCG GCC CTG GGC TGC CTG GTC AAG GAC     528
Lys Ser Thr Ser Gly Gly Thr Ala Ala Leu Gly Cys Leu Val Lys Asp
            400                 405                 410

TAC TTC CCC GAA CCG GTG ACG GTG TCG TGG AAC TCA GGC GCC CTG ACC     576
Tyr Phe Pro Glu Pro Val Thr Val Ser Trp Asn Ser Gly Ala Leu Thr
            415                 420                 425

AGC GGC GTG CAC ACC TTC CCG GCT GTC CTA CAG TCC TCA GGA CTC TAC     624
Ser Gly Val His Thr Phe Pro Ala Val Leu Gln Ser Ser Gly Leu Tyr
            430                 435                 440

TCC CTC AGC AGC GTG GTG ACC GTG CCC TCC AGC AGC TTG GGC ACC CAG     672
Ser Leu Ser Ser Val Val Thr Val Pro Ser Ser Ser Leu Gly Thr Gln
            445                 450                 455

ACC TAC ATC TGC AAC GTG AAT CAC AAG CCC AGC AAC ACC AAG GTG GAC     720
Thr Tyr Ile Cys Asn Val Asn His Lys Pro Ser Asn Thr Lys Val Asp
460             465                 470                 475

AAG AAA GCA GAG CCC AAA TCT TGT GAC AAA                             750
Lys Lys Ala Glu Pro Lys Ser Cys Asp Lys
            480                 485
```

Thr His Thr Cys Pro Pro Cys Pro Ala Pro Glu Leu Leu Gly Gly Pro Ser Val Phe Leu Phe
ACT CAC ACA TGC CCA CCG TGC CCA GCA CCT GAA CTC CTG GGG GGA CCG TCA GTC TTC CTC TTC
        759         768         777        786        795        804        813

Pro Pro Lys Pro Lys Asp Thr Leu Met Ile Ser Arg Thr Pro Glu Val Thr Cys Val Val Val
CCC CCA AAA CCC AAG GAC ACC CTC ATG ATC TCC CGG ACC CCT GAG GTC ACA TGC GTG GTG GTG
        822         831         840        849        858        867        876

Asp Val Ser His Glu Asp Pro Glu Val Lys Phe Asn Trp Tyr Val Asp Gly Val Glu Val His
GAC GTG AGC CAC GAA GAC CCT GAG GTC AAG TTC AAC TGG TAC GTG GAC GGC GTG GAG GTG CAT
        885         894         903        912        921        930        939

Asn Ala Lys Thr Lys Pro Arg Glu Glu Gln Tyr Asn Ser Thr Tyr Arg Val Val Ser Val Leu
AAT GCC AAG ACA AAG CCG CGG GAG GAG CAG TAC AAC AGC ACG TAC CGT GTG GTC AGC GTC CTC
        948         957         966        975        984        993        1002

Thr Val Leu His Gln Asp Trp Leu Asn Gly Lys Glu Tyr Lys Cys Lys Val Ser Asn Lys Ala
ACC GTC CTG CAC CAG GAC TGG CTG AAT GGC AAG GAG TAC AAG TGC AAG GTC TCC AAC AAA GCC
        1011        1020        1029       1038       1047       1056       1065

Leu Pro Ala Pro Ile Glu Lys Thr Ile Ser Lys Ala Lys Gly Gln Pro Arg Glu Pro Gln Val
CTC CCA GCC CCC ATC GAG AAA ACC ATC TCC AAA GCC AAA GGG CAG CCC CGA GAA CCA CAG GTG
        1074        1083        1092       1101       1110       1119       1128

Tyr Thr Leu Pro Pro Ser Arg Asp Glu Leu Thr Lys Asn Gln Val Ser Leu Thr Cys Leu Val
TAC ACC CTG CCC CCA TCC CGG GAT GAG CTG ACC AAG AAC CAG GTC AGC CTG ACC TGC CTG GTC
        1137        1146        1155       1164       1173       1182       1191

Lys Gly Phe Tyr Pro Ser Asp Ile Ala Val Glu Trp Glu Ser Asn Gly Gln Pro Glu Asn Asn
AAA GGC TTC TAT CCC AGC GAC ATC GCC GTG GAG TGG GAG AGC AAT GGG CAG CCG GAG AAC AAC
        1200        1209        1218       1227       1236       1245       1254

Tyr Lys Thr Thr Pro Pro Val Leu Asp Ser Asp Gly Ser Phe Phe Leu Tyr Ser Lys Leu Thr
TAC AAG ACC ACG CCT CCC GTG CTG GAC TCC GAC GGC TCC TTC TTC CTC TAC AGC AAG CTC ACC
        1263        1272        1281       1290       1299       1308       1317

Val Asp Lys Ser Arg Trp Gln Gln Gly Asn Val Phe Ser Cys Ser Val Met His Glu Ala Leu
GTG GAC AAG AGC AGG TGG CAG CAG GGG AAC GTC TTC TCA TGC TCC GTG ATG CAT GAG GCT CTG
        1326        1335        1344       1353       1362       1371       1380

His Asn His Tyr Thr Gln Lys Ser Leu Ser Leu Ser Pro Gly Lys TER
CAC AAC CAC TAC ACG CAG AAG AGC CTC TCC CTG TCT CCG GGT AAA TGA
        1389        1398        1407       1416       1425
```

FIG. 9c

```
ATG GAC ATG AGG GTC CCC GCT CAG CTC CTG GGG CTC CTG CTA CTC TGG              48
Met Asp Met Arg Val Pro Ala Gln Leu Leu Gly Leu Leu Leu Leu Trp
        9           18          27          36          45

CTC CGA GGT GCC AGA TGT GAC ATC CAG ATG ACC CAG TCT CCA TCC TCC              96
Leu Arg Gly Ala Arg Cys Asp Ile Gln Met Thr Gln Ser Pro Ser Ser
                    66          75          84          93

CTG TCT GCA TCT GTC GGA GAC AGA GTC ACC ATC ACT TGC CGG GCA AGT             144
Leu Ser Ala Ser Val Gly Asp Arg Val Thr Ile Thr Cys Arg Ala Ser
    102         111         120         129         138

CAG AGC ATT GCC AGT TAT GTA AAT TGG TAT CAA CAG AAA CCA GGG AAA             192
Gln Ser Ile Ala Ser Tyr Val Asn Trp Tyr Gln Gln Lys Pro Gly Lys
147         156         165         174         183         192

GCC CCT AAA GTC CTC ATT TTT GCT TCA GCC AAT TTG GTG AGT GGG GTC             240
Ala Pro Lys Val Leu Ile Phe Ala Ser Ala Asn Leu Val Ser Gly Val
        201         210         219         228         237

CCA TCA AGA TTC AGT GGC AGT GGA TCT GGG ACA GTT TTC ACC CTC ACC             288
Pro Ser Arg Phe Ser Gly Ser Gly Ser Gly Thr Val Phe Thr Leu Thr
        246         255         264         273         282

ATC AGC AAT CTG CAA CCT GAA GAT TTT GCA ACC TAC TTC TGT CAG CAG             336
Ile Ser Asn Leu Gln Pro Glu Asp Phe Ala Thr Tyr Phe Cys Gln Gln
291         300         309         318         327         336

AGT TAC ACT AAT TTC AGT TTT GGC CAG GGG ACC AAG CTG GAA ATC AAA             384
Ser Tyr Thr Asn Phe Ser Phe Gly Gln Gly Thr Lys Leu Glu Ile Lys
        345         354         363         372         381

CGT ACG GTG GCT GCA CCA TCT GTC TTC ATC TTC CCG CCA TCT GAT GAG             432
Arg Thr Val Ala Ala Pro Ser Val Phe Ile Phe Pro Pro Ser Asp Glu
390         399         408         417         426

CAG TTG AAA TCT GGA ACT GCC TCT GTT GTG TGC CTG CTG AAT AAC TTC             480
Gln Leu Lys Ser Gly Thr Ala Ser Val Val Cys Leu Leu Asn Asn Phe
435         444         453         462         471         480

TAT CCC AGA GAG GCC AAA GTA CAG TGG AAG GTG GAT AAC GCC CTC CAA             528
Tyr Pro Arg Glu Ala Lys Val Gln Trp Lys Val Asp Asn Ala Leu Gln
        489         498         507         516         525

TCG GGT AAC TCC CAG GAG AGT GTC ACA GAG CAG GAC AGC AAG GAC AGC             576
Ser Gly Asn Ser Gln Glu Ser Val Thr Glu Gln Asp Ser Lys Asp Ser
534         543         552         561         570

ACC TAC AGC CTC AGC AGC ACC CTG ACG CTG AGC AAA GCA GAC TAC GAG             624
Thr Tyr Ser Leu Ser Ser Thr Leu Thr Leu Ser Lys Ala Asp Tyr Glu
579         588         597         606         615         624

AAA CAC AAA GTC TAC GCC TGC GAA GTC ACC CAT CAG GGC CTG AGC TCG             672
Lys His Lys Val Tyr Ala Cys Glu Val Thr His Gln Gly Leu Ser Ser
        633         642         651         660         669

CCC GTC ACA AAG AGC TTC AAC AGG GGA GAG TGT TGA                             708
Pro Val Thr Lys Ser Phe Asn Arg Gly Glu Cys *
    678         687         696         705
```

FIG. 11a

```
ATG GGT TGG AGC CTC ATC TTG CTC TTC CTT GTC GCT GTT GCT ACG CGT        48
Met Gly Trp Ser Leu Ile Leu Leu Phe Leu Val Ala Val Ala Thr Arg
            240                 245                 250

GTC TTG TCC CAG GTA CAG TTG CAG GAG TCT GGT CCT GCG CTG GTA AAA        96
Val Leu Ser Gln Val Gln Leu Gln Glu Ser Gly Pro Ala Leu Val Lys
            255                 260                 265

CCC ACA CAG ACC CTC ACA CTG ACC TGC ACC TTC TCT GGG TTC TCA CTC       144
Pro Thr Gln Thr Leu Thr Leu Thr Cys Thr Phe Ser Gly Phe Ser Leu
            270                 275                 280

AGC ACC AGA GGA ATG AGT GTG AAC TGG ATC CGT CAG CCC CCA GGG AAG       192
Ser Thr Arg Gly Met Ser Val Asn Trp Ile Arg Gln Pro Pro Gly Lys
285             290                 295                 300

GCC CTG GAA TGG CTA GCC CGC ATT GAT TGG GAC GAT GAT ACA TTC TAC       240
Ala Leu Glu Trp Leu Ala Arg Ile Asp Trp Asp Asp Asp Thr Phe Tyr
                305                 310                 315

AGC GCT TCT CTG AAG ACT AGG CTC AGC ATC TCC AAG GAC ACC TCC AAA       288
Ser Ala Ser Leu Lys Thr Arg Leu Ser Ile Ser Lys Asp Thr Ser Lys
                320                 325                 330

AAC CAG GTG GTC CTC AGA ATG ACC AAC GTA GAC CCT GTG GAC ACA GCC       336
Asn Gln Val Val Leu Arg Met Thr Asn Val Asp Pro Val Asp Thr Ala
            335                 340                 345

ACA TAT TTT TGT GCA CGG GCC TCA CTA TAT GAC AGT GAT AGT TTC TAC       384
Thr Tyr Phe Cys Ala Arg Ala Ser Leu Tyr Asp Ser Asp Ser Phe Tyr
        350                 355                 360

CTC TTC TAC CAT GCC TAC TGG GGC CAG GGA ACC GTG GTC ACC GTC TCC       432
Leu Phe Tyr His Ala Tyr Trp Gly Gln Gly Thr Val Val Thr Val Ser
365             370                 375                 380

TCA GCT AGC ACC AAG GGC CCA TCG GTC TTC CCC CTG GCA CCC TCC TCC       480
Ser Ala Ser Thr Lys Gly Pro Ser Val Phe Pro Leu Ala Pro Ser Ser
                385                 390                 395

AAG AGC ACC TCT GGG GGC ACA GCG GCC CTG GGC TGC CTG GTC AAG GAC       528
Lys Ser Thr Ser Gly Gly Thr Ala Ala Leu Gly Cys Leu Val Lys Asp
            400                 405                 410

TAC TTC CCC GAA CCG GTG ACG GTG TCG TGG AAC TCA GGC GCC CTG ACC       576
Tyr Phe Pro Glu Pro Val Thr Val Ser Trp Asn Ser Gly Ala Leu Thr
            415                 420                 425

AGC GGC GTG CAC ACC TTC CCG GCT GTC CTA CAG TCC TCA GGA CTC TAC       624
Ser Gly Val His Thr Phe Pro Ala Val Leu Gln Ser Ser Gly Leu Tyr
            430                 435                 440

TCC CTC AGC AGC GTG GTG ACC GTG CCC TCC AGC AGC TTG GGC ACC CAG       672
Ser Leu Ser Ser Val Val Thr Val Pro Ser Ser Ser Leu Gly Thr Gln
445             450                 455                 460

ACC TAC ATC TGC AAC GTG AAT CAC AAG CCC AGC AAC ACC AAG GTG GAC       720
Thr Tyr Ile Cys Asn Val Asn His Lys Pro Ser Asn Thr Lys Val Asp
                465                 470                 475

AAG AAA GCA GAG CCC AAA TCT TGT GAC AAA                               750
Lys Lys Ala Glu Pro Lys Ser Cys Asp Lys
            480                 485
```

Thr His Thr Cys Pro Pro Cys Pro Ala Pro Glu Leu Leu Gly Gly Pro Ser Val Phe Leu Phe
     ACT CAC ACA TGC CCA CCG TGC CCA GCA CCT GAA CTC CTG GGG GGA CCG TCA GTC TTC CTC TTC
             759         768         777         786         795         804         813

Pro Pro Lys Pro Lys Asp Thr Leu Met Ile Ser Arg Thr Pro Glu Val Thr Cys Val Val Val
     CCC CCA AAA CCC AAG GAC ACC CTC ATG ATC TCC CGG ACC CCT GAG GTC ACA TGC GTG GTG GTG
             822         831         840         849         858         867         876

Asp Val Ser His Glu Asp Pro Glu Val Lys Phe Asn Trp Tyr Val Asp Gly Val Glu Val His
     GAC GTG AGC CAC GAA GAC CCT GAG GTC AAG TTC AAC TGG TAC GTG GAC GGC GTG GAG GTG CAT
             885         894         903         912         921         930         939

Asn Ala Lys Thr Lys Pro Arg Glu Glu Gln Tyr Asn Ser Thr Tyr Arg Val Val Ser Val Leu
     AAT GCC AAG ACA AAG CCG CGG GAG GAG CAG TAC AAC AGC ACG TAC CGT GTG GTC AGC GTC CTC
             948         957         966         975         984         993        1002

Thr Val Leu His Gln Asp Trp Leu Asn Gly Lys Glu Tyr Lys Cys Lys Val Ser Asn Lys Ala
     ACC GTC CTG CAC CAG GAC TGG CTG AAT GGC AAG GAG TAC AAG TGC AAG GTC TCC AAC AAA GCC
            1011        1020        1029        1038        1047        1056        1065

Leu Pro Ala Pro Ile Glu Lys Thr Ile Ser Lys Ala Lys Gly Gln Pro Arg Glu Pro Gln Val
     CTC CCA GCC CCC ATC GAG AAA ACC ATC TCC AAA GCC AAA GGG CAG CCC CGA GAA CCA CAG GTG
            1074        1083        1092        1101        1110        1119        1128

Tyr Thr Leu Pro Pro Ser Arg Asp Glu Leu Thr Lys Asn Gln Val Ser Leu Thr Cys Leu Val
     TAC ACC CTG CCC CCA TCC CGG GAT GAG CTG ACC AAG AAC CAG GTC AGC CTG ACC TGC CTG GTC
            1137        1146        1155        1164        1173        1182        1191

Lys Gly Phe Tyr Pro Ser Asp Ile Ala Val Glu Trp Glu Ser Asn Gly Gln Pro Glu Asn Asn
     AAA GGC TTC TAT CCC AGC GAC ATC GCC GTG GAG TGG GAG AGC AAT GGG CAG CCG GAG AAC AAC
            1200        1209        1218        1227        1236        1245        1254

Tyr Lys Thr Thr Pro Pro Val Leu Asp Ser Asp Gly Ser Phe Phe Leu Tyr Ser Lys Leu Thr
     TAC AAG ACC ACG CCT CCC GTG CTG GAC TCC GAC GGC TCC TTC TTC CTC TAC AGC AAG CTC ACC
            1263        1272        1281        1290        1299        1308        1317

Val Asp Lys Ser Arg Trp Gln Gln Gly Asn Val Phe Ser Cys Ser Val Met His Glu Ala Leu
     GTG GAC AAG AGC AGG TGG CAG CAG GGG AAC GTC TTC TCA TGC TCC GTG ATG CAT GAG GCT CTG
            1326        1335        1344        1353        1362        1371        1380

His Asn His Tyr Thr Gln Lys Ser Leu Ser Leu Ser Pro Gly Lys TER
     CAC AAC CAC TAC ACG CAG AAG AGC CTC TCC CTG TCT CCG GGT AAA TGA
            1389        1398        1407        1416        1425
```

FIG. 11c

SEQUENCE LISTING (1) GENERAL INFORMATION:

(iii) NUMBER OF SEQUENCES: 19

```
(2) INFORMATION FOR SEQ ID NO: 1:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "Nucleotide 1 wherein N =
        (AG)10."

(ix) FEATURE:
        (A) NAME/KEY: misc_feature
        (B) LOCATION: 9
        (D) OTHER INFORMATION: /note= "Nucleotide 9 wherein N =
        (T/C)."

(ix) FEATURE:
        (A) NAME/KEY: misc_feature
        (B) LOCATION: 13
        (D) OTHER INFORMATION: /note= "Nucleotide 13 wherein N =
        (G/C)."

(ix) FEATURE:
        (A) NAME/KEY: misc_feature
        (B) LOCATION: 22
        (D) OTHER INFORMATION: /note= "Nucleotide 22 wherein N =
        (G/C)."

(xi) SEQUENCE DESCRIPTION: SEQ ID NO: 1:

NACGCGTGNC CANTCCCAGG TNCAGCTGGT G                               31

(2) INFORMATION FOR SEQ ID NO: 2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "Nucleotide 1 wherein N =
        (AG)10."

(ix) FEATURE:
        (A) NAME/KEY: misc_feature
        (B) LOCATION: 11
        (D) OTHER INFORMATION: /note= "Nucleotide 11 wherein N =
        (T/C)."

(ix) FEATURE:
        (A) NAME/KEY: misc_feature
        (B) LOCATION: 22
        (D) OTHER INFORMATION: /note= "Nucleotide 22 wherein N =
        (A/G)."

(ix) FEATURE:
        (A) NAME/KEY: misc_feature
        (B) LOCATION: 26
        (D) OTHER INFORMATION: /note= "Nucleotide 26 wherein N =
        (C/T)."

(ix) FEATURE:
        (A) NAME/KEY: misc_feature
        (B) LOCATION: 29
        (D) OTHER INFORMATION: /note= "Nucleotide 29 wherein N =
        (C/A)."
```

(xi) SEQUENCE DESCRIPTION: SEQ ID NO: 2:

NACGCGTGTC NTGTCCCAGG TNCAGNTGNA G                              31

(2) INFORMATION FOR SEQ ID NO: 3:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1
         (D) OTHER INFORMATION: /note= "Nucleotide 1 wherein N =
         (AG)10."

(xi) SEQUENCE DESCRIPTION: SEQ ID NO: 3:

NACGCGTGTC CAGTGTGAGG TGCAGCTG                                  28

(2) INFORMATION FOR SEQ ID NO: 4:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1
         (D) OTHER INFORMATION: /note= "Nucleotide 1 wherein N =
         (AG)10."

(xi) SEQUENCE DESCRIPTION: SEQ ID NO: 4:

NACGCGTGTC CTGTCCCAGG TGCAG                                     25

(2) INFORMATION FOR SEQ ID NO: 5:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1
         (D) OTHER INFORMATION: /note= "Nucleotide 1 wherein N =
         (AG)10."

(xi) SEQUENCE DESCRIPTION: SEQ ID NO: 5:

NACGCGTGTC TGGCCGAAGT GCAGCTGGTG                                30

(2) INFORMATION FOR SEQ ID NO: 6:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(ix) FEATURE:

(A) NAME/KEY: misc_feature
            (B) LOCATION: 1
            (D) OTHER INFORMATION: /note= "Nucleotide 1 wherein N =
                (AG)10."

(xi) SEQUENCE DESCRIPTION: SEQ ID NO: 6:

NGCCCTTGGT GCTAGCTGAG GAGACGG                                                27

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "Nucleotide 1 wherein N =
            (AG)10."

(xi) SEQUENCE DESCRIPTION: SEQ ID NO: 7:

NCCAGGTGCA CGATGTGACA TCCAGATGAC C                                           31

(2) INFORMATION FOR SEQ ID NO: 8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "Nucleotide 1 wherein N =
            (AG)10."

(xi) SEQUENCE DESCRIPTION: SEQ ID NO: 8:

NCCTGGATCA CGATGTGATA TTGTGATGAC                                             30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1
        (D) OTHER INFORMATION: /note= "Nucleotide 1 wherein N =
            (AG)10."

(xi) SEQUENCE DESCRIPTION: SEQ ID NO: 9:

NCCAGATACA CGATGTGAAA TTGTGTTGAC                                             30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (genomic)

(ix) FEATURE:
         (A) NAME/KEY: misc_feature
         (B) LOCATION: 1
         (D) OTHER INFORMATION: /note= "Nucleotide 1 wherein N =
         (AG)10."

(xi) SEQUENCE DESCRIPTION: SEQ ID NO: 10:

NTCTGGTGCA CGATGTGACA TCGTGATGAC                                30

(2) INFORMATION FOR SEQ ID NO: 11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 1
         (D) OTHER INFORMATION: /note= "Nucleotide 1 wherein N =
         (AG)10."

(ix) FEATURE:
         (A) NAME/KEY: misc_feature
         (B) LOCATION: 28
         (D) OTHER INFORMATION: /note= "Nucleotide 28 wherein N =
         (G/C)."

(xi) SEQUENCE DESCRIPTION: SEQ ID NO: 11:

NTGCAGCCAC CGTACGTTTG ATTTCCANCT T                               31

(2) INFORMATION FOR SEQ ID NO: 12:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: CDS
         (B) LOCATION: 1..321

(xi) SEQUENCE DESCRIPTION: SEQ ID NO: 12:

```
GAC ATC CAG ATG ACC CAG TCT CCA TCC TCC CTG TCT GCA TCT GTC GGA    48
Asp Ile Gln Met Thr Gln Ser Pro Ser Ser Leu Ser Ala Ser Val Gly
 1               5                  10                  15

GAC AGA GTC ACC ATC ACT TGC CGG GCA GGT CAG AGG ATT GCT AGT TAT    96
Asp Arg Val Thr Ile Thr Cys Arg Ala Gly Gln Arg Ile Ala Ser Tyr
                 20                  25                  30

TTA AAT TGG TAT CAG CAC AAA CCA GGG AAA GCC CCT AAG CTC CTG ATA   144
Leu Asn Trp Tyr Gln His Lys Pro Gly Lys Ala Pro Lys Leu Leu Ile
             35                  40                  45

TAT GCT GGA TCC AAT TTG CAC CGT GGG GTC CCG TCA AGG TTC AGT GGC   192
Tyr Ala Gly Ser Asn Leu His Arg Gly Val Pro Ser Arg Phe Ser Gly
         50                  55                  60

GGT GGA TCT GGG ACA GAT TTC ACT CTC ACC ATC AAC AGT CTG CAA CCT   240
Gly Gly Ser Gly Thr Asp Phe Thr Leu Thr Ile Asn Ser Leu Gln Pro
 65                  70                  75                  80

GAA GAT TTT GCA ACT TAC TAT TGT CAA CAG GCT TAC AGT ACC CCC TGG   288
Glu Asp Phe Ala Thr Tyr Tyr Cys Gln Gln Ala Tyr Ser Thr Pro Trp
```

```
Glu Asp Phe Ala Thr Tyr Tyr Cys Gln Gln Ala Tyr Ser Thr Pro Trp
            85                  90                  95

ACT TTC GGC CCA GGG ACC AAG GTG GAA ATC AAA                        321
Thr Phe Gly Pro Gly Thr Lys Val Glu Ile Lys
            100                 105
```

(2) INFORMATION FOR SEQ ID NO: 13:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..378

(xi) SEQUENCE DESCRIPTION: SEQ ID NO: 13:

```
CAG GTG CAG TTG CAG GAG TCT GGT CCT GTG GTG GTG AAA CCC ACA GAG    48
Gln Val Gln Leu Gln Glu Ser Gly Pro Val Val Val Lys Pro Thr Glu
            110                 115                 120

ACC CTC ACG CTG ACC TGC ACC GTC TCT GGG TTC TCA CTC AGC AAC CCT    96
Thr Leu Thr Leu Thr Cys Thr Val Ser Gly Phe Ser Leu Ser Asn Pro
            125                 130                 135

AGA ATG GGT GTG ACC TGG ATC CGT CAG CCC CCG GGG AAG GCC CTA GAA   144
Arg Met Gly Val Thr Trp Ile Arg Gln Pro Pro Gly Lys Ala Leu Glu
140                 145                 150                 155

TGG CTT GGA AAC ATT TTT TCG AGT GAC GAG AAG TCC TTC AGT CCT TCT   192
Trp Leu Gly Asn Ile Phe Ser Ser Asp Glu Lys Ser Phe Ser Pro Ser
            160                 165                 170

CTG AAG AGC AGA CTC ACC ACC TCC CAG GAC ACC TCC AGA AGC CAG GTG   240
Leu Lys Ser Arg Leu Thr Thr Ser Gln Asp Thr Ser Arg Ser Gln Val
            175                 180                 185

GTC CTA AGC TTG ACC AAC GTG GAC CCT GTG GAC ACA GCC ACA TAT TAC   288
Val Leu Ser Leu Thr Asn Val Asp Pro Val Asp Thr Ala Thr Tyr Tyr
            190                 195                 200

TGT GCA CGG GTA GGA CTG TAT GAC ATC AAT GCT TAT TAC CTA TAC TAC   336
Cys Ala Arg Val Gly Leu Tyr Asp Ile Asn Ala Tyr Tyr Leu Tyr Tyr
            205                 210                 215

CTG GAT TAT TGG GGG CAG GGA ACC CTG GTC ACC GTC TCC TCA           378
Leu Asp Tyr Trp Gly Gln Gly Thr Leu Val Thr Val Ser Ser
220                 225                 230
```

(2) INFORMATION FOR SEQ ID NO: 14:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..318

(xi) SEQUENCE DESCRIPTION: SEQ ID NO: 14:

```
GAC ATC CAG ATG ACC CAG TCT CCA TCC TCC CTG TCT GCA TCT GTC GGA    48
Asp Ile Gln Met Thr Gln Ser Pro Ser Ser Leu Ser Ala Ser Val Gly
            130                 135                 140

GAC AGA GTC ACC ATC ACT TGC CGG GCA AGT CAG AGC ATT GCC AGT TAT    96
Asp Arg Val Thr Ile Thr Cys Arg Ala Ser Gln Ser Ile Ala Ser Tyr
```

```
                145                 150                 155
GTA AAT TGG TAT CAA CAG AAA CCA GGG AAA GCC CCT AAA GTC CTC ATT         144
Val Asn Trp Tyr Gln Gln Lys Pro Gly Lys Ala Pro Lys Val Leu Ile
    160                 165                 170

TTT GCT TCA GCC AAT TTG GTG AGT GGG GTC CCA TCA AGA TTC AGT GGC         192
Phe Ala Ser Ala Asn Leu Val Ser Gly Val Pro Ser Arg Phe Ser Gly
175                 180                 185                 190

AGT GGA TCT GGG ACA GTT TTC ACC CTC ACC ATC AGC AAT CTG CAA CCT         240
Ser Gly Ser Gly Thr Val Phe Thr Leu Thr Ile Ser Asn Leu Gln Pro
                195                 200                 205

GAA GAT TTT GCA ACC TAC TTC TGT CAG CAG AGT TAC ACT AAT TTC AGT         288
Glu Asp Phe Ala Thr Tyr Phe Cys Gln Gln Ser Tyr Thr Asn Phe Ser
            210                 215                 220

TTT GGC CAG GGG ACC AAG CTG GAA ATC AAA                                 318
Phe Gly Gln Gly Thr Lys Leu Glu Ile Lys
            225                 230

(2) INFORMATION FOR SEQ ID NO: 15:

(i) SEQUENCE CHARACTERISTICS:
         (A) LENGTH: 378 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 1..378

(xi) SEQUENCE DESCRIPTION: SEQ ID NO: 15:

CAG GTA CAG TTG CAG GAG TCT GGT CCT GCG CTG GTA AAA CCC ACA CAG          48
Gln Val Gln Leu Gln Glu Ser Gly Pro Ala Leu Val Lys Pro Thr Gln
1               5                   10                  15

ACC CTC ACA CTG ACC TGC ACC TTC TCT GGG TTC TCA CTC AGC ACT AGA          96
Thr Leu Thr Leu Thr Cys Thr Phe Ser Gly Phe Ser Leu Ser Thr Arg
                20                  25                  30

GGA ATG AGT GTG AAC TGG ATC CGT CAG CCC CCA GGG AAG GCC CTG GAA         144
Gly Met Ser Val Asn Trp Ile Arg Gln Pro Pro Gly Lys Ala Leu Glu
            35                  40                  45

TGG CTA GCC CGC ATT GAT TGG GAC GAT GAT ACA TTC TAC AGC GCT TCT         192
Trp Leu Ala Arg Ile Asp Trp Asp Asp Asp Thr Phe Tyr Ser Ala Ser
50                  55                  60

CTG AAG ACT AGG CTC AGC ATC TCC AAG GAC ACC TCC AAA AAC CAG GTG         240
Leu Lys Thr Arg Leu Ser Ile Ser Lys Asp Thr Ser Lys Asn Gln Val
65                  70                  75                  80

GTC CTC AGA ATG ACC AAC GTA GAC CCT GTG GAC ACA GCC ACA TAT TTT         288
Val Leu Arg Met Thr Asn Val Asp Pro Val Asp Thr Ala Thr Tyr Phe
                85                  90                  95

TGT GCA CGG GCC TCA CTA TAT GAC AGT GAT AGT TTC TAC CTC TTC TAC         336
Cys Ala Arg Ala Ser Leu Tyr Asp Ser Asp Ser Phe Tyr Leu Phe Tyr
                100                 105                 110

CAT GCC TAC TGG GGC CAG GGA ACC GTG GTC ACC GTC TCC TCA                 378
His Ala Tyr Trp Gly Gln Gly Thr Val Val Thr Val Ser Ser
            115                 120                 125

(2) INFORMATION FOR SEQ ID NO: 16:

(i) SEQUENCE CHARACTERISTICS:
         (A) LENGTH: 705 base pairs
         (B) TYPE: nucleic acid
         (C) STRANDEDNESS: single
         (D) TOPOLOGY: linear
```

(ii) MOLECULE TYPE: DNA (genomic)

(ix) FEATURE:
             (A) NAME/KEY: CDS
             (B) LOCATION: 1..705

(xi) SEQUENCE DESCRIPTION: SEQ ID NO: 16:

```
ATG GAG ACC CCT GCT CAG CTC CTG GGG CTC CTG CTA CTC TGG CTC CGA        48
Met Glu Thr Pro Ala Gln Leu Leu Gly Leu Leu Leu Leu Trp Leu Arg
        130                 135                 140

GGT GCC AGA TGT GAC ATC CAG ATG ACC CAG TCT CCA TCC TCC CTG TCT        96
Gly Ala Arg Cys Asp Ile Gln Met Thr Gln Ser Pro Ser Ser Leu Ser
145                 150                 155

GCA TCT GTC GGA GAC AGA GTC ACC ATC ACT TGC CGG GCA GGT CAG AGG       144
Ala Ser Val Gly Asp Arg Val Thr Ile Thr Cys Arg Ala Gly Gln Arg
160                 165                 170

ATT GCT AGT TAT TTA AAT TGG TAT CAG CAC AAA CCA GGG AAA GCC CCT       192
Ile Ala Ser Tyr Leu Asn Trp Tyr Gln His Lys Pro Gly Lys Ala Pro
175                 180                 185                 190

AAG CTC CTG ATA TAT GCT GGA TCC AAT TTG CAC CGT GGG GTC CCG TCA       240
Lys Leu Leu Ile Tyr Ala Gly Ser Asn Leu His Arg Gly Val Pro Ser
                195                 200                 205

AGG TTC AGT GGC GGT GGA TCT GGG ACA GAT TTC ACT CTC ACC ATC AAC       288
Arg Phe Ser Gly Gly Gly Ser Gly Thr Asp Phe Thr Leu Thr Ile Asn
        210                 215                 220

AGT CTG CAA CCT GAA GAT TTT GCA ACT TAC TAT TGT CAA CAG GCT TAC       336
Ser Leu Gln Pro Glu Asp Phe Ala Thr Tyr Tyr Cys Gln Gln Ala Tyr
225                 230                 235

AGT ACC CCC TGG ACT TTC GGC CCA GGG ACC AAG GTG GAA ATC AAA CGT       384
Ser Thr Pro Trp Thr Phe Gly Pro Gly Thr Lys Val Glu Ile Lys Arg
240                 245                 250

ACG GTG GCT GCA CCA TCT GTC TTC ATC TTC CCG CCA TCT GAT GAG CAG       432
Thr Val Ala Ala Pro Ser Val Phe Ile Phe Pro Pro Ser Asp Glu Gln
255                 260                 265                 270

TTG AAA TCT GGA ACT GCC TCT GTT GTG TGC CTG CTG AAT AAC TTC TAT       480
Leu Lys Ser Gly Thr Ala Ser Val Val Cys Leu Leu Asn Asn Phe Tyr
                275                 280                 285

CCC AGA GAG GCC AAA GTA CAG TGG AAG GTG GAT AAC GCC CTC CAA TCG       528
Pro Arg Glu Ala Lys Val Gln Trp Lys Val Asp Asn Ala Leu Gln Ser
        290                 295                 300

GGT AAC TCC CAG GAG AGT GTC ACA GAG CAG GAC AGC AAG GAC AGC ACC       576
Gly Asn Ser Gln Glu Ser Val Thr Glu Gln Asp Ser Lys Asp Ser Thr
305                 310                 315

TAC AGC CTC AGC AGC ACC CTG ACG CTG AGC AAA GCA GAC TAC GAG AAA       624
Tyr Ser Leu Ser Ser Thr Leu Thr Leu Ser Lys Ala Asp Tyr Glu Lys
320                 325                 330

CAC AAA GTC TAC GCC TGC GAA GTC ACC CAT CAG GGC CTG AGC TCG CCC       672
His Lys Val Tyr Ala Cys Glu Val Thr His Gln Gly Leu Ser Ser Pro
335                 340                 345                 350

GTC ACA AAG AGC TTC AAC AGG GGA GAG TGT TGA                           705
Val Thr Lys Ser Phe Asn Arg Gly Glu Cys *
                355                 360
```

(2) INFORMATION FOR SEQ ID NO: 17:

(i) SEQUENCE CHARACTERISTICS:
             (A) LENGTH: 1428 base pairs
             (B) TYPE: nucleic acid
             (C) STRANDEDNESS: single
             (D) TOPOLOGY: linear (ii) MOLECULE TYPE: DNA (genomic)

(ix) FEATURE:
    (A) NAME/KEY: CDS
    (B) LOCATION: 1..1428

(xi) SEQUENCE DESCRIPTION: SEQ ID NO: 17:

| | | | | | | | | | | | | | | | | |
|---|---|---|---|---|---|---|---|---|---|---|---|---|---|---|---|---|
| ATG | GGT | TGG | AGC | CTC | ATC | TTG | CTC | TTC | CTT | GTC | GCT | GTT | GCT | ACG | CGT | 48 |
| Met | Gly | Trp | Ser | Leu | Ile | Leu | Leu | Phe | Leu | Val | Ala | Val | Ala | Thr | Arg | |
| | | | 240 | | | | 245 | | | | | 250 | | | | |
| GTC | CTG | TCC | CAG | GTG | CAG | TTG | CAG | GAG | TCT | GGT | CCT | GTG | GTG | GTG | AAA | 96 |
| Val | Leu | Ser | Gln | Val | Gln | Leu | Gln | Glu | Ser | Gly | Pro | Val | Val | Val | Lys | |
| | | 255 | | | | | 260 | | | | | 265 | | | | |
| CCC | ACA | GAG | ACC | CTC | ACG | CTG | ACC | TGC | ACC | GTC | TCT | GGG | TTC | TCA | CTC | 144 |
| Pro | Thr | Glu | Thr | Leu | Thr | Leu | Thr | Cys | Thr | Val | Ser | Gly | Phe | Ser | Leu | |
| | | 270 | | | | | 275 | | | | | 280 | | | | |
| AGC | AAC | CCT | AGA | ATG | GGT | GTG | ACC | TGG | ATC | CGT | CAG | CCC | CCC | GGG | AAG | 192 |
| Ser | Asn | Pro | Arg | Met | Gly | Val | Thr | Trp | Ile | Arg | Gln | Pro | Pro | Gly | Lys | |
| | 285 | | | | | 290 | | | | | 295 | | | | | |
| GCC | CTA | GAA | TGG | CTT | GGA | AAC | ATT | TTT | TCG | AGT | GAC | GAG | AAG | TCC | TTC | 240 |
| Ala | Leu | Glu | Trp | Leu | Gly | Asn | Ile | Phe | Ser | Ser | Asp | Glu | Lys | Ser | Phe | |
| 300 | | | | | 305 | | | | | 310 | | | | | 315 | |
| AGT | CCT | TCT | CTG | AAG | AGC | AGA | CTC | ACC | ACC | TCC | CAG | GAC | ACC | TCC | AGA | 288 |
| Ser | Pro | Ser | Leu | Lys | Ser | Arg | Leu | Thr | Thr | Ser | Gln | Asp | Thr | Ser | Arg | |
| | | | 320 | | | | | 325 | | | | | 330 | | | |
| AGC | CAG | GTG | GTC | CTA | AGC | TTG | ACC | AAC | GTG | GAC | CCT | GTG | GAC | ACA | GCC | 336 |
| Ser | Gln | Val | Val | Leu | Ser | Leu | Thr | Asn | Val | Asp | Pro | Val | Asp | Thr | Ala | |
| | | | 335 | | | | | 340 | | | | | 345 | | | |
| ACA | TAT | TAC | TGT | GCA | CGG | GTA | GGA | CTG | TAT | GAC | ATC | AAT | GCT | TAT | TAC | 384 |
| Thr | Tyr | Tyr | Cys | Ala | Arg | Val | Gly | Leu | Tyr | Asp | Ile | Asn | Ala | Tyr | Tyr | |
| | | 350 | | | | | 355 | | | | | 360 | | | | |
| CTA | TAC | TAC | CTG | GAT | TAT | TGG | GGG | CAG | GGA | ACC | CTG | GTC | ACC | GTC | TCC | 432 |
| Leu | Tyr | Tyr | Leu | Asp | Tyr | Trp | Gly | Gln | Gly | Thr | Leu | Val | Thr | Val | Ser | |
| | 365 | | | | | 370 | | | | | 375 | | | | | |
| TCA | GCT | AGC | ACC | AAG | GGC | CCA | TCG | GTC | TTC | CCC | CTG | GCA | CCC | TCC | TCC | 480 |
| Ser | Ala | Ser | Thr | Lys | Gly | Pro | Ser | Val | Phe | Pro | Leu | Ala | Pro | Ser | Ser | |
| 380 | | | | | 385 | | | | | 390 | | | | | 395 | |
| AAG | AGC | ACC | TCT | GGG | GGC | ACA | GCG | GCC | CTG | GGC | TGC | CTG | GTC | AAG | GAC | 528 |
| Lys | Ser | Thr | Ser | Gly | Gly | Thr | Ala | Ala | Leu | Gly | Cys | Leu | Val | Lys | Asp | |
| | | | 400 | | | | | 405 | | | | | 410 | | | |
| TAC | TTC | CCC | GAA | CCG | GTG | ACG | GTG | TCG | TGG | AAC | TCA | GGC | GCC | CTG | ACC | 576 |
| Tyr | Phe | Pro | Glu | Pro | Val | Thr | Val | Ser | Trp | Asn | Ser | Gly | Ala | Leu | Thr | |
| | | | 415 | | | | | 420 | | | | | 425 | | | |
| AGC | GGC | GTG | CAC | ACC | TTC | CCG | GCT | GTC | CTA | CAG | TCC | TCA | GGA | CTC | TAC | 624 |
| Ser | Gly | Val | His | Thr | Phe | Pro | Ala | Val | Leu | Gln | Ser | Ser | Gly | Leu | Tyr | |
| | | 430 | | | | | 435 | | | | | 440 | | | | |
| TCC | CTC | AGC | AGC | GTG | GTG | ACC | GTG | CCC | TCC | AGC | AGC | TTG | GGC | ACC | CAG | 672 |
| Ser | Leu | Ser | Ser | Val | Val | Thr | Val | Pro | Ser | Ser | Ser | Leu | Gly | Thr | Gln | |
| | 445 | | | | | 450 | | | | | 455 | | | | | |
| ACC | TAC | ATC | TGC | AAC | GTG | AAT | CAC | AAG | CCC | AGC | AAC | ACC | AAG | GTG | GAC | 720 |
| Thr | Tyr | Ile | Cys | Asn | Val | Asn | His | Lys | Pro | Ser | Asn | Thr | Lys | Val | Asp | |
| 460 | | | | | 465 | | | | | 470 | | | | | 475 | |
| AAG | AAA | GCA | GAG | CCC | AAA | TCT | TGT | GAC | AAA | ACT | CAC | ACA | TGC | CCA | CCG | 768 |
| Lys | Lys | Ala | Glu | Pro | Lys | Ser | Cys | Asp | Lys | Thr | His | Thr | Cys | Pro | Pro | |
| | | | | 480 | | | | | 485 | | | | | 490 | | |
| TGC | CCA | GCA | CCT | GAA | CTC | CTG | GGG | GGA | CCG | TCA | GTC | TTC | CTC | TTC | CCC | 816 |
| Cys | Pro | Ala | Pro | Glu | Leu | Leu | Gly | Gly | Pro | Ser | Val | Phe | Leu | Phe | Pro | |
| | | | 495 | | | | | 500 | | | | | 505 | | | |
| CCA | AAA | CCC | AAG | GAC | ACC | CTC | ATG | ATC | TCC | CGG | ACC | CCT | GAG | GTC | ACA | 864 |
| Pro | Lys | Pro | Lys | Asp | Thr | Leu | Met | Ile | Ser | Arg | Thr | Pro | Glu | Val | Thr | |
| | 510 | | | | | 515 | | | | | 520 | | | | | |

-continued

```
TGC GTG GTG GTG GAC GTG AGC CAC GAA GAC CCT GAG GTC AAG TTC AAC        912
Cys Val Val Val Asp Val Ser His Glu Asp Pro Glu Val Lys Phe Asn
    525                 530                 535

TGG TAC GTG GAC GGC GTG GAG GTG CAT AAT GCC AAG ACA AAG CCG CGG        960
Trp Tyr Val Asp Gly Val Glu Val His Asn Ala Lys Thr Lys Pro Arg
540                 545                 550                 555

GAG GAG CAG TAC AAC AGC ACG TAC CGT GTG GTC AGC GTC CTC ACC GTC       1008
Glu Glu Gln Tyr Asn Ser Thr Tyr Arg Val Val Ser Val Leu Thr Val
                560                 565                 570

CTG CAC CAG GAG TGG CTG AAT GGC AAG GAG TAC AAG TGC AAG GTC TCC       1056
Leu His Gln Glu Trp Leu Asn Gly Lys Glu Tyr Lys Cys Lys Val Ser
            575                 580                 585

AAC AAA GCC CTC CCA GCC CCC ATC GAG AAA ACC ATC TCC AAA GCC AAA       1104
Asn Lys Ala Leu Pro Ala Pro Ile Glu Lys Thr Ile Ser Lys Ala Lys
        590                 595                 600

GGG CAG CCC CGA GAA CCA CAG GTG TAC ACC CTG CCC CCA TCC CGG GAT       1152
Gly Gln Pro Arg Glu Pro Gln Val Tyr Thr Leu Pro Pro Ser Arg Asp
    605                 610                 615

GAG CTG ACC AAG AAC CAG GTC AGC CTG ACC TGC CTG GTC AAA GGC TTC       1200
Glu Leu Thr Lys Asn Gln Val Ser Leu Thr Cys Leu Val Lys Gly Phe
620                 625                 630                 635

TAT CCC AGC GAC ATC GCC GTG GAG TGG GAG AGC AAT GGG CAG CCG GAG       1248
Tyr Pro Ser Asp Ile Ala Val Glu Trp Glu Ser Asn Gly Gln Pro Glu
                640                 645                 650

AAC AAC TAC AAG ACC ACG CCT CCC GTG CTG GAC TCC GAC GGC TCC TTC       1296
Asn Asn Tyr Lys Thr Thr Pro Pro Val Leu Asp Ser Asp Gly Ser Phe
            655                 660                 665

TTC CTC TAC AGC AAG CTC ACC GTG GAC AAG AGC AGG TGG CAG CAG GGG       1344
Phe Leu Tyr Ser Lys Leu Thr Val Asp Lys Ser Arg Trp Gln Gln Gly
        670                 675                 680

AAC GTC TTC TCA TGC TCC GTG ATG CAT GAG GCT CTG CAC AAC CAC TAC       1392
Asn Val Phe Ser Cys Ser Val Met His Glu Ala Leu His Asn His Tyr
    685                 690                 695

ACG CAG AAG AGC CTC TCC CTG TCT CCG GGT AAA TGA                       1428
Thr Gln Lys Ser Leu Ser Leu Ser Pro Gly Lys *
700                 705                 710
```

(2) INFORMATION FOR SEQ ID NO: 18:

(i) SEQUENCE CHARACTERISTICS:
        (A) LENGTH: 708 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..708

(xi) SEQUENCE DESCRIPTION: SEQ ID NO: 18:

```
ATG GAC ATG AGG GTC CCC GCT CAG CTC CTG GGG CTC CTG CTA CTC TGG         48
Met Asp Met Arg Val Pro Ala Gln Leu Leu Gly Leu Leu Leu Leu Trp
                475                 480                 485                 490

CTC CGA GGT GCC AGA TGT GAC ATC CAG ATG ACC CAG TCT CCA TCC TCC         96
Leu Arg Gly Ala Arg Cys Asp Ile Gln Met Thr Gln Ser Pro Ser Ser
            495                 500                 505

CTG TCT GCA TCT GTC GGA GAC AGA GTC ACC ATC ACT TGC CGG GCA AGT        144
Leu Ser Ala Ser Val Gly Asp Arg Val Thr Ile Thr Cys Arg Ala Ser
        510                 515                 520

CAG AGC ATT GCC AGT TAT GTA AAT TGG TAT CAA CAG AAA CCA GGG AAA        192
Gln Ser Ile Ala Ser Tyr Val Asn Trp Tyr Gln Gln Lys Pro Gly Lys
```

```
525                530                535                540
GCC CCT AAA GTC CTC ATT TTT GCT TCA GCC AAT TTG GTG AGT GGG GTC    240
Ala Pro Lys Val Leu Ile Phe Ala Ser Ala Asn Leu Val Ser Gly Val
            545                550                555

CCA TCA AGA TTC AGT GGC AGT GGA TCT GGG ACA GTT TTC ACC CTC ACC    288
Pro Ser Arg Phe Ser Gly Ser Gly Ser Gly Thr Val Phe Thr Leu Thr
            560                565                570

ATC AGC AAT CTG CAA CCT GAA GAT TTT GCA ACC TAC TTC TGT CAG CAG    336
Ile Ser Asn Leu Gln Pro Glu Asp Phe Ala Thr Tyr Phe Cys Gln Gln
            575                580                585

AGT TAC ACT AAT TTC AGT TTT GGC CAG GGG ACC AAG CTG GAA ATC AAA    384
Ser Tyr Thr Asn Phe Ser Phe Gly Gln Gly Thr Lys Leu Glu Ile Lys
            590                595                600

CGT ACG GTG GCT GCA CCA TCT GTC TTC ATC TTC CCG CCA TCT GAT GAG    432
Arg Thr Val Ala Ala Pro Ser Val Phe Ile Phe Pro Pro Ser Asp Glu
605             610                615                620

CAG TTG AAA TCT GGA ACT GCC TCT GTT GTG TGC CTG CTG AAT AAC TTC    480
Gln Leu Lys Ser Gly Thr Ala Ser Val Val Cys Leu Leu Asn Asn Phe
            625                630                635

TAT CCC AGA GAG GCC AAA GTA CAG TGG AAG GTG GAT AAC GCC CTC CAA    528
Tyr Pro Arg Glu Ala Lys Val Gln Trp Lys Val Asp Asn Ala Leu Gln
            640                645                650

TCG GGT AAC TCC CAG GAG AGT GTC ACA GAG CAG GAC AGC AAG GAC AGC    576
Ser Gly Asn Ser Gln Glu Ser Val Thr Glu Gln Asp Ser Lys Asp Ser
            655                660                665

ACC TAC AGC CTC AGC AGC ACC CTG ACG CTG AGC AAA GCA GAC TAC GAG    624
Thr Tyr Ser Leu Ser Ser Thr Leu Thr Leu Ser Lys Ala Asp Tyr Glu
670             675                680

AAA CAC AAA GTC TAC GCC TGC GAA GTC ACC CAT CAG GGC CTG AGC TCG    672
Lys His Lys Val Tyr Ala Cys Glu Val Thr His Gln Gly Leu Ser Ser
685             690                695                700

CCC GTC ACA AAG AGC TTC AAC AGG GGA GAG TGT TGA                     708
Pro Val Thr Lys Ser Phe Asn Arg Gly Glu Cys *
            705                710

(2) INFORMATION FOR SEQ ID NO: 19:

(i) SEQUENCE CHARACTERISTICS:
        (A) LENGTH: 1428 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1428

(xi) SEQUENCE DESCRIPTION: SEQ ID NO: 19:

ATG GGT TGG AGC CTC ATC TTG CTC TTC CTT GTC GCT GTT GCT ACG CGT    48
Met Gly Trp Ser Leu Ile Leu Leu Phe Leu Val Ala Val Ala Thr Arg
            240                245                250

GTC TTG TCC CAG GTA CAG TTG CAG GAG TCT GGG CCT GCG CTG GTA AAA    96
Val Leu Ser Gln Val Gln Leu Gln Glu Ser Gly Pro Ala Leu Val Lys
            255                260                265

CCC ACA CAG ACC CTC ACA CTG ACC TGC ACC TTC TCT GGG TTC TCA CTC    144
Pro Thr Gln Thr Leu Thr Leu Thr Cys Thr Phe Ser Gly Phe Ser Leu
            270                275                280

AGC ACC AGA GGA ATG AGT GTG AAC TGG ATC CGT CAG CCC CCA GGG AAG    192
Ser Thr Arg Gly Met Ser Val Asn Trp Ile Arg Gln Pro Pro Gly Lys
285             290                295                300
```

```
GCC CTG GAA TGG CTA GCC CGC ATT GAT TGG GAC GAT GAT ACA TTC TAC      240
Ala Leu Glu Trp Leu Ala Arg Ile Asp Trp Asp Asp Asp Thr Phe Tyr
            305                 310                 315

AGC GCT TCT CTG AAG ACT AGG CTC AGC ATC TCC AAG GAC ACC TCC AAA      288
Ser Ala Ser Leu Lys Thr Arg Leu Ser Ile Ser Lys Asp Thr Ser Lys
            320                 325                 330

AAC CAG GTG GTC CTC AGA ATG ACC AAC GTA GAC CCT GTG GAC ACA GCC      336
Asn Gln Val Val Leu Arg Met Thr Asn Val Asp Pro Val Asp Thr Ala
            335                 340                 345

ACA TAT TTT TGT GCA CGG GCC TCA CTA TAT GAC AGT GAT AGT TTC TAC      384
Thr Tyr Phe Cys Ala Arg Ala Ser Leu Tyr Asp Ser Asp Ser Phe Tyr
        350                 355                 360

CTC TTC TAC CAT GCC TAC TGG GGC CAG GGA ACC GTG GTC ACC GTC TCC      432
Leu Phe Tyr His Ala Tyr Trp Gly Gln Gly Thr Val Val Thr Val Ser
365                 370                 375                 380

TCA GCT AGC ACC AAG GGC CCA TCG GTC TTC CCC CTG GCA CCC TCC TCC      480
Ser Ala Ser Thr Lys Gly Pro Ser Val Phe Pro Leu Ala Pro Ser Ser
            385                 390                 395

AAG AGC ACC TCT GGG GGC ACA GCG GCC CTG GGC TGC CTG GTC AAG GAC      528
Lys Ser Thr Ser Gly Gly Thr Ala Ala Leu Gly Cys Leu Val Lys Asp
            400                 405                 410

TAC TTC CCC GAA CCG GTG ACG GTG TCG TGG AAC TCA GGC GCC CTG ACC      576
Tyr Phe Pro Glu Pro Val Thr Val Ser Trp Asn Ser Gly Ala Leu Thr
            415                 420                 425

AGC GGC GTG CAC ACC TTC CCG GCT GTC CTA CAG TCC TCA GGA CTC TAC      624
Ser Gly Val His Thr Phe Pro Ala Val Leu Gln Ser Ser Gly Leu Tyr
        430                 435                 440

TCC CTC AGC AGC GTG GTG ACC GTG CCC TCC AGC AGC TTG GGC ACC CAG      672
Ser Leu Ser Ser Val Val Thr Val Pro Ser Ser Ser Leu Gly Thr Gln
445                 450                 455                 460

ACC TAC ATC TGC AAC GTG AAT CAC AAG CCC AGC AAC ACC AAG GTG GAC      720
Thr Tyr Ile Cys Asn Val Asn His Lys Pro Ser Asn Thr Lys Val Asp
            465                 470                 475

AAG AAA GCA GAG CCC AAA TCT TGT GAC AAA ACT CAC ACA TGC CCA CCG      768
Lys Lys Ala Glu Pro Lys Ser Cys Asp Lys Thr His Thr Cys Pro Pro
            480                 485                 490

TGC CCA GCA CCT GAA CTC CTG GGG GGA CCG TCA GTC TTC CTC TTC CCC      816
Cys Pro Ala Pro Glu Leu Leu Gly Gly Pro Ser Val Phe Leu Phe Pro
            495                 500                 505

CCA AAA CCC AAG GAC ACC CTC ATG ATC TCC CGG ACC CCT GAG GTC ACA      864
Pro Lys Pro Lys Asp Thr Leu Met Ile Ser Arg Thr Pro Glu Val Thr
510                 515                 520

TGC GTG GTG GTG GAC GTG AGC CAC GAA GAC CCT GAG GTC AAG TTC AAC      912
Cys Val Val Val Asp Val Ser His Glu Asp Pro Glu Val Lys Phe Asn
525                 530                 535                 540

TGG TAC GTG GAC GGC GTG GAG GTG CAT AAT GCC AAG ACA AAG CCG CGG      960
Trp Tyr Val Asp Gly Val Glu Val His Asn Ala Lys Thr Lys Pro Arg
            545                 550                 555

GAG GAG CAG TAC AAC AGC ACG TAC CGT GTG GTC AGC GTC CTC ACC GTC     1008
Glu Glu Gln Tyr Asn Ser Thr Tyr Arg Val Val Ser Val Leu Thr Val
            560                 565                 570

CTG CAC CAG GAC TGG CTG AAT GGC AAG GAG TAC AAG TGC AAG GTC TCC     1056
Leu His Gln Asp Trp Leu Asn Gly Lys Glu Tyr Lys Cys Lys Val Ser
            575                 580                 585

AAC AAA GCC CTC CCA GCC CCC ATC GAG AAA ACC ATC TCC AAA GCC AAA     1104
Asn Lys Ala Leu Pro Ala Pro Ile Glu Lys Thr Ile Ser Lys Ala Lys
            590                 595                 600

GGG CAG CCC CGA GAA CCA CAG GTG TAC ACC CTG CCC CCA TCC CGG GAT     1152
Gly Gln Pro Arg Glu Pro Gln Val Tyr Thr Leu Pro Pro Ser Arg Asp
605                 610                 615                 620
```

```
GAG CTG ACC AAG AAC CAG GTC AGC CTG ACC TGC CTG GTC AAA GGC TTC        1200
Glu Leu Thr Lys Asn Gln Val Ser Leu Thr Cys Leu Val Lys Gly Phe
                625                 630                 635

TAT CCC AGC GAC ATC GCC GTG GAG TGG GAG AGC AAT GGG CAG CCG GAG        1248
Tyr Pro Ser Asp Ile Ala Val Glu Trp Glu Ser Asn Gly Gln Pro Glu
                640                 645                 650

AAC AAC TAC AAG ACC ACG CCT CCC GTG CTG GAC TCC GAC GGC TCC TTC        1296
Asn Asn Tyr Lys Thr Thr Pro Pro Val Leu Asp Ser Asp Gly Ser Phe
                655                 660                 665

TTC CTC TAC AGC AAG CTC ACC GTG GAC AAG AGC AGG TGG CAG CAG GGG        1344
Phe Leu Tyr Ser Lys Leu Thr Val Asp Lys Ser Arg Trp Gln Gln Gly
                670                 675                 680

AAC GTC TTC TCA TGC TCC GTG ATG CAT GAG GCT CTG CAC AAC CAC TAC        1392
Asn Val Phe Ser Cys Ser Val Met His Glu Ala Leu His Asn His Tyr
685                 690                 695                 700

ACG CAG AAG AGC CTC TCC CTG TCT CCG GGT AAA TGA                        1428
Thr Gln Lys Ser Leu Ser Leu Ser Pro Gly Lys *
                705                 710
```

NEUTRALIZING HIGH AFFINITY HUMAN MONOCLONAL ANTIBODIES SPECIFIC TO RSV F-PROTEIN AND METHODS FOR THEIR MANUFACTURE AND THERAPEUTIC USE THEREOF

This application is a continuation of application Ser. No. 08/770,057, filed Dec. 19, 1996; now U.S. Pat. No. 5,958,765 which in turn is a divisional of application Ser. No. 08/488,376, filed Jun. 7, 1995 now U.S. Pat. No. 5,811,524.

BACKGROUND OF THE INVENTION

Respiratory syncytial virus (RSV) is a Parmixovirus of the Pneumovirus genus which commonly infects the upper and lower respiratory tract. It is so contagious that by age two, a large percentage of children have been infected by it. Moreover, by age four, virtually all humans have an immunity to RSV.

Typically, RSV infections are mild, remaining localized in the upper respiratory tract and causing symptoms similar to a common cold which require no extensive treatment. However, in some subjects, e.g., immunosuppressed individuals such as infants, elderly persons or patients with underlying cardiopulmonary diseases, the virus may penetrate to the lower respiratory tract requiring hospitalization and breathing support. In some of these cases, RSV infection may cause permanent lung damage or even be life threatening. In the United States alone, RSV results in about 90,000 hospitalizations each year, and results in about 4500 deaths.

RSV appears in two major strain subgroups, A and B, primarily based on serological differences associated with the attachment glycoprotein, G. The major surface glycoprotein, i.e., the 90 kD G protein, can differ up to 50% at the amino acid level between isolates Johnson et al, *Proc. Natl. Acad. Sci.* (1987), 84, 5625–5629. By contrast, a potential therapeutic target, the 70 kD fusion (F) protein, is highly conserved across different RSV strains, about i.e., 89% on the amino acid level Johnson et al. *J. Gen. Virol.* (1988), 69, 2623–2628, Johnson et al, *J. Virol.* (1987), 10, 3163–3166, P. L. Collins, Plenum Press, NY (1991), 103–162. Moreover, it is known that antibodies elicited against F-protein of a given type are cross-reactive with the other type.

The F-protein is a heterodimer, generated from a linear precursor, consisting of disulfide-linked fragments of 48 and 23 kD respectively Walsh et al, *J. Gen. Virol,* (1985), 66, 401–415. Inhibition of syncytia formation by polyclonal antibodies is associated with significant reaction to the 23 kD fragment.

As noted, while RSV infections are usually mild, in some individuals RSV infections may be life threatening. Currently, severe RSV infection is treated by administration of the antiviral agent Ribavarin. However, while Ribavarin exhibits some efficacy in controlling RSV infection, its use is disfavored for several reasons. For example, it is highly expensive and may be administered only in hospitals. Other known RSV treatments only treat the symptoms of RSV infection and include the use of aerosolized bronchodilators in patients with bronchiolitis and corticosteroid therapy in patients with bronchiolitis and RSV pneumonia.

To date, RSV vaccines intended to boost antiviral protective antibodies have been largely unsuccessful. For example, a vaccine based on formalin-inactivated RSV that was tested approximately 25 years ago, induced antibodies that were deficient in fusion inhibiting activity Murphy et al. *Clinical Microbiology* (1988), 26, 1595–1597, and sometimes even exacerbated the disease. This may potentially be explained to the inability of the formalin inactivated virus to induce protective antibodies. While high antibody titers were measured in vaccine recipients, specific protective titers were lower than in the control population. This may be because formalin inactivated RSV does not display the necessary conformational epitopes required to elicit protective antibodies.

While there is no known effective RSV vaccine to date, there exists some clinical evidence that antibody therapy may confer protection against RSV infection in susceptible individuals, and may even clear an existing RSV infection. For example, it has been reported that newborn infants show a low incidence of severe bronchiolitis, which is hypothesized to be attributable to the presence of protective maternal antibodies Ozilvie et al. *J. Med Virol* (1981), 7, 263–271. Also, children who are immune to reinfection exhibit statistically higher anti-F-protein titers than those who are reinfected. Moreover, intravenous immune globulin (IVIG) prepared from high titer RSV-immune donors reduces nasal RSV shedding and improves oxygenation Hemming et al. *Anti. Viral Agents and Chemotherapy* (1987), 31, 1882–1886. Also, recent studies have suggested that the virus can be fought and lung damage prevented by administering RSV-enriched immune globulin (RSVIG) Groothuis et al. *The New England J. Med.* (1993), 329, 1524–1530, K. McIntosh, *The New England J. Med.* (1993), 329, 1572–1573, J. R. Groothuis, *Antiviral Research,* (1994), 23, 1–10, Siber et al. *J. Infectious Diseases* (1994), 169, 1368–1373, Siber et al. *J. Infectious Diseases* (1992), 165:456–463.

Similarly, some animal studies suggest that antibody therapy with virus neutralizing antibodies may confer protection against RSV or even clear an existing RSV infection. For example, in vitro neutralizing mouse monoclonal antibodies have been reported to protect mice against infection and also to clear established RSV infections Taylor et al, *J.Immunology,* (1984), 52, 137–142, Stott et al., "*Immune Responses, Virus Infections and Disease,* I.R.L. Press, London (1989), 85–104. Also, monoclonal antibodies to the F-protein of RSV have shown high efficacy in both in vitro and in vivo RSV models Tempest et al, *Bio/Technology,* (1991), 9, 266–271, Crowe et al. *Proc. Natl. Acad. Sci.* (1994), 91, 1386–1390, Walsh et al. *Infection and Immunity,* (1984), 43, 756–758, Barbas III, et al, *Proc. Natl. Acad. Sci.* (1992), 89, 10164–10168, Walsh, et al, *J. Gen. Virol.* (1986), 67, 505–513. Antibody concentrations as low as 520–2000 µg/kg body weight have been reported to result in almost instant recovery in animal studies Crowe et al, *Proc. Natl. Acad. Sci.* (1994), 91, 1386–1390. Moreover, these monoclonal antibodies have been disclosed to neutralize both A and B strains, including laboratory strains and wildtype strains. These antibodies were administered either by injection Groothuis et al, *The New England J. Med.* (1993), 329, 1524–1530, Siber et al, *J. Infectious Diseases* (1994), 169, 1368–1373 or by aerosol Crowe et al, *Proc. Natl. Acad. Sci.* (1994), 91, 1386–1390.

Two different types of potentially therapeutic monoclonal antibodies to the RSV F-protein have been previously described in the literature, humanized murine antibodies Tempest et al, *Biol. Technology,* (1991) 9, 266–271, or true human antibodies (Fab fragments) Barbas III, et al, *Proc. Natl. Acad. Sci.* (1992), 89, 10164–10168. Humanized murine antibodies were generated by CDR grafting a cross-strain neutralizing murine anti-F-protein antibody onto a generic human Fc, as well as structural areas of the variable part. The human Fab fragments were produced by combinatorial library technology using human bone marrow cells obtained from an HIV positive donor (immunocompromised). The therapeutic in vivo titers of the humanized and human RSV antibodies were 5 and 2 mg/kg body weight, respectively. It is noted, however, that the humanized antibodies were tested in a syncytia inhibition assay, whereas the human anti-RSV Fab fragments were assayed to determine their virus neutralization activity. Therefore, the results reported with the humanized and human anti-RSV antibodies are not directly comparable.

The Fab fragment generated by the combinatorial library technology were disclosed to be efficient in aerosol. This is probably because of the relatively small size of the molecule. These results are highly encouraging because a major target population for an RSV vaccine is infants. Therefore, aerosol is a particularly desirable mode of administration.

However, notwithstanding the previous published reports of humanized and Fab fragments specific to RSV, there still exists a significant need for improved anti-RSV antibodies having improved therapeutic potential, in particular anti-RSV antibodies which possess high affinity and specificity for the RSV F-protein which effectively neutralize and prevent RSV infection.

Antibody therapy can be subdivided into two principally different activities: (i) passive immunotherapy using intact non-labeled antibodies or labeled antibodies and (ii) active immunotherapy using anti-idiotypes for re-establishment of network balance in autoimmunity.

In passive immunotherapy, naked antibodies are administered to neutralize an antigen or to direct effector functions to targeted membrane associated antigens. Neutralization would be of a lymphokine, a hormone, or an anaphylatoxin, i.e., C5a. Effector functions include complement fixation, macrophage activation and recruitrnent, and antibody dependent cell mediated cytotoxicity (ADCC). Naked antibodies have been used to treat leukemia Ritz et al, *S. F. Blood. (*1981), 58, 141–152 and antibodies to GD2 have been used in treatments of neuroblastomas Schulz et al, *Cancer Res.* (1984), 44:5914 and melanomas Irie et al., *Proc. Natl. Acad. Sci.,* (1986, 83:8694. Also, intravenous immune gamma globulin (IVIG) antibodies with high anti-RSV titers recently were used in experimental trials to treat respiratory distress caused by RSV infection Hemming et al, *Anti. Viral Agents and Chemotherapy,* (1987), 31, 1882–1886, Groothuis et al., *The New England J. Med.* (1993), 329, 1524–1530, K. McIntosh, *The New England J. Med.* (1993), 329, 1572–1573, J. R. Groothuis, *Antiviral Research,* (1994), 23, 1–10, Siber et al, *J. Infectious Diseases* (1994), 169, 1368–1373.

The therapeutic efficacy of a monoclonal antibody depends on factors including, e.g., the amount, reactivity, specificity and class of the antibody bound to the antigen. Also, the in vivo half-life of the antibody is a significant therapeutic factor.

Still another factor which may significantly affect the therapeutic potential of antibodies is their species of origin. Currently, monoclonal antibodies used for immunotherapy are almost exclusively of rodent origin Schulz et al, *Cancer Res.* (1984), 44:5914, Miller et al, *Blood* (1981), 58, 78–86, Lanzavecchia et al, *J. Edp. Med.* (1988), 167, 345–352, Sikora et al, *Br. Med. Bull.* (1984), 40:240, Tsuiisaki et al, *Cancer Research* (1991), 51:2599, largely because the generation of rodent monoclonal antibodies uses well characterized and highly efficient techniques Köhler et al, *Nature,* (1975), 256:495, Galfre et al, *Nature,* (1977), 266:550. However, while rodent monoclonal antibodies possess therapeutic efficacy, they can present restrictions and disadvantages relative to human antibodies. For example, they often induce sub-optimal stimulation of host effector functions (CDCC, ADCC, etc.). Also, murine antibodies may induce human anti-murine antibody (HAMA) responses Schroff et al, *Can. Res.* (1985, 45:879–885, Shawler et al, *J. Immunol.* (1985), 135:1530–1535. This may result in shortened antibody half-life Dillman et al, *Mod.* (1986), 5, 73–84, Miller et al, *Blood,* (1983), 62:988–995 and in some instances may cause toxic side effects such as serum sickness and anaphylaxis.

In some subjects, e.g., heavily immunosuppressed subjects (e.g., patients subjected to heavy chemical or radiation mediated cancer therapy Irie et al, *Proc. Natl. Acad. Sci.* (1986), 83:8694, Dillman et al, *Mod.* (1986), 5, 73–84, Koprowski et al, *Proc. Natl. Acad. Sci.* (1984), 81:216–219), use of murine monoclonal antibodies causes limited negative side effects. By contrast, in patients with normal or hyperactive immune systems, murine antibodies, at least for some disease conditions may exhibit limited efficacy.

In an effort to obviate limitations of murine monoclonal antibodies, recombinant DNA techniques have been applied to produce chimeric antibodies Morrison et al, *Proc. Natl. Acad. Sci.* (1984), 81:216–219, Boulianne et al, *Nature,* (1984), 312, 644–646, humanized antibodies by "CDR grafting" Riechmann et al, *Nature* (1984), 332, 323–327 and "veneered" antibodies by substitution of specific surface residues with other amino acids to alleviate or eliminate antigenicity.

However, although such antibodies have been used successfully clinically Gillis et al, *J. Immunol. Meth* (1989), 25:191, they have proven cumbersome to produce. This is because the understanding of the requirements for optimal antigen recognition and affinity is not yet fully understood. Also, the human framework and the mouse CDR regions often interact sterically with a negative effect on antibody activity. Moreover, such antibodies sometimes still induce strong HAMA responses in patients.

Human antibodies present major advantages over their murine counterparts; they induce optional effector functions, they do not induce HAMA responses and host antigen-specific antibodies may lead to identification of epitopes of therapeutic value that may be too subtle to be recognized by a xenogeneic immune system Lennox et al, "*Monoclonal Antibodies in Clinical Medicine,*" London: Academic Press (1982).

While human antibodies are highly desirable, their production is complicated by various factors including ethical considerations, and the fact that conventional methods for producing human antibodies are often inefficient. For example, human subjects cannot generally be adequately immunized with most antigens because of ethical and safety considerations. Consequently, reports of isolation of human monoclonal antibodies with useful affinities, $\geqq 10^8$ molar to specific antigens are few McCabe et al, *Cancer Research,* (1988), 48, 4348–4353. Also, isolation of anti-viral human monoclonal antibodies from donor primed cells has proved to be unwieldy. For example, Gorny reported that only 7 of 14,329 EBV transformed cultures of peripheral blood mononuclear cells (PMBC's) from HIV positive donors resulted in stable, specific anti-HIV antibody producing cell lines Gorny et al, *Proc. Natl. Acad. Sci.* (1989), 86:1624–1628.

To date, most human anti-tumor antibodies have been generated from peripheral blood lymphocytes (PBLs) Irie et al, *Br. J. Cancer,* (1981), 44:262 or tumor draining lymph node lymphocytes Schlom et al, *Proc. Natl. Acad. Sci.* (1980), 77:6841–6845, Cote et al, *Proc. Natl. Acad. Sci.* (1983), 80:2026–2030 from cancer patients. However, such antibodies often react with intracellular, and thus therapeutically useless antigens Ho et al, *In Hybridoma Technology*, Amsterdam (1988), 37–57 or are of the IgM class McCabe et al, *Cancer Research* (1988), 48, 4348–4353, a class of antibodies with lesser ability to penetrate solid tumors than IgGs. Few of these human antibodies have moved to clinical trials Drobyski et al, *R.C. Transplantation* (1991), 51, 1190–1196, suggesting that the rescued antibodies may possess sub-optimal qualities. Moreover, since these approaches exploit the testing donor primed B cells, it is clear that these cells are not an optimal source for rescue of useful monoclonal antibodies.

Recently, generation of human antibodies from primed donors has been improved by stimulation with CD40 resulting in expansion of human B cells Banchereau et al, *F. Science* (1991), 251:70, Zhang et al, *J. Immunol.* (1990), 144, 2955–2960, Tohma et al, *J. Immunol.* (1991), 146:2544–2552 or by an extra in vitro booster step primer to immortalization Chaudhuri et al, *Cancer Supplement* (1994), 73, 1098–1104. This principle has been exploited to generate human monoclonal antibodies to Cytomegalovirus, Epstein-Barr Virus (EBV) and Hemophilus influenza with cells from primed donors Steenbakkers et al, *Hum. Antibod. Hybridomas* (1993), 4, 166–173; Ferrarro et al, *Hum. Antibod. Hybridomas* (1993), 4, 80–85, Kwekkeboom et al, *Immunol. Methods* (1993), 160, 117–127, with a significantly higher yield than obtained with other methods Gorny, et al, *Proc. Natl. Acad. Sci. USA* (1989), 86, 1624–1628.

Moreover, to address the limitations of donor priming, immunization and cultivation ex vivo of lymphocytes from healthy donors has been reported. Some success in generating human monoclonal antibodies using ex homine boosting of PBL cells from primed donors has been reported Maeda et al, *Hybridoma* (1986), 5:33–41, Kozbor et al, *J. Immunol.* (1984), 14:23, Duchosal et al, *Nature* (1992, 355:258–262. The feasibility of immunizing in vitro was first demonstrated in 1967 by Mishell and Dutton Mishell et al, *J. Exp. Med* (1967), 126:423–442 using murine lymphocytes. In 1973, Hoffman successfully immunized human lymphocytes Hoffman et al, *Nature* (1973), 243:408–410. Also, successful primary immunizations have been reported with lymphocytes from peripheral blood Luzzati et al, *J. Exp. Med.* (1975), 144:573:585, Misiti et al, *J. Exp. Med.* (1981), 154:1069–1084, Komatsu et al, *Int. Archs. Allergy Appl. Inmunol.* (1986), 80:431–434, Ohlin et al, *C.A.K. Immunology* (1989), 68:325 (1989) tonsils Strike et al, *J. Immunol.* (1978), 132:1789–1803 and spleens, the latter obtained from trauma Ho et al, *In Hybridoma Technology*, Amsterdam (1988), 37–57, Boerner et al, *J. Immunol.* (1991), 147:86–95, Ho et al, *J. Immunol.* (1985), 135:3831–3838, Wasserman et al, *J. Immunol. Meth.* (1986), 93:275–283, Wasserman et al, *J. Immunol. Meth.* (1986), 93:275–283, Brams et al, *Hum. Antibod. Hybridomas* (1993), 4, 47–56, Brams et al, *Hum. Antibod. Hybridomas* (1993), 4, 57–65 and idiopathic thrombocytopenia purpura (ITP) patients Boerner et al, *J. Immunol.* (1991), 147:86–95, Brams et al, *Hum. Antibod. Hybridomas* (1993) 4, 47–56, Brams et al, *Hum. Antibod. Hybridomas* (1993), 4, 57–65, McRoberts et al, "In Vitro Immunization in Hybridoma Technology", Elsevier, Amsterdam (1988), 267–275, Lu et al, *P. Hybridoma* (1993), 12, 381–389.

In vitro immunization offers considerable advantages, e.g., easily reproducible immunizations, lends itself easily to manipulation of antibody class by means of appropriate cultivation and manipulation techniques Chaudhuri et al, *Cancer Supplement* (1994), 73, 1098–1104. Also, there is evidence that the in vivo tolerance to self-antigens is not prevalent during IVI Boerner et al, *J. Immunol.* (1991), 147:86–95, Brams et al, *J. Immunol. Methods* (1987), 98:11. Therefore, this technique is potentially applicable for production of antibodies to self-antigens, e.g., tumor markers and receptors involved in autoimmunity.

Several groups have reported the generation of responses to a variety of antigens challenged only in vitro, e.g., tumor associated antigens (TAAs) Boerner et al, *J. Immunol.* (1991), 147:86–95, Borrebaeck et al, *Proc. Natl. Acad. Sci.* (1988), 85:3995. However, unfortunately, the resulting antibodies were typically of the IgM and not the IgG subclass McCabe et al, *Cancer Research* (1988), 48, 4348–4353, Koda et al, *Hum. Antibod. Hybridomas,* (1990), 1:15 and secondary (IgG) responses have only been reported with protocols using lymphocytes from immunized donors. Therefore, it would appear that these protocols only succeed in inducing a primary immune response but require donor immunized cells for generation of recall responses.

Also, research has been conducted to systematically analyze cultivation and immunization variables to develop a general protocol for effectively inducing human monoclonal antibodies in vitro Boerner, *J. Immunol.* (1991) 147:86–95, Brams et al, *Hum. Antibod. Hybridomas* (1993), 4, 47–56, Lu et al, *Hybridoma* (1993), 12, 381–389. This has resulted in the isolation of human monoclonal antibodies specific for ferritin Boerner et al, *J. Immunol.* (1991), 147:86–95, induced by IVI of naive human spleen cells. Also, this research has resulted in a protocol by which de novo secondary (IgG) responses may be induced entirely in vitro Brams et al, *Hum. Antibod. Hybridomas* (1993), 4, 57–65.

However, despite the great potential advantages of IVI, the efficiency of such methods are severely restricted because of the fact that immune cells grow in monolayers in culture vessels. By contrast, in vivo germinal centers possessing a three-dimensional structure are found in the spleen during the active phases of an immune response. These three-dimensional structures comprise activated T- and B-cells surrounded by antigen-presenting cells which are believed by the majority of immunologists to compare the site of antigen-specific activation of B-cells.

An alternative to the natural splenic environment is to "recreate" or mimic splenic conditions in an immunocompromised animal host, such as the "Severe Combined Immune Deficient" (SCID) mouse. Human lymphocytes are readily adopted by the SCID mouse (hu-SCID) and produce high levels of immunoglobulins Mosier et al, *Nature* (1988), 335:256, McCune et al, *L. Science* (1988), 241, 1632–1639. Moreover, if the donor used for reconstitution has been exposed to a particular antigen, a strong secondary response to the same antigen can be elicited in such mice. For example, Duchosal et al, Duchosal et al, *Nature* (1992), 355:258–262 reported that human peripheral blood B-cells from a donor vaccinated with tetanus toxoid 17 years prior could be restimulated in the SCID environment to produce high serum levels, i.e., around $10^4$. They further disclosed cloning and expression of the genes of two human anti-TT antibodies using the lambda and the M13 phage combinatorial library approach Huse et al, *R. A. Science* (1989), 246:1275 from the extracted human cells. The reported antigen affinities of the antibodies were in the $10^8$–$10^9$/M range. However, this protocol required donor primed cells and the yield was very low, only 2 clones were obtained from a library of 370,000 clones.

Therefore, previously the hu-SPL-SCID mouse has only been utilized for producing human monoclonal antibodies to antigens wherein the donor has either been efficiently primed naturally or by vaccination Ståli et al, *Methods in Enzymology* (1983), 92, 26–36, which in most cases involves exposure to viral or bacterial antigens. Also, the reported serum titer levels using the hu-SCID animal model are significantly lower than what is typically achieved by immunization of normal mice.

Additionally, two protocols have been described by which induction of primary antibody responses can be followed by induction of secondary antibody responses in hu-SCID mice using naive human lymphocytes. However, use of both of these protocols are substantially restricted. In the first protocol, primary responses are induced in hu-SCID mice into which human fetal liver, thymus and lymph nodes have been surgically implanted. However, this method is severely restricted by the limited availability of fetal tissue, as well as the complicated surgical methodology of the protocol McCune et al, *L. Science* (1988), 241, 1632–1639. In the second protocol, lethally irradiated normal mice were reconstituted with T- and B-cell depicted human bone marrow and SCID mouse bone marrow cells Lubin et al, *Science,* (1991), 252:427. However, this method is disadvantageous because it requires a four month incubation period. Moreover, both protocols result in very low antibody titers, i.e., below $10^4$.

Also, Carlson et al, Carlsson et al, *J. Immunol.* (1992), 148:1065–1071 described in 1992 an approach using PBMCs from an antigen (tetanus toxoid) primed donor. The cells were first depleted of macrophages and NK cells before being subjected to a brief in vitro cultivation and priming period prior to transfer into a SCID mouse. The hu-SPL-SCID mouse was then boosted with antigen. This method was reported to result in average TT specific human IgG titers of $\approx 10^4$ in the hu-SPL-SCID serum, with up to $5 \times 10^5$ reported.

Production of human monoclonal antibodies further typically requires the production of immortalized B-cells, in order to obtain cells which secrete a constant, ideally permanent supply of the desired human monoclonal antibodies. Immortalization of B-cells is generally effected by one of four approaches: (i) transformation with EBV, (ii) mouse-human heterofusion, (iii) EBV transformation followed by heterofusion, and (iv) combinatorial immunoglobulin gene library techniques.

EBV transformation has been used successfully in a number of reports, mainly for the generation of anti-HIV antibodies Gorny, et al, *Proc. Natl. Acad. Sci.* (1989), 86:1624–1628, Posner, et al, *J. Immunol.* (1991), 146:4325–32. The main advantage is that approximately one of every 200 B-cells becomes transformed. However, EBV transformed cells are typically unstable, produce low amounts of mainly IgM antibody, clone poorly and cease making antibody after several months of culturing. Heterofusion Carrol, et al, *J. Immunol. Meth.* (1986), 89:61–72 is typically favored for producing hybridomas which secrete high levels of IgG antibody. Hybridomas are also easy to clone by limiting dilution. However, a disadvantage is the poor yield, i.e., $\leq 1$ hybridomas per 20,000 lymphocytes Boerner, et al, *J. Immunol.* (1991), 147:86–95, Ohlin. et al, *C.A.K. Immunology* (1989), 68:325, Xiu-mei et al, *Hum. Antibod. Hybridomas* (1990), 1:42, Borrebaeck C.A.K. *Abstract at the "Second International Conference" on "Human Antibodies and Hybridomas,"* Apr. 26–28, 1992, Cambridge, England. Combining EBV transformation followed by heterofusion offers two advantages: (i) human B-cells fuse more readily to the fusion partner after EBV transformation, and (ii) result in more stable, higher producing hybridomas Ohlin, et al, *Immunology* (1989), 68:325, Xiu-mei, et al, *Hum. Antibod. Hybridomas* (1990), 1:42, Borrebaeck C.A.K. *Absract at the "Second International Conference" on "Human Antibodies and Hybridomas,"* Apr. 26–28, 1992, Cambridge, England. The advantage of the fmal technique, i.e., combinatorial immunoglobulin gene library technique is the fact that very large libraries can be screened by means of the M13 Fab expression technology Huse, et al, *Science* (1989), 246:1275, William Huse, *Antibody Engineering: A Practical Guide,* Borrebaeck C.A.K., ed. 5:103–120 and that the genes can easily be transferred to a production cell line. However, the yield is typically extremely low, on the order of 1 per 370,000 clones Duchosal, et al, *Nature* (1992), 355:258–262.

Thus, based on the foregoing, it is apparent that more efficient methods for producing human monoclonal antibodies, in particular antibodies specific to RSV, would be highly advantageous. Moreover, it is also apparent that human antibodies specific to the RSV F-protein having superior binding affinity, specificity and effector functions than those currently available would also be highly desirable.

OBJECTS OF THE INVENTION

It is an object of the invention to provide improved methods for producing human antibodies of high titers which are specific to desired antigens.

It is a more specific object of the invention to provide a novel method for producing high titer human antibodies which comprises (i) antigen priming of naive human splenocytes in vitro, (ii) transferral of in vitro antigen primed splenocyte cells to an immunocompromised donor, e.g., a SCID mouse, and (iii) boosting with antigen.

It is another specific object of the invention to provide improved methods for producing human monoclonal antibodies which are specific to respiratory syncytial virus (RSV), and in particular the RSV fusion (F) protein.

It is another object of the invention to provide an improved method for producing EBV immortalized B-cells which favors the formation of EBV immortalized B-cells which predominantly secrete IgG.

It is a more specific object of the invention to provide an improved method for producing EBV immortalized human B-cells which predominantly secrete IgG's which comprises:

(i) antigen priming of naive human splenocytes in vitro;

(ii) transferral of such in vitro antigen primed naive splenocytes to an immunocompromised donor, e.g., a SCID mouse;

(iii) boosting the immunocompromised donor with antigen;

(iv) isolation of human antibody producing B-cells from the antigen boosted immunocompromised donor, e.g., SCID mouse; and (v) EBV transformation of said isolated human antibody producing B-cells.

It is another object of the invention to provide novel compositions containing EBV transformed human B-cells obtained from SCID mice which predominantly secrete human IgG's.

It is a more specific object of the invention to provide novel compositions containing EBV transformed human B-cells which predominantly secrete human IgG's produced by a method comprising:

(i) antigen priming of naive human splenocytes in vitro;

(ii) transferral of resulting in vitro antigen primed naive splenocytes to an immunocompromised animal donor, e.g., a SCID mouse;

(iii) boosting the immunocompromised animal donor, e.g., SCID mouse, with antigen;

(iv) isolation of human antibody producing B-cells from the antigen boosted immunocompromised donor, e.g., SCID mouse; and (v) EBV transformation of said isolated human antibody producing B-cells.

It is another specific object of the invention to produce RSV neutralizing human monoclonal antibodies having an affinity to the RSV F-protein of $\leq 2 \times 10^{-9}$ Molar.

It is still another object of the invention to provide EBV immortalized cell lines which secrete RSV neutralizing human IgG monoclonal antibodies having an affinity to the RSV F antigen of $\leq 2 \times 10^{9}$ Molar.

It is a more specific object of the present invention to provide two EBV immortalized cell lines, RF-2 and RF-1, which respectively secrete human monoclonal antibodies also referred to as RF-2 and RF-1 which neutralize RSV in vivo and each possess an affinity for the RSV F-protein of $\leq 2 \times 10^{-9}$.

It is another object of the invention to transfect eukaryotic cells with DNA sequences encoding the RF-1 or RF-2 heavy and light variable domains to produce transfectants which secrete human antibodies containing the variable domain of RF-1 or RF-2.

It is a more specific object of the invention to provide transfected CHO cells which express the RF-1 or RF-2 heavy and light variable domains.

It is another object of the invention to treat or prevent RSV infection in humans by administering a therapeutically or prophylactically effective amount of RSV neutralizing human monoclonal antibodies which are specific to the RSV F-protein and which exhibit a Kd for the RSV F-protein of $\leq 2 \times 10^{-9}$ molar.

It is a more specific object of the invention to treat or prevent RSV infection in humans by administering a therapeutically or prophylactically effective amount of RF-1 or RF-2 or a human monoclonal antibody expressed in a transfected eukaryotic cell which contains and expresses the variable heavy and light domains of RF-1 or RF-2.

It is another object of the invention to provide vaccines for treating or preventing RSV infection which comprise a therapeutically or prophylactically effective amount of human monoclonal antibodies specific to the RSV F-protein having a Kd for the RSV F-protein of $\leq 2 \times 10^{-9}$ molar, which neutralize RSV in vitro, in combination with a pharmaceutically acceptable carrier or excipient.

It is a more specific object of the invention to provide vaccines for treating or preventing RSV infection which comprise a therapeutically or prophylactically effective amount of RF-1 or RF-2 or human monoclonal antibodies derived from a transfected eukaryotic cell which contains and expresses DNA sequences encoding the variable heavy and light domains of RF-1 or RF-2, in combination with a pharmaceutically acceptable carrier or excipient.

It is another object of the present invention to provide a method for diagnosis of RSV infection by assaying the presence of RSV in analytes, e.g., respiratory fluids using human monoclonal antibodies which possess an affinity for the RSV fusion (F) protein or $\leq 2 \times 10^{-9}$ molar.

It is still another object of the invention to provide novel immunoprobes and test kits for detection of RSV infection which comprise human monoclonal antibodies specific to the RSV F-protein, which possess an affinity for the RSV F protein of $\leq 2 \times 10^{-9}$ molar, which antibodies are directly or indirectly attached to a suitable reporter molecule, e.g., an enzyme or a radionuclide. In the preferred embodiment these human monoclonal antibodies will comprise RF-1 or RF-2 or recombinant human monoclonal antibodies produced in eukaryotic cells, e.g., CHO cells, which are transfected with the variable heavy and light domains of RF-1 or RF-2.

BRIEF DESCRIPTION OF THE INVENTION

The present invention in its broadest embodiments relates to novel methods for making human antibodies to desired antigens, preferably antigens involved in prophylaxis, treatment or detection of a human disease condition. These methods comprise antigen priming of native human splenocytes in vitro, transferral of the resultant in vitro antigen primed splenocyte cells to an immunocompromised donor, e.g., a SCID mouse, and boosting said immunocompromised donor with antigen.

The present invention also relates to methods for producing Epstein-Barr Virus (EBV) immortalized B-cells which favors the production of cells which secrete IgGs comprising: antigen priming of naive human splenocytes in vitro; transferral of resultant in vitro antigen primed splenocytes to an immunocompromised donor, e.g., a SCID mouse; boosting the immunocompromised donor with antigen; isolating human antibody secreting B-cells, preferably IgG secreting, from the antigen boosted immunocompromised donor, e.g., SCID mouse; and EBV transformation of said isolated human antibody secreting cells.

The present invention more specifically relates to improved methods for making human antibodies to RSV, in particular the RSV fusion (F) protein which exhibit high affinity to RSV F-protein and which also neutralize RSV infection, as well as the human monoclonal antibodies which result from these methods. This is preferably effected by priming of naive human splenocytes in vitro with Il-2 and optionally the RSV F-protein; transferral of the resultant in vitro primed splenocyte cells to an immunocompromised donor, e.g., a SCID mouse, and boosting with RSV F-protein to produce human B-cells which secrete neutralizing anti-RSV F-protein human antibodies having high affinity to the RSV F-protein, i.e., $\leq 2 \times 10^{-9}$ molar.

The resultant B-cells are preferably immortalized so as to provide a constant stable supply of human anti-RSV F-protein monoclonal antibodies. In the preferred embodiment B-cells are isolated from the antigen boosted SCID mouse and transformed with EBV virus to produce EBV transformed human B-cells which predominantly secrete human IgGs.

These cells are then cloned to select EBV transformed cell lines which secrete human monoclonal antibodies having high affinity to RSV F-protein, i.e. $\leq 10^{-7}$ and preferably $\leq 2 \times 10^{-9}$ molar.

The present invention also relates to the use of such anti-RSV F-protein human monoclonal antibodies as therapeutic and/or prophylactic, as well as diagnostic agents. As noted, the subject methods result in the generation of human monoclonal antibodies which exhibit high affinity to the RSV F-protein, i.e., which possess a Kd for the RSV F-protein of $\leq 2 \times 10^{-9}$ molar, which also neutralize RSV in vitro. Therefore, these antibodies are ideally suited as prophylactic and therapeutic agents for preventing or treating RSV infection given the fact that the RSV F-protein is a surface protein which is highly conserved across different RSV isolates. Also, given the high affinity and specificity of the subject human monoclonal antibodies to RSV F-protein, they also may be used to diagnose RSV infection.

More specifically, the present invention provides two particular human monoclonal antibodies to the RSV F-protein, i.e., RF-1 and RF-2, as well as recombinant human antibodies derived therefrom, which are preferably produced in CHO cells, which cells have been transfected with DNA sequences encoding the variable heavy and light domains of RF-1 or RF-2. These antibodies are particularly useful as prophylactic and/or therapeutic agents for treatment or prevention of RSV infection. Moreover, these antibodies are useful as diagnostic agents because they bind the RSV F-protein with high affinity, i.e., each possess affinity for the RSV F-protein of $\leq 2 \times 10^{-9}$. They are especially useful as therapeutic agents because of their high affinity and specificity for the RSV F-protein, and their ability to effectively neutralize RSV infection in vitro.

BRIEF DESCRIPTION OF THE FIGURES

FIG. 7a (SEQ ID NO:12) depicts the amino acid and nucleic acid sequence of the variable light domain of RF-1.

FIG. 7b (SEQ ID NO:13) depicts the amino acid and nucleic acid sequence of the variable heavy domain of RF-1.

FIG. 8a (SEQ ID NO:14) depicts the amino acid and nucleic acid sequence of the variable light domain of RF-2.

FIG. 8b (SEQ ID NO:15) depicts the amino acid and nucleic acid sequence of the variable heavy domain of RF-2.

FIG. 9a (SEQ ID NO:16) depicts the amino acid and nucleic acid sequence of the RF-1 light chain, the leader sequence, and the human kappa constant domain sequence.

FIG. 9b (SEQ ID NO:17) depicts the amino acid and nucleic acid sequence of the RF-1 heavy chain, a leader sequence, and the beginning of the human gamma/constant domain sequence.

FIG. 9c depicts the remainder of the human constant domain sequence.

FIG. 11a (SEQ ID NO:18) depicts the amino acid and nucleic acid sequence of the RF-2 light chain, leader sequence, and human Kappa constant domain.

FIG. 11b (SEQ ID NO:19) depicts the amino acid and nucleic acid sequence of the RF-2 heavy chain, leader sequence, and human gamma/constant domain.

FIG. 11c depicts the amino acid and nucleic acid sequence of the human gamma/constant domain.

DETAILED DESCRIPTION OF THE INVENTION

Figure 1:
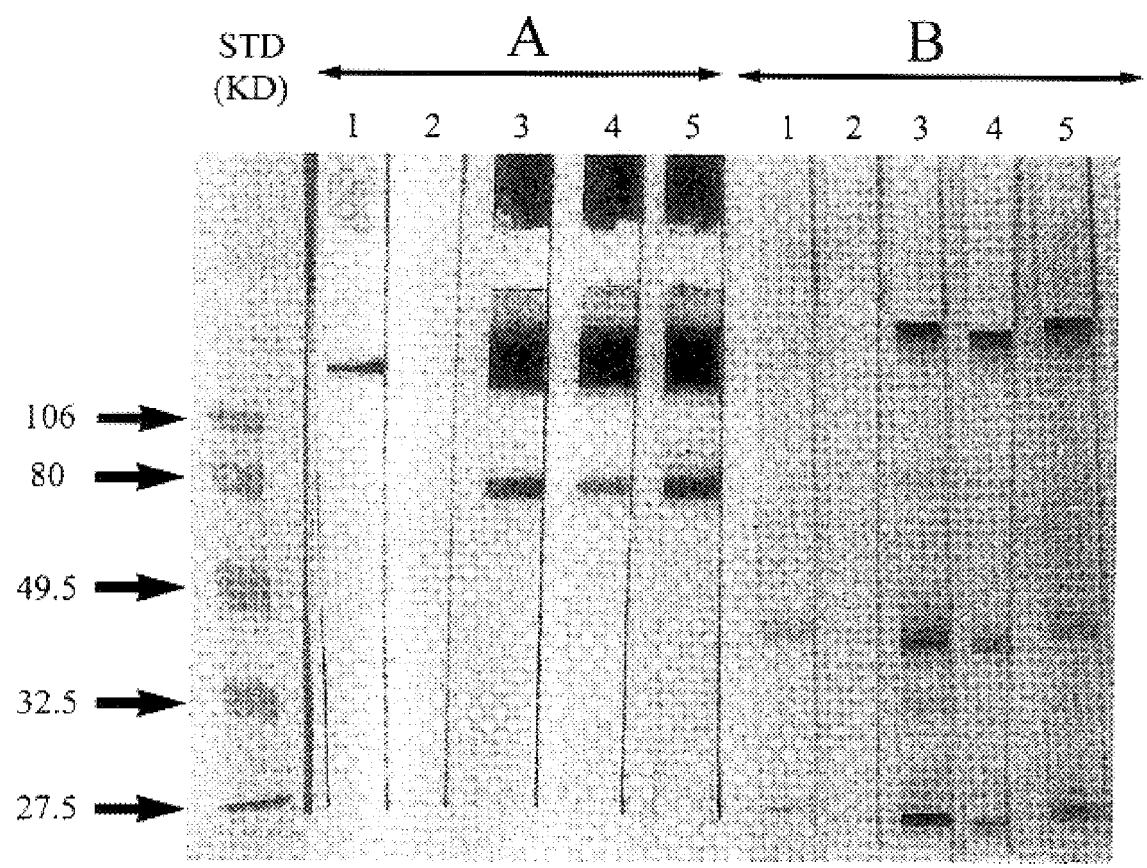
FIGS. 1A and 1B depict an immunoblot of native and denatured F protein, respectively, with anti-F protein hu-SPL-SCID sera. Native (A) and denatured (B) F protein was run in SDS-PAGE and transferred to nitrocellulose by Western blot. Nitrocellulose strips were reacted with positive control mouse anti-F protein MAb (lanes 1A and 1B), negative control hu-SPL-SCID serum anti-TT (lanes 2A and 2B) and hu-SPL-SCID anti-F protein sera from mice #6 (lanes 3A and 3B), #3 (lanes 4A and 4B) and #4 (lanes #5A and 5B).

As discussed, the present invention provides a novel highly efficient method for producing human monoclonal antibodies to desired antigens, preferably antigens which are involved in a human disease condition. Antigens involved in a human disease condition typically will be surface antigens which comprise suitable therapeutic targets for antibodies. For example, this includes surface proteins of viruses and antigens expressed on the surface of human cancer cells. In the preferred embodiment, the surface antigen will comprise the fusion protein (F-protein) of RSV.

Human disease conditions includes by way of example viral infections, e.g., RSV, papillomavirus, hepatitis, AIDS, etc., cancer, bacterial infections, yeast infections, parasite infection, e.g, malaria, etc. Essentially, human disease conditions are intended to embrace any human disease condition potentially preventable or treatable by the administration of human monoclonal antibodies specific to a particular antigen.

The subject method for producing human monoclonal antibodies essentially involves the combination of in vitro priming of naive human spleen cells, transferral of these spleen cells to immunocompromised donors, i.e., SCID mice, followed by antigen boosting of SCID mice which have been administered said spleen cells. It has been surprisingly discovered that the combination of these two known methods for producing human antibodies results in synergistic results. Specifically, it results in very enhanced antigen specific responses to the immunizing antigen as well as very high titers of human monoclonal antibodies of the IgG isotype. More specifically, it has been found that this combination results in unprecedented high secondary responses: the human IgG responses in the hu-SPL-SCID serum were 10-fold higher than those resulting from transfer of naive cells in SCID and specific antibody responses were 1000-fold increased. Also, the resulting antibodies are found to be of high affinity and specificity comparable to antibodies produced in experimentally hyperactive immune animals. It has also been found that when using naive spleen cells, to obtain such unexpected results it is necessary to challenge with antigen both in vitro and after introduction into the resultant hu-SPL-SCID mouse. Also, it is preferable but not essential to introduce additional fresh non-primed spleen cells to the hu-SPL-SCID donor just prior to antigen boosting. This has been found to result in still further enhancement of the antibody response.

The present invention was developed after an optimal in vitro primary and boosting protocol for the generation of secondary responses from naive human spleen cells had previously been disclosed Brams et al, *Hum. Antibod. Hybridomas* (1993), 4, 57–65. The protocol Brams et al, *Hum. Antibod. Hybridomas* (1993), 4, 57–65 was found to provide for antigen specific IgG responses about 2 to 10 times higher than obtained from cultures subjected to one antigen challenge. This in vitro immunization (IVI) protocol was developed and optimized using very different antigens, i.e., horse ferritin (HoF), calmodulin, prostate specific antigen (PSA), mouse IgG, transferrin, Keyhole Limpet Hemocyanine (KLH) di-nitro phenyl (DNP) bound to T-cell dependent protein carriers and RSV fusion (F) protein.

Essentially, this protocol involves restimulation of the spleen cell culture on day 1 after culturing is started with antigen together with autologous spleen cells in a 1:1 ratio. It has been demonstrated that the IgG responses measured using this protocol were the result of repeated antigen exposure, and are equivalent to secondary responses.

These experiments further demonstrated that intact spleens were the optimal source of lymphocytes, including trauma- and ITP spleens. By contrast, peripheral blood lymphocytes (PBLs), and cells from tonsils or lymph nodes proved to be inferior for induction of antigen-specific responses. Moreover, depletion or neutralization of any cellular component resulted in inferior responses Boerner et al, *J. Immunol.* (1991), 147:86–95. Also, these experiments indicated that for a given spleen cell preparation and antigen, that there exists a unique optimal antigen concentration.

Therefore, having established an optimal in vitro priming and boosting protocol for generation of secondary responses from naive human spleen cells; it was conceived to test this protocol in combination with previous in vivo methods for producing human monoclonal antibodies, i.e., the SCID mouse. It was unknown prior to testing what effect, if any, administration of antigen primed spleen cells would have on the resultant production of human monoclonal antibodies to a given antigen by the SCID mouse or the ability of human lymphocytes to be maintained therein. However, it was hoped that this would provide for enhanced antigen boost and enhanced expression of the in vitro antigen primed naive spleen cells.

In this regard, it has been previously reported that human lymphocytes can establish themselves and remain alive for several months in SCIDs McCune et al, *Science* (1988), 241, 1632–1639, Lubin et al, *Science* (1991), 252:427. However, as noted, surpa previous methods using SCIDs or human monoclonal antibodies to antigens have used cells from donors previously exposed to the antigen either naturally or by vaccination and have typically not resulted in high human antibody titers.

Quite surprisingly, it was found that combination of in vitro priming and boosting protocol for generation of secondary responses from human naive spleen cells Brams et al, *Hum. Antibod. Hybridomas* (1993), 4, 57–65 in the hu-SCID model resulted in synergistic results as evidenced by highly significant antigen specific IgG responses to the immunizing antigen.

Further, it was also discovered that the combination of these methods (using horse ferritin (HoF) as a model antigen) that:

(i) introduction of an in vitro immunization step prior to transfer into SCIDs is essential for reliably inducing significant antigen-specific responses;

(ii) human cells must be transferred into the peritoneum to achieve optimal maintenance of human splenocytes in the SCID mouse;

(iii) optimal in vitro cultivation is about three days;

(iv) use of IL-2 and optionally IL-4 or IL-6 in vitro results in highest antibody titers of antigen specific responses in the hu-SPL-SCID mice;

(v) the hu-SPL-SCID in mouse is preferably boosted with antigen emulsified in an adjuvant, e.g., Freunds Complete Adjuvant (FCA) and/or Alum;

(vi) killing or neutralization of NK cells, whether of murine or human origin surprisingly has no benefit on antibody production. However, it was found that use of the SCID-beige mouse, an NK low line, as the host for the in vitro primed cells, provides for a superior response when boosting is effected using a combination of adjuvants, i.e., FCA and Alum. (vii) spleens, but not lymph nodes of $\cong \frac{1}{3}$ of the hu-SPL-SCID mice were enlarged up to 25 times compared to normal SCIDs. Moreover, of these up to two-thirds of the cells in such spleens tested positive for normal human lymphocyte membrane markers.

More specifically, the subject method comprises priming naive human splenocytes in vitro, for about 1 to 10 days, preferably about 3 days with antigen, transferral of the primed cells to a SCID mouse, and subsequently boosting the mouse with antigen about 3 to 14 days later, preferably about 7 days later. This has been demonstrated to result in high antigen specific IgG responses in the sera of the resultant hu-SPL-SCID mouse from about day 24 onwards. Typically, the serum end-dilution titers are about $10^6$ (half maximal responses at approximately 50 mg IgG/ml) using a naive antigen, horse ferritin and $10^7$ (half maximal responses at approximately 5 mg IgG/ml) when a recall response is induced with a viral antigen, i.e., the fusion protein of RSV. It is expected based on these results that similar responses will be obtained using other antigens.

As noted, optimal induction of the desired antibody response requires antigen challenge of the human cells both in vitro and in vivo in the hu-SPL-SCID mouse. It was also found that IL-2 is necessary during in vitro priming, and that IL-4 and IL-6 administered concomitantly with IL-2 further enhanced responses in the hu-SPL-SCID mouse. Moreover, SCID reconstitution is facilitated but was not dependent on concomitant intraperitoneal administration of irradiated allogeneic lymphocytes.

It was further discovered that there was significant variation in the antibody responses from one spleen to another. For example, some spleens required concomitant administration of antigen and fresh autologous spleen cells on day 10 for generation of antigen specific antibody responses. Also, it was found that the level of antibody responses varied somewhat in different hu-SPL-SCID mice. However, based on the teachings in this application, one skilled in the art can readily select suitable conditions so as to produce an optimal antigen specific antibody response to a given antigen.

For example, by testing several different spleen preparations for their ability to produce specific antibody in culture, e.g., after ten days of in vitro immunization, one can identify the highest responder. Moreover, since large numbers of cells are prepared and frozen from each spleen, it is possible to set up a new in vitro immunization for three days from the selected spleen and follow up with transfer in SCID mice. By contrast, other cellular materials, e.g., peripheral blood cells are not amenable to such optimization, given the fairly limited amount of PBL's recoverable from one donor in a single transferral.

As previously noted, in contrast to previous reports, it was found that for the present method, when peripheral blood cells were used, neutralization of human NK activity had no effect on spleens. Moreover, neutralization of SCID NK cells with complement fixing anti-asialo GMI antibodies decreased antigen-specific IgG responses. By contrast, use of the SCID/beige mouse, a strain with reduced NK cell levels did provide for significantly increased antigen specific IgG responses compared to normal SCID.

Additionally, two immunization routes, intravenous (IV) and intraperitoneal (IP) were compared for their ability to provide for reconstitution of SCID mice, i.e., maintenance of spleen cells therein and the production of human antibodies. It was found that the peritoneum was the optimal site of cell transfer and immunization. Moreover, date, transfer of cells intravenously has never been found to result in repopulation when more than 0.01 μg/ml human IgG was detected in the mouse serum.

It was also found that the resultant IgG concentrations directly correlated with the number of transferred human cells. For example, repopulation of SCIDs was 92% when $5 \times 10^6$ in vitro primed spleen cells were injected intraperitoneally, and virtually 100% when $5 \times 10^7$ in vitro primed spleen cells were injected intraperitoneally. One skilled in the art can, based on the teachings in this application, select an optimal number of injected in vitro primed spleen cells. In general, this will range from about $10^4$ to about $10^8$ cells, more preferably about $10^6$ to $10^8$ cells, and most preferably at least about $10^7$ to $10^8$ cells.

It was also found that the antibody response is affected by the presence of the particular adjuvant. More specifically, it was observed that maximal human antibody responses were achieved when the hu-SPL-SCID mice were boosted with antigen emulsified in Complete Freund's adjuvant (CFA) or using CFA and Alum together. Tests in hu-SPC-SCID boosted with ferritin showed that CFA was a better adjuvant than Alum, eliciting 33 mg and 13 mg/ml human IgG respectively. Combination of CFA and Alum did not improve response in SCID. However, use of these adjuvants in SCID/beige-hu (which mice comprise a mutation resulting in reduced NK cell activity) results in 8–10 fold increase in IgG production compared to CFA alone. However, it is expected that other adjuvants, or combinations thereof, may also produce similar or even enhanced results. The highest total human IgG concentrate using Complete Freund's adjuvant and Alum together was about 10 mg/ml, and the specific highest IgG concentration was about 500 μg/ml monoclonal antibody equivalent.

Using this method with ferritin produced polyclonal antibody responses comparable to that obtained in hyperimmune goats, rabbits and pigs in terms of specificity, reactivity, and use of Ig chain isotypes. The hu-SPL-SCID serum antibodies were mostly IgG, bound only to cells from tissues high in ferritin, and not to cells from ferritin-low or ferritin-negative tissues, and recognized both natural ferritin as well as denatured ferritin in a Western blot. These results are extremely unexpected both in antibody concentration and the antigen specificity of human antibodies obtained. Moreover, similar results are obtained using different antigens.

After injection, it is found that human cells tend to accumulate at two sites, i.e., the peritoneum and the mouse spleen. While no more than about 7% of human cells were found in the blood, the lymph nodes and the liver were of human antigen, between 25% and 33% of the cells were of human origin in enlarged spleens and in the occasional tumors in some animals. These human cells were almost exclusively B and T-cells, with a small amount of $CD14^+$ cells, mostly monocytes, in the enlarged spleens.

These results were determined by flow cytometry investigating spleen, lymph nodes, liver and peritoneum. In those cases that the human splenocytes repopulated the spleen, it was found that the spleens were often enlarged, up to 25 times the size of native SCID spleens. The human cells constituted up to about 30% of the total number of cells in the spleen when measured immediately after extraction, with the remainder of unknown origin. However, after 3 days in culture, a majority of surviving cells were found to be of human origin as the cells bound antibodies and exhibited no cross reactivity with mouse lymphocytes.

It was further observed that the reconstituted mice could be divided into two groups, those with normal size spleens and those with enlarged spleens. Hu-SPL-SCID mice with enlarged spleens, i.e., 25 times normal size had human IgG levels approximately 150 times higher than those with normal spleens, and the level of antigen specific human IgG was approximately 10,000 higher in those with normal size spleens which were treated similarly. It was also found that the relative affinity of the antigen specific response increased throughout the response, indicating that a higher percentage of the total immunoglobulin pool was comprised of antibodies having better binding properties. These results indicate that the system is antigen driven.

These results are highly significant and indicate that it should generally be possible to rescue human cells from the hu-SPL-SCID and use same for generating combinatorial human antibody gene libraries thereby resulting in human monoclonal antibodies of high affmity and specificity that may be used clinically and/or diagnostically.

More specifically, the present invention provides novel human monoclonal antibodies to the RSV F-protein which exhibit high affinity to the RSV F-protein, i.e., $\leq 2 \times 10^{-9}$ molar protein and which human monoclonal antibodies are capable of neutralizing RSV in vitro. The present invention further provides methods for manufacture of such human monoclonal antibodies to the RSV F-protein.

In general, such human antibodies are produced by in vitro immunization of naive human splenocytes with RSV F-protein, transferral of such in vitro immunized human splenocytes into an immunocompromised animal donor, i.e., a SCID mouse, boosting said animal with RSV F-protein, and isolation of human B cells therefrom which secrete human monoclonal antibodies to the RSV F-protein, immunization of said human B cells, and cloning of said immunilized B cells to select cells which secrete human monoclonal antibodies having a high affinity to RSV F-protein, preferably at least $10^{-7}$ molar and more preferably $\leq 2 \times 10^{-9}$ molar.

As discussed, it has been discovered that the combination of in vitro immunization, in particular of human splenocytes, i.e., which have or have not been previously exposed to the RSV F-antigen and transferred to an immunocompromised animal donor, i.e., SCID mouse which is then boosted with RSV F-protein antigen affords significant advantages relative to conventional methods for making human antibodies in SCID mice. Namely, it provides for very high antibody titers, i.e., the highest anti-F protein titers being about $10^{-7}$, high IgG concentrations, i.e., about 3 mg/ml for the highest responders. Moreover, this method allows for the production of human antibodies having highly advantageous combinations of properties, i.e., which exhibit both high. affmity to the RSV F-protein and which moreover display substantial in vitro neutralizing activity.

As described in greater detail in the examples, the present inventors have isolated two human monoclonal antibodies, RF-1 which exhibits an affinity constant Ka to the F-protein, $Ka=10^{10}$ M when determined by plasmon resonance, and RF-2 which exhibits an affinity constant of $Ka=5\times10^8$ M when determined by titration microcolorimetry. Also, the calculated Kd of RF-2 was $2\times10^{-9}$ M. Moreover, both of these antibodies display in vitro virus neutralizing properties at concentrations of between 8 and 120 ng/ml as well as exhibiting an ability to inhibit the fusion of previously RSV infected cells. Significantly, this in vitro neutralization activity is applicable against a broad variety of different wild and laboratory RSV strains, both of the A and B virus types.

Given these results, i.e. the high affinity of the subject antibodies to the RSV F-protein, which comprises a surface protein expressed on the surface of RSV infected cells, as well as ability to effectively neutralize the virus, and to inhibit fusion of virally infected cells, the subject human monoclonal antibodies should be suitable both as therapeutic and prophylactic agents, i.e., for treating or preventing RSV infection in susceptible or RSV infected subjects. As noted, RSV infection is particularly prevalent in infants, as well as in immunocompromised persons. Therefore, the subject monoclonal antibodies will be particularly desirable for preventing or treating RSV infection in such subjects.

Moreover, given the human origin of the subject monoclonal antibodies, they are particularly suitable for passive immunotherapy. This is because they likely will not be subject to the potential constraints of murine monoclonal antibodies, i.e., HAMA responses and absence of normal human effector functions. In fact, based on the characterization of the subject human monoclonal antibodies (described in examples infra), it would appear that both RF-1 and RF-2 exhibit substantially greater in vitro neutralization activity and ability to inhibit fusion of previously infected RSV cells than previously disclosed murine or chimeric anti-F protein antibodies and human Fab fragments derived from recombinational libraries. Also, given their human origin it is expected that such neutralization activity will be maintained upon in vivo administration.

Another advantage of the subject human monoclonal antibodies is their substantial absence of reactivity with normal tissues. As shown infra, the subject human monoclonal antibodies bind only to RSV infected cells, not to cell lines representing lymphoid tissue, liver, prostrate or laryngeal epidermis. Therefore, these antibodies upon in vivo administration should efficiently bind to RSV infected cells and not to normal tissues and thereby should provide for neutralization of RSV infection. Further, based on the disclosed properties, it is expected that the subject human monoclonal antibodies to the RSV F-protein may be used to protect susceptible hosts against RSV infection.

More specifically, the subject human monoclonal antibodies to the RSV F-protein are produced by obtaining human splenocytes, e.g., from a trauma or ITP source, which are then primed in vitro. This essentially comprises culturing said naive human splenocytes in vitro in the presence of a sufficient amount of Il-2 and optionally RSV F-protein to induce immunization, also referred to as antigen priming. In general, the amount of RSV F-protein that may be used ranges from about 1 to 200 ng/ml RSV protein, more preferably 10 to 100 ng/ml, and most preferably about 40 ng/ml of RSV F-protein.

The in vitro culture medium will preferably also contain lymphokines, in particular IL-2 and optionally IL-4 and IL-6. The amount thereof will be amounts which provide for immunization and the desired production of antibody producing cells. For example, in the case of IL-2, an amount ranging from about 5 to 200 IU/ml, and more preferably from about 10 to 50 IU/ml, most preferably 25 IU/ml is suitable.

This culture medium will also contain other constituents necessary to maintain the viability of human splenocytes in culture, e.g., amino acids and serum. In the examples, a culture medium containing IMDM supplemented with 2 mM glutamine, 2 mM sodium pyruvate, non-essential amino acids, 25 IU/ml IL-2 and 20% fetal calf serum was used. However, one skilled in the art, based on the teachings in this application, can vary the culture medium using routine optimization.

The in vitro immunization step will be effected for a time sufficient to induce immunization. In general, the cells will be cultured in the presence of RSV F-protein from about 1 to 10 days and preferably for about 3 days. However, this will vary dependent, e.g., upon the particular spleen sample. Similarly, one skilled in the art, based on the teachings in this application and using known methods may determine a suitable duration for the in vitro immunization step.

The antigen used for the in vitro immunization will preferably be a purified RSV F-protein so as to ensure that the splenocytes are immunized against the F-protein and not against other useless (non-surface) antigens. Methods for obtaining purified RSV protein are known in the art. The present inventors in particular utilized the method of Walsh et al, *J. Gen Virol.*, 70, 2953–2961, 1989. However, the particular method is not critical provided that RSV F-protein of sufficient purity to obtain human monoclonal antibodies having specificity to the RSV F-protein are obtained. Alternatively, the RSV F-protein may be produced by recombinant methods as described in U.S. Pat. No. 5,288,630 issued on Feb. 22, 1994.

After in vitro immunization, the RSV F-protein immunized or primed naive human splenocytes are then introduced into an immunocompromised donor, i.e., a SCID mouse. This is preferably effected by intraperitoneally administering the RSV F-protein primed human splenocytes into SCID mice. The number of such splenocytes which is administered will typically vary from about $10^4$ to $10^8$ spleen cells, with about $10^7$ to $10^8$ spleen cells being preferred. The number of such cells is that which results in the desired reconstitution, i.e., SCID mice which produce recoverable concentrations of human antibodies specific to the RSV F-protein. Preferably, such spleen cells will be suspended in HBSS at a concentration of about $8\times10^8$ cells/ml prior to administration.

After intraperitoneal transferral of splenocytes, the SCID mice are then oosted with the RSV F-protein. This is effected at a time sufficiently proximate to he transferal of splenocytes such that the desired production of human anti-RSV F-protein antibodies is realized. In general, this may be effected 3 to 14 days after transferral, and optimally about 7 days after transferral. Preferably, said antigen administration will be effected intraperitoneally. The amount of RSV F-protein administered will range from about 1 to 50 μg and preferably about 1 to 10 μg. In the examples, 5 μg protein was administered. However, the amount and time of immunization may vary dependent upon the particular mouse, spleen sample, and purity of RSV F-protein.

Preferably, antigen boosting will be effected in the presence of an adjuvant, e.g., Complete Freund's Adjuvant, Alum, Saponin, etc., with Complete Freund's Adjuvant (CFA) and Alum being preferred. However, it is expected that other known adjuvants may be substituted to obtain substantially equivalent or even enhanced results.

After antigen boosting, the SCID mice are then bled, e.g., tail bled, and their serum tested for human IgG concentration and anti-F protein antibody titers. Those animals which exhibit the highest antibody titers and concentration are then used for recovery of human IgG secreting cells.

It has been discovered that SCID mice having the highest anti-F human antibody titers developed large abdominal tumors which provide a good source of human antibody secreting cells. Preferably, these tumors are recovered by excision under sterile conditions, single cell suspensions are prepared, and the cells are then washed and cultured. In the examples, the cells are washed with IMDM containing 2% fetal calf serum, and the cells cultured in suspension of $10^6$ cells/ml in T-25 flasks containing IMDM with 10% FCS. However, such culturing conditions may be varied by one skilled in the art.

These cells are then immortalized preferably using EBV. Immortalized cells which secrete anti-F protein antibodies are then identified by known methods, e.g., ELISA. As noted, this method has been demonstrated to result in the identification of two distinct human monoclonal antibodies which specifically bind RSV F-protein, i.e. RF-1 and RF-2. However, based on the teachings in their application, in particular the examples, other human monoclonal antibodies to the RSV F-protein having similar properties may be obtained by one skilled in the art absent undue experimentation. These antibodies are distinct given the fact that most were generated in two different experiments, using different SCID mice. The cell lines which express RF-1 and RF-2 have been maintained in culture for prolonged time, i.e., about 18 and 16 months respectively; dividing with an approximate doubling time of about 36–48 hours. The specific antibody concentration is on average about 0.8–1 μg/ml in a culture seeded at $0.5 \times 10^6$ cells/ml grown for three days.

As discussed in greater detail infra, both RF-1 and RF-2 are IgG (1, k) with half-maximal binding to F-protein in ELISA at 0.6 and 1 ng/ml respectively, and exhibiting isoelectric points of about 8.8 and 8.9 respectively.

Moreover, these antibodies exhibit high affinity to the RSV F-protein. Specifically, for RF-1 the dissociation constant for RF-1 as determined by plasmon resonance on an IASYS machine is about $10^{-10}$ M. The Ka constant for RF-2 is similarly high; when determined by titration microcolorimetry according to Wiseman et al. (1989) and Robert et al. (1989) it is about $2 \times 10^{-9}$ M.

Additionally, these antibodies have been demonstrated to effectively bind RSV infected cells, while not binding normal human cells tested, e.g., respiratory tract lining (HEp-2, a laryngeal epidermoid carcinoma, CCL 23), liver (HepG2, a human hepatoma cell line, HB 8068), lymphoid tissue, SB, a human B lymphoblastoid cell line, cat. no. CCL 120 and HSB, a T lymphoblastoid line, cat. no. CCL 120.1, and prostrate (LNCaP.FGC, a human prostrate adenocarcinoma line, cat. no. CRL 1740).

Significantly, both RF-1 and RF-2 both have been shown to exhibit substantial in vitro RSV viral neutralization. This was demonstrated in two different assays (described in greater detail infra), i.e., an infection neutralization assay effected by pre-reacting the virus with purified monoclonal antibody prior to its addition to cells (which measures ability of antibody to inhibit virus infectivity) and a fusion inhibition assay which measures the ability of the monoclonal antibody to inhibit virus growth and expansion after virus entry into the cell.

Moreover, as discussed in greater detail infra, both RF-1 and RF-2 inhibited virus infection of twelve different isolates at concentrations respectively ranging from about 30 ng/ml to 1000 ng/ml. Thus, RF-2 apparently performs better than RF-1, yielding to 50% virus inhibition (ED50) at concentrations which are about 1.25 to 10 times lower than RF-1.

By contrast, higher concentrations of monoclonal antibody are required to inhibit fusion and viral antigen expression in previously infected cells, with RF-1 being about 5 to 10 times more potent than RF-2. Moreover, both RF-1 and RF-2 were effective against a Type B RSV, Type B prototype RS 6556, and a Type A RSV, Type A prototype RS Long. Thus, the in vitro results indicate that the subject human monoclonal antibodies may be used to treat or prevent RSV infection caused by different RSV strains, both of Type A and Type B prototype. As discussed previously, the RSV F-protein is fairly well conserved in different RSV isolates. Therefore, it is likely that the subject monoclonal antibodies to the RSV F-protein bind to a conserved epitope of RSV F-protein.

Figure 2A:
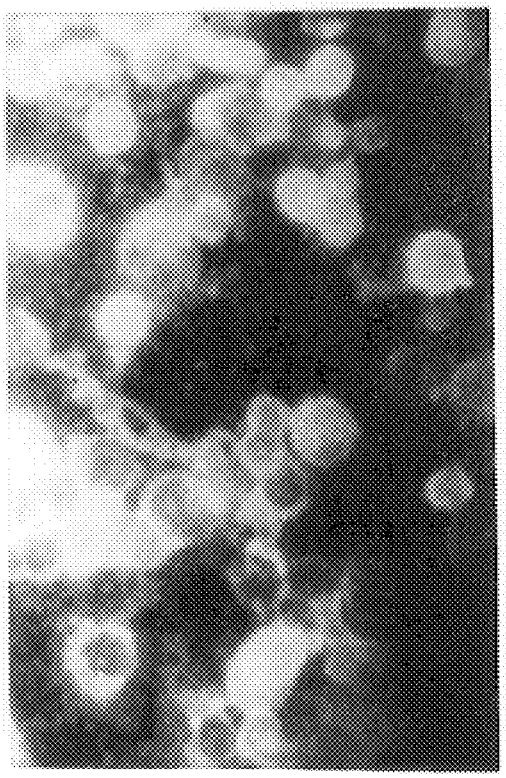
FIGS. 2A and 2B depict immunofluorescence of uninfected and RSV infected HEP-2 cells, respectively, with hu-SPL-SCID sera anti-F protein. Uninfected and RSV-infected HEp-2 cells were reacted with serum from hu-SPL-SCID mouse #6 diluted 1:50 taken 15 days after boost. Binding was revealed GAH IgG-FITC.
Figure 2B:
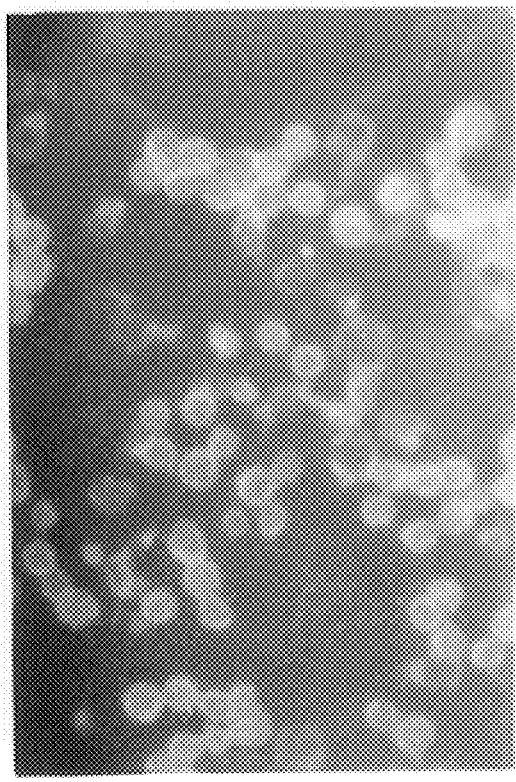

As discussed, the subject human monoclonal antibodies or recombinant human antibodies containing the variable heavy and light sequences therefrom (preparation discussed infra) will be used as therapeutic and prophylactic agents to treat or prevent RSV infection by passive antibody therapy. In particular, the DNA sequence encoding these DNA variable domains may be incorporated in IDEC's proprietary expression vector which is depicted in FIG. 2. This version is substantially described in commonly assigned U.S. Pat. No. 5,658,570 which issued on Aug. 19, 1997 and is herein incorporated by reference. This vector constant human constant domain, for example, human gamma 1, human gamma 4 or a mutated form thereof referred to as gamma 4 PE. (See U.S. Ser. No. 08/379,072, incorporated by reference herein.) In general, this will comprise administering a therapeutically or prophylactically effective amount of the subject human monoclonal antibodies to a susceptible subject or one exhibiting RSV infection. A dosage effective amount will preferably range from about 50 to 20,000 μg/Kg, more preferably from about 100 to 5000 μg/Kg. However, suitable dosages will vary dependent on factors such as the condition of the treated host, weight, etc. Suitable effective dosages may be determined by those skilled in the art.

The subject human monoclonal antibodies may be administered by any mode of administration suitable for administering antibodies. Typically, the subject antibodies will be administered by injection, e.g., intravenous, intramuscular, or intraperitoneal injection, or more preferably by aerosol. As previously noted, aerosol administration is particularly preferred if the subjects treated comprise newborn infants.

Formulation of antibodies in pharmaceutically acceptable form may be effected by known methods, using known pharmaceutical carriers and excipients. Suitable carriers and excipients include by way of example buffered saline, bovine serum albumin, etc.

Moreover, the subject antibodies, given their high specificity and affinity to RSV infected cells possess utility as immunoprobes for diagnosis of RSV infection. This will generally comprise taking a sample, e.g. respiratory fluid, of a person suspected of having RSV infection and incubating the sample with the subject human monoclonal antibodies to detect the presence of RSV infected cells.

This will involve directly or indirectly labeling the subject human antibodies with a reporter molecule which provides for detection of human monoclonal antibody-RSV immune complexes. Examples of known labels include by way of example enzymes, e.g. β-lactamase, luciferase, etc. and radiolabels.

Methods for effecting immunodetection of antigens using monoclonal antibodies are well known in the art. Also, the subject anti-RSV F-protein antibodies in combination with a diagnostically effective amount of a suitable reporter molecule may be formulated as a test kit for detection of RSV infection.

MATERIALS AND METHODS

The following Materials and Methods were used in Examples 1 to 6.

F protein preparation and purification

F protein was prepared essentially according to the method of Walsh et al. *J. Gen. Virol*, 70, 2953–2961, (1989). Briefly, HEp-2 cells at 70% confluency were infected with the Long strain of RSV, a lab adapted strain of the A type. After culture for 48 hours in T-150 culture flasks in IMDM supplemented with 5% fetal calf serum, 2 mM glutamine and 2 mM sodium pyruvate, the cells were lysed in a lysing buffer of PBS containing 1% Triton X-100 and 1% deoxycholate. F protein was purified from the crude cell lysate on an affinity column of Sephadex coupled to a murine monoclonal anti-F antibody, B4 (a kind gift from Hiroyki Tsutsumi) (Tsutsumi et al. 1987). The column was washed extensively with lysing buffer and purified F protein was eluted in 0.1 M glycine pH 2.5, containing 0.1% deoxycholate. The eluate was neutralized immediately with 1 M Tris, pH 8.5 and dialyzed against PBS. After the detergent was removed on a Extracti-D gel column (Pierce, Rockford, Ill., Cat. No. 20346), F protein concentration was determined by EIA and the solution was sterilized by gamma irradiation.

Lymphoid cell preparation

Spleen was obtained following clinically indicated splenectomy of an idiopathic trombopenic purpura (ITP) patient. A single cell suspension was prepared by sieving through a metal mesh, and washed in IMDM media supplemented with 2% fetal calf serum. Red blood cells were eliminated by treatment with ammonium chloride lysing buffer for 90 seconds at 37° C. The white blood cell enriched suspension was then washed twice with serum containing media, resuspended in ice cold freezing media (95% FCS with 5% DMSO) at 108 cells/ml and frozen in liquid nitrogen until use.

In vitro immunization (IVI)

Cultures were set-up in IMDM supplemented with 2 mM glutamine, 2 mM sodium pyruvate, non-essential amino acids, 25 $\mu$g/ml IL-2 and 10% fetal calf serum. An antibiotics cocktail was added including 2.5 $\mu$g/ml amphotericin, 100 $\mu$g/ml ampicillin, 100 $\mu$g/ml kanamycin, 50 $\mu$g/ml chlortetracycline, 50 $\mu$g/ml neomycin and 50 $\mu$g/ml gentamicin. The cells were cultured in 6-well clusters at $3\times10^6$ cells/ml with 40 ng/ml F protein. After three days, the cells were collected, washed and resuspended in HBSS at $8\times10^8$ cells/ml for SCID reconstitution.

Reconstitution of SCID mice

Five to eight week old female CB17/SCID mice were reconstituted by intraperitoneal injection of 200 $\mu$l of HBSS containing $4\times10^7$ human spleen cells subjected to IVI; the mice were boosted one week later ip with 5 $\mu$g F protein in CFA and tail bled after another 15 days. Their serum was tested for human IgG concentration and anti-F protein antibody titer.

Recovery of human cells from hu/SCID mice

Two hu-SPL-SCID mice with high anti-F human antibody titers developed large abdominal tumors. Tumors were recovered by excision from sacrificed mice under sterile conditions, single cell suspensions were prepared, the cells were washed with IMDM containing 2% fetal calf serum and cultured at $10^6$/cells ml in T-25 flasks in IMDM with 10% FCS.

Testing for human IgG and anti-F protein antibodies

The testing for human IgG and anti-F antibodies was performed in ELISA. For that purpose, plates were coated overnight with GAH-Ig (0.05 $\mu$g/well) or F protein (0.05 $\mu$g/well) respectively in 0.1 M bicarbonate buffer, pH 9.5 and blocked with PBS containing 1% fetal calf serum. Serial dilutions of mouse sera, culture supernatants or purified antibodies were reacted to the plate. Bound human IgG were revealed by the subsequent addition of GAH IgG- HRP and OPD substrate (Sigma, ..., ...). Selected high titer human serum was used as a positive control in both assays and purified polyclonal human IgG, or (γ, K) myeloma protein were used as a standard in the estimation of the concentration of human IgG and monoclonal antibodies respectively.

Isotyping of human antibodies

Isotyping was performed in ELISA on F protein coated plates as described above. Bound human IgG were revealed by the subsequent addition of HRP conjugated mouse monoclonal antibodies specific for human γ1, γ2, γ3, γ4, $\mu$, κ and λ chains. Positive controls were run with myeloma proteins of the (γ1, κ), (γ2, κ), (γ3, λ), (γ4, λ) or (λ, λ) isotype and free κ and λ chains.

Protein A purification

Antibodies were purified from culture supernatants on a protein A- Sepharose 4B column. Briefly, supernatants were collected, filtered through 0.2 mm filters and supplemented with 0.02% sodium azide. Columns (gel volume approximately 0.5 ml) were equilibrated in PBS with 0.02% sodium azide, then loaded with supernatant at low speed. After extensive washing, bound human monoclonal IgG were eluted in 0.1 M sodium citrate buffer, pH 3.5, dialyzed against PBS-azide using Centricon 10 filters (Amicon,) and sterilized by gamma irradiation until further use. Columns were regenerated with citric acid pH 2.5 and re-equilibrated with PBS with 0.02% sodium azide for subsequent use.

Isoelectric focusing

Isoelectric focusing (IEF) of human antibodies was performed in polyacrylamide pre casted gels (Pharmacia, Uppsala, Sweden, Cat. No. 80-1124-80), pH 3- pH 10. Briefly, 20 $\mu$l of samples were loaded and run at 1500 volts for 90 minutes. Standards of pi 5.8 to 10.25 were used for pi reference. Gels were stained in Coomassie blue stain and destained in destaining buffer containing 25% methanol, 68% water and 8% acetic acid.

Western Blot

Purified F protein, both native and denatured by boiling, was migrated in a 10% polyacrylamide gel. The gel was blotted on a nitrocellulose sheet at 30 volts for 2 hours and 60 volts overnight. After transfer, the nitrocellulose was blocked for 1 hour at room temperature with 1% BSA and 0.1% Tween-20 in PBS. Different strips were washed in PBS and the primary antibodies, hu-SPL-SCID anti-F protein sera, or hu-SPL-SCID anti-tetanus toxoid negative control, or mouse anti-F protein positive control, were added for 1 hour. All sera were diluted 1:500. After extensive wash with PBS, the secondary antibody, GAH IgG- HRP for the samples and the negative control, or GAM IgG for the positive control, was added for 1 hour. Blots were revealed with 4-chloro-1-naphtol.

Immunofluorescence

RSV infected HEp-2 cells ($4 \times 10^4$) were fixed on glass slides using ice cold acetone and were reacted with 20 µl of serum diluted 1:10 or purified MAb, 2 µg/ml, for 1 hour at 37° C. The slides were washed and the bound antibodies were revealed with GAH IgG-FITC, for 30 minutes at 37° C. and observed under a fluorescence microscope.

FACScan analysis

RSV-infected HEp-2 cells ($10^6$ cells/sample) were washed with washing buffer (PBS with sodium azide 0.1%). The cell pellet was resuspended in 50 µl of incubation buffer (PBS with sodium azide 0.1% supplemented with BSA 0.1%) containing 2 µg/ml RF-1 or RF-2. After 15 minutes incubation on ice, the cells were washed and resuspended in incubation buffer containing GAH IgG-FITC for another 15 minutes on ice. After 3 washes, the cells were fixed in 1 ml PBS with 1% formaldehyde and analyzed in a Becton-Dickinson FACScan apparatus.

Affinity determination

Two methods were used to determine the affinity of human MAbs to soluble F protein:

In plasmon resonance, using an IASYS machine, antibody was bound covalently to the wet side of a device from which the change in mass can be determined based on the change of refraction of light shone on the dry side of the device. Different concentrations of F-protein were added and subsequently eluted off with a steady flow of PBS. The change in mass as a result of F-protein release from the antibody was measured, and from the kinetics a $K_{off}$ was determined. Ka was calculated by testing the off-rate from different levels of initial saturation.

Alternatively, affinity constant was determined by microcalotimetry according to Wiseman et al and Robert et al., as follows: RF-2 and F protein were co-incubated at a known concentration in a thermo-chamber at 42° C. and the enthalpy change due to the immune complex formation in the solution was measured. The reaction was repeated at 50° C. The binding association constant K was calculated as a function of temperature and enthalpy change according to Robert et al. in the following equation:

$$K = Kobs.e^{\Delta Hobs/R.(1/T-1/Tobs)}.e^{\Delta CTobs/R.(1/T-1/TTobs)}.(T/Tobs)^{\Delta C/R}$$

where Kobs is the binding equilibrium constant and $\Delta H^{obs}$ is the enthalpy change observed experimentally, at a given absolute temperature, Tobs; R is the universal gas constant (1.987) and $\Delta C$ is the experimentally determined binding heat capacity change.

Complement-enhanced virus neutralization assay

Two laboratory strains (Long, type A and 18537, type B) and ten wild type RS virus isolates, which were isolated from hospitalized infants, were used to assess the neutralizing capacity of anti-F protein human MAbs. Serial dilutions of human MAb were pre incubated with virus (50–100 pfu) in the presence of complement for 30 minutes at room temperature, in 100 µl IMDM/well of microtitration plate. HEp-2 cells ($5 \times 10^4$/well) were added in 100 µl MEM and incubated for 3 days at 37° C., 5% $CO_2$. The plates were washed, fixed with acetone and air dried and RSV antigen was detected by ELISA using mouse MAbs. The neutralization end point was determined arbitrarily as the dilution which reduced antigen production by 50% compared to control wells with no antibody.

Virus fusion inhibition assay

Fusion inhibition titers were determined by pre incubating 100 $TCID_{50}$ RSV Long (prototype A virus) or RS 6556 (Type B clinical isolate) with VERO cells ($5 \times 10^3$/well) in microtitration plates, for 4 hours at 37° C., 5% CO2. Various concentrations of human monoclonal antibodies or controls were added to each well and quadruplicate cultures were incubated for 6 days at 37° C., 5% $CO_2$. Control cultures contained virus non infected cells (negative) or infected cells in the absence of antibody (positive). Virus growth was detected in ELISA using rabbit polyclonal anti-F protein antisera and HRP-labelled anti-rabbit IgG. The reaction was developed with TMBlue substrate (KPI, Gaithersburg, MD). Titers (ED50) were defined as the concentration of antibody inhibiting virus growth by 50% based on regression analysis of the MAb dose response.

EXAMPLE 1

HU-SPL-SCID titers

Fifteen SCID mice received human spleen cells from a single donor with ITP condition. The cells were previously cultured for three days in the presence of IL-2 and different concentrations of soluble F protein. All animals were successfully reconstituted and, after boost with F protein, total human IgG concentrations varied from 12 µg/ml to 10 mg/ml in the serum and anti-F protein titers varied from $3 \times 10^2$ to $10^6$ (Table I). No correlation was observed between in vitro F protein exposure and anti-F protein titer in vivo. It has been previously observed with the subject method, in the horse ferritin antigen system, that antigen exposure is necessary during in vitro cultivation of the spleen cells to subsequently ensure specific antibody titer in vivo. The discrepancy between these two systems may be attributed to the difference in the antigens involved: since humans are not naturally exposed to horse ferritin, the IVI step involves an antigen priming of the spleen cells and induces a primary response in vitro; on the other hand, virtually all humans are immune to RSV through natural infection in early life, which leads to a permanent memory to F protein, therefore stimulation with IL-2 alone in vitro followed by one boost in vivo is enough to induce secondary responses.

The antisera were polyclonal, as judged from isoelectric focusing patterns (data not shown). They were tested for reactivity to F protein in Western blot. Our results showed that polyclonal human Abs did recognize soluble native F protein both in its dimer form (140 KD) and its monomer form (70 KD); they also reacted strongly with denatured F protein, binding specifically to the 2 subunits of 48 KD and 23 KD (representative data in FIG. 1). This suggests that at least a fraction of the humoral response to F protein is directed against linear, non conformational epitopes of the molecule. Immunofluorescence studies further demonstrated the specificity of the hu-SPL-SCID sera, since immune sera, but not naive SCID mouse sera, reacted strongly with RSV-infected HEp-2 cells (FIG. 2). No reactivity was observed towards non-infected HEp-2 cells used as negative control. It was concluded therefore that soluble F protein was an adequate antigen for the generation of antibodies specific to the membrane viral antigen expressed on naturally infected cells.

EXAMPLE 2

Identification of antibodies in tumor cell cultures

All mice with high anti-F protein titers were sacrificed and human cells were harvested from peritoneal lavage and spleens. Two mice (hu-SPL-SCID #6 and hu-SPL-SCID #15) spontaneously developed abdominal solid tumors that were recovered and teased into single cell suspension. The tumor cells secreted specific anti-F protein antibodies as determined in ELISA. These tumors and antibodies are referred to as RF-1 (RSV F-protein) and RF-2. RF-1 and RF-2 were generated in two different experiments separated by approximately two months and were isolated from individual hu-SPL-SCID mice, and are thus distinct antibodies; they have established themselves in culture for more than 18 months and 16 months respectively, dividing with an approximate doubling time of 36–48 hours. Specific antibody concentration is typically of 0.5–1 µg/ml in a culture seeded at $0.5 \times 10^6$ cells/ml and grown for three days.

Figure 3:
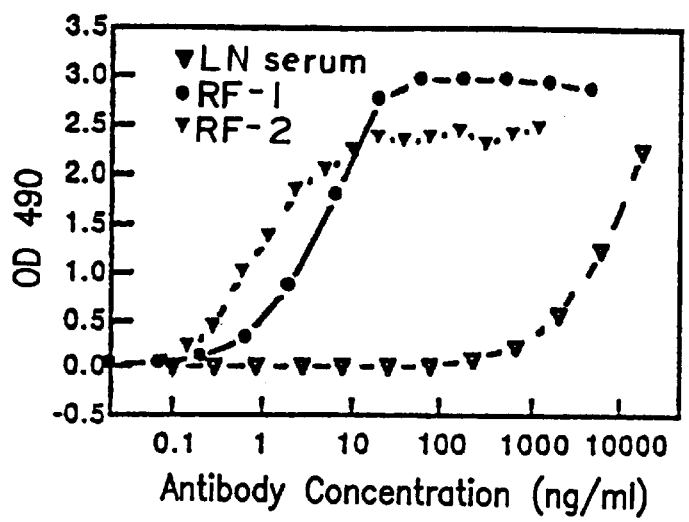
FIG. 3 depicts the reactivity of purified RF-1 and RF-2 to plastic bound affinity purified RSV F-protein. The reactivity of a reference human anti-RSV serum, LN, is also recorded. The ELISA plate was coated with 50 ng RSV F-protein.
Figure 5:
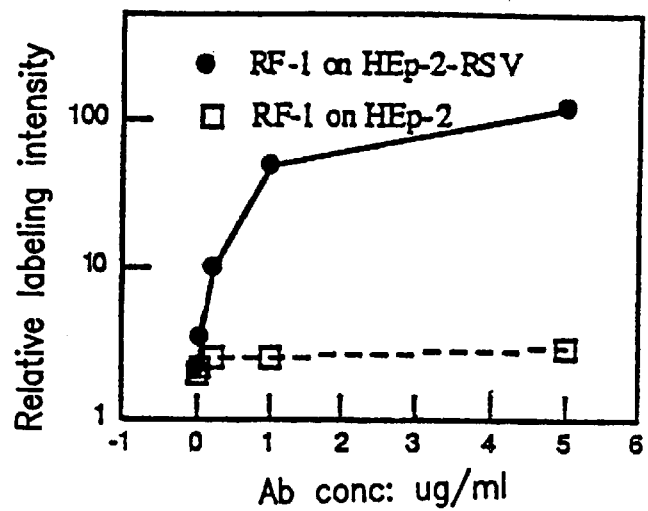
FIG. 5 depicts indirect Immunofluorescence flow cytometry assay of HEp-2 cells and HEp-2-cells infected with RSV, $1 \times 10^6$, incubated with various amounts of RF-1 and subsequently with a FITC-labeled GAH IgG. The relative average intensity of the entire population is recorded.
Figure 4:
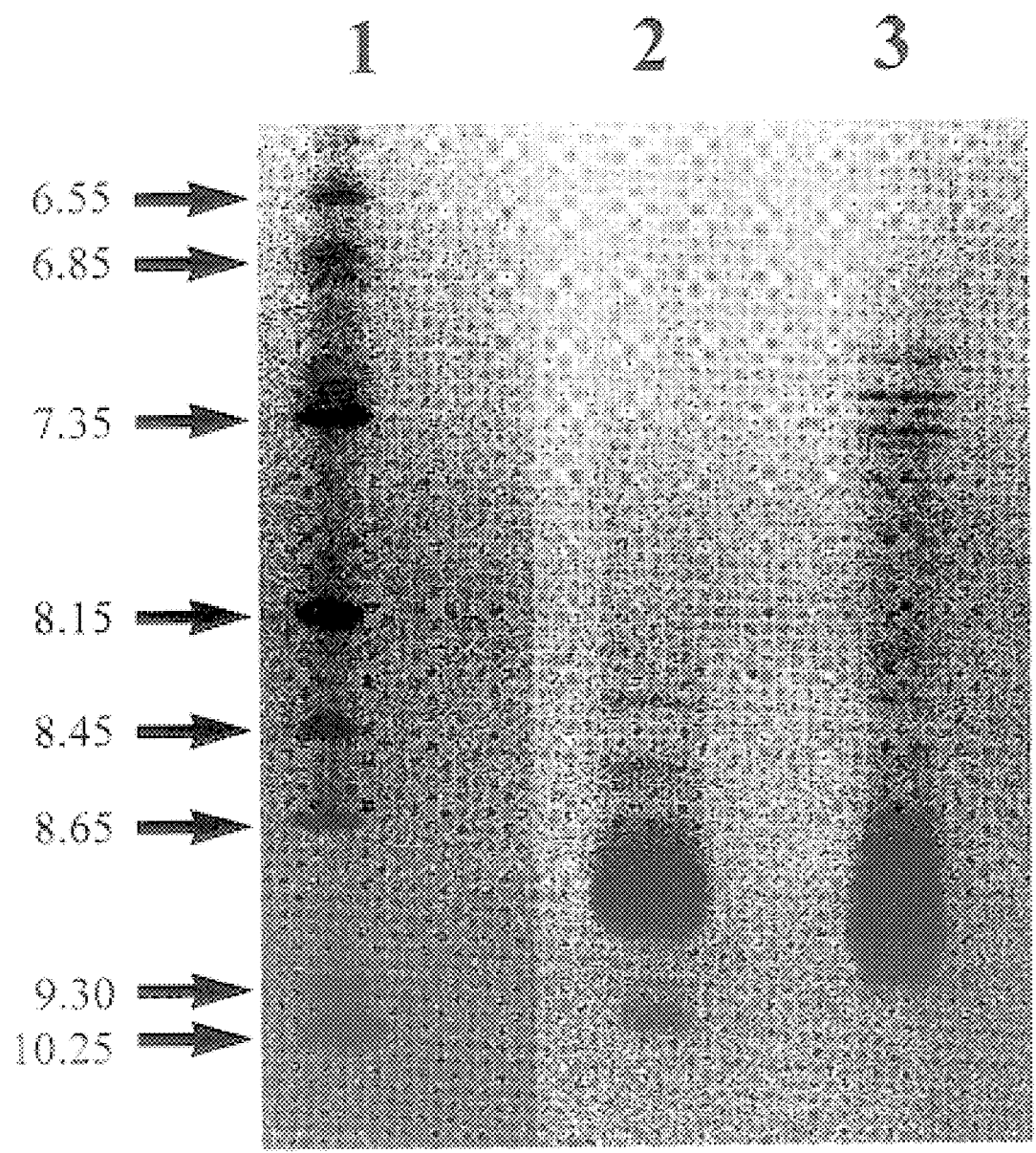
FIG. 4 depicts IEF of RF-1 (lane 2) and RF-2 (lane 3) human MAb purified from tumor cell supernatants. IEF was performed on a pH gradient of 3–10. Lane 1 represents the pi standards.

For further characterization, both human MAbs were purified from culture supernatants by affinity chromatography, using Protein A Sepharose columns. Both RF-1 and RF-2 are $IgG_{(1,k)}$ with half maximal binding to F-protein in ELISA at 0.6 and 1 ng/ml respectively (FIG. 3). From the migration pattern in IEF, RF-1 and RF-2 isoelectric points were determined to be 8.8 and 8.9 respectively (FIG. 4). RF-1 and RF-2 specifically recognized RSV infected HEp-2 cells in flow cytometry (FIG. 5). The dissociation constant, Kd, for RF-1 was determined by plasmon resonance on an IASYS machine to be in the $10^{-1}$ M range. The Kd constant of RF-2 was determined by titration micro calorimetry, according to Wiseman et al (1989) and Robert et al, (1989) to be $2 \times 10^{-9}$ M.

EXAMPLE 3

Tissue specificity of anti-F-protein

Purified antibodies were screened for reactivity to a series of human cell lines available at ATCC by means of indirect immunofluorescence assays measured by flow cytometry (Table II): The results showed that the antibodies did not bind to cell lines representing respiratory tract lining (HEp-2, a laryngeal epidermoid carcinoma, Cat. No. CCL 23), liver (HepG2, a human hepatoma cell line, Cat. No. HB 8065), lymphoid tissue (SB, a human B lymphoblastoid cell line, Cat. No. CCL 120 and HSB, a T lymphoblastoid line, cat. no. CCL 120.1) and prostate (LNCaP.FGC, a human prostate adenocarcinoma line, Cat. No. CRL 1740).

EXAMPLE 4

In vitro functional activity

To determine whether the antibodies had virus neutralizing effect in vitro, they were subjected to two types of functional assays: Infection neutralization assays were performed by pre-reacting the virus with purified MAb prior to its addition to the cells and therefore reflect the ability of the MAb to inhibit virus infectivity; fusion inhibition reflects the ability of the Ab to inhibit virus growth and expansion after virus entry in the cell. The outcome of both assays was measured as the amount of virus released in the culture after a given incubation time, as determined by viral antigen titration in EIA.

Both Abs were able to inhibit virus infection, of all twelve isolates tested, at concentrations ranging from 30 ng/ml to 1000 ng/ml and from 8 ng/ml to 165 ng/ml, for RF-1 and RF-2 respectively. RF-2 performed consistently better than RF-1, yielding to 50% virus inhibition (ED50) at concentrations 1.25 to 10 times lower than RF-1. Representative data are indicated in Table III.

As expected, higher concentrations of MAb were required to inhibit fusion and viral antigen expression in previously infected cells. In this assay, RF-1 was 5 to 10 times more potent than RF-2. Both MAb were more effective in the Type B prototype RS 6556 than in the Type A prototype RS Long (Table III).

TABLE I

| mouse # | [Ag] in vitro | fresh cells | hu IgG (µg/ml) | anti-F titer |
| --- | --- | --- | --- | --- |
| 1 | 1 µg/ml | + | 1,000 | $10^6$ |
| 2 | 1 µg/ml | + | 12.3 | $10^3$ |
| 3 | 1 µg/ml | + | 3,000 | $10^6$ |
| 4 | 1 µg/ml | + | 8,750 | $10^6$ |
| 5 | 1 µg/ml | + | 1,000 | $10^6$ |
| 6 | 1 µg/ml | − | 1,500 | $10^5$ |
| 7 | 1 µg/ml | − | 162 | $10^5$ |
| 8 | 1 µg/ml | − | 4,500 | $10^6$ |
| 9 | 1 µg/ml | − | 333 | $10^5$ |
| 10 | 40 ng/ml | − | 3,300 | $5 \times 10^5$ |
| 11 | 40 ng/ml | − | 554 | $3 \times 10^2$ |
| 12 | 1 µg/ml | − | 10,000 | $5 \times 10^5$ |
| 13 | 1 µg/ml | − | 200 | $5 \times 10^4$ |
| 14 | 0 µg/ml | − | 182 | $5 \times 10^4$ |
| 15 | 0 µg/ml | − | 3,300 | $10^5$ |

Table I: Splenocytes from a single donor were cultured in the presence of IL-2 for 3 days, with or without F protein. SCID mice were reconstituted with $4 \times 10^7$ cells and boosted with 10 µg of F protein ip in CFA. In mice # 1, 2, 3, 4 and 5, fresh autologous cells ($20 \times 10^6$) were injected with the boost. Human IgG concentration was determined by comparison to a standard curve of polyclonal IgG and anti-F protein titerwas determined by end point dilution in EIA.

TABLE II

| Cell line | Tissue Type | Tissue Labeling |
| --- | --- | --- |
| HEp-2 | Laryngeal epidermis | − |
| RSV infected- HEp-2 | Laryngeal epidermis (RSV) | ++++ |
| SB | Lymphoid | − |
| HSB | Lymphoid | − |
| LNCaP | Prostate | − |
| HepG2 | Liver | − |

Table II: Reactivity of RF-2 with various cell lines. Various cell lines were subjected to indirect immunofluorescence labeling with RF-2, 200 ng/$10^6$ cells. A Fab goat anti-human IgG-FITC was used as second step. (−) indicates the presence of RF-2 did not result in change of channel for the average fluorescence; (+) indicated increase of average labeling by 0.5 log.

TABLE III

| | Fusion Inhibition activity $ED_{50}$ titer | | | Infection Neutralization Activity $ED_{50}$ titer | |
| --- | --- | --- | --- | --- | --- |
| Antibody | RS Long (Type A) | RS 6556 (Type B) | Antibody | MR 144 (Type A) | 18537 (Type B) |
| RF-1 | 660 ng/ml | 40 ng/ml | RF-1 | 30 ng/ml | 30 ng/ml |
| RF-2 | 3300 ng/ml | 400 ng/ml | RF-2 | 8 ng/ml | 12 ng/ml |

Table III: $ED_{50}$ is defined as concentration of antibody inhibiting virus growth by 50% based on regression analysis of the monoclonal antibody dose-response.

EXAMPLE 5 (COMPARATIVE)

Induction of IgG Recall Responses to F-protein in vitro

More than 95% of the population over 2 years of age have been exposed to, and responded successfully to RSV Henderson et al, J. Med. (1979), 300, 530–534. Challenge of spleen cell in vitro with RSV F-protein should, therefore, result in recall responses, and, indeed, mainly IgG responses were induced in vitro with spleen cells (see FIG. 5). The optimal antigen concentration, 40 ng/ml, was at least one order of magnitude lower than what was observed for antigens inducing primary responses, i.e. ferritin, 1lig/ml, Boerner et al, *J. Immunol.*, 1991, 147, 86–95; Brams et al, *Hum. Antibod. Hybridomas*, 1993, 4, 47–56. Therefore, it must be considered that in vitro priming with F-protein induces secondary like responses. Several attempts to induce significant in vitro responses to RSV F-protein failed with PBMCs and tonsil derived cells.

A limited effort to generate monoclonal antibodies from in vitro primed spleen cells resulted in several monoclonal IgG antibodies to RSV F-protein. Most of these, however, cross-reacted to one of several control antigens in ELISA (results not shown).

EXAMPLE 6

Cloning of the genes coding for RF-2

Neither the RF-1 nor the RF-2 clone produce significant amounts of antibody. Also, both of these cell lines grow best in media with 20% FCS, which is disadvantageous because it results in contamination of the purified antibody with bovine IgG. Therefore, in order to be able to produce and purify amounts of antibody necessary for doing meaningful animal model tests, which typically requires UP to 1 gram of one selected antibody, it is advantageous to transfer the genes coding for RF-1 and RF-2 to a production vector and cell line. IDEC Pharmaceuticals, Inc., has developed a very efficient eukaryotic production system which results in the production of human monoclonal antibodies in CHO cells. This vector system is described in commonly assigned U.S. Pat. No. 5,658,570, which issued on Aug. 19, 1997 and in commonly assigned U.S. Ser. No. 08/149,099, allowed Jun. 12, 1997, both of which are incorporated by reference herein. Routinely using this system antibody gene transfected CHO cells produce around 200 mg antibody per liter of serum free medium in spinner cultures and greater than 500 mg/liter in fermentors after amplification in methotrexate.

Cell culture cloned (see below) RF-2 cells, approximately $5 \times 10^6$, were subjected to RNA extraction using a mRNA isolation kit, FAST TRACT (InVitroGen, San Diego, Calif.), and single stranded cDNA was prepared using an oligo-dT primer and reverse transcriptase. An aliquot of cDNA was used as the starting material for polymerase chain reaction (PCR) amplification of the variable region genes. PCR was performed using two sets of primers. (SEQ ID NO: 1–5) (see Table IV).

TABLE IV*

Heavy chain primers with Mlu 1 site $V_H1$    5' (AG)$_{10}$ <u>ACGCGT</u>G(T/C)CCA(G/C)TCCCAGGT(G/C)CAGCTGGTG 3'
$V_H2$    5 (AG)$_{10}$ <u>ACGCGT</u>GTC(T/C)TGTCCCAGGT(A/G)CAG(C/T)TG(C/A)AG 3'
$V_H3$    5 (AG)$_{10}$ <u>ACGCGT</u>GTCCAGTGTGAGGTGCAGCTG 3'
$V_H4$    5 (AG)$_{10}$ <u>ACGCGT</u>GTCCTGTCCCAGGTGCAG 3'
$V_H5$    5 (AG)$_{10}$ <u>ACGCGT</u>GTCTGGCCGAAGTGCAGCTGGTG 3'

Heavy chain constant region primer (SEQ ID NO.6) anti-sense strand with Nhe 1 site IgG1-4 (AG)$_{10}$GCCCTTGGT<u>GCTAGC</u>TGAGGAGACGG 3'

Kappa Chain primers (SEQ ID NO:7—10) with Dra III site 1.    5' (AG)$_{10}$CCAGGTG<u>CACGATGTG</u>ACATCCAGATGACC 3'
2.    5' (AG)$_{10}$CCTGGAT<u>CACGATGTG</u>ATATTGTGATGAC 3'
3.    5' (AG)$_{10}$CCAGATA<u>CACGATGTG</u>AAATTGTGTTGAC 3'
4.    5' (AG)$_{10}$TCTGGTG<u>CACGATGTG</u>ACATCGTGATGAC 3'

Kappa constant region primer (SEQ ID NO.11) anti-sense strand with Bsi WI site $C_k$    5 (AG)$_{10}$TGCAGCCAC<u>CGTACG</u>TTTGATTTCCA(G/C)CTT 3'

*Legend for Table IV: Synthetic oligonucleotide primers used for the PCR amplification of human immunoglobulin heavy and light chain variable regions.
Restriction sites for cloning are underlined in bold.

The first set of primers was designed for amplifying the heavy chain variable regions. It consists of one 3 primer that binds in the J region and five family-specific 5' primers that bind in the late leader and framework 1 region. A second set of primers was designed for amplifying the Kapp variable region. It consists of one 3' primer and four 5' primers that bind in the late leader and framework 1 regions. The PCR reactions were electrophoresed on agarose gels and correctly sized 350 base pair bands were excised. The DNA was electroeluted, cut with appropriate restriction enzymes and cloned into IDEC's NEOSPLA expression vector. (See FIG.

6) The NEOSPLA vector used for expression of human antibodies contains the following: CMV=cytomegalovirus promoter, BETA mouse beta globin major promoter, BGH=bovine growth hormone polyadenylation signal, SVO=SV40 origin of replication. N1=Neomycin phosphoamsferase exon 1, N2=Neomycin phosphotransferase exon 2. LIGHT=Human immunoglobulin kappa constant region. Heavy=Human immunoglobulin gamma 1 or gamma 4 PE constant region. L=leader. SV=SV40 polyadenylation region.

IDEC's NEOSPLA expression vectors were designed for large scale production of immunoglobulin genes (See, Reff et al, *Blood,* (1994), 83, 435–445, incorporated by reference in its entirety). Mouse/human chimerics, primate/human chimerics and human antibodies have been successfully expressed at high levels using these vectors. NEOSPLA contains a neomycin phosphotransferase gene for selection of CHO cells that have stably integrated the plasmid vector DNA. In addition, NEOSPLA contains a dihydrofolate reductase gene for amplification in methotrexate, a human constant light chain (either κ or λ) and a human constant heavy chain region (either γ1 or γ4(PE)). Gamma 4 (PE) is the human γ4 constant region with 2 mutations, a glutamic acid in the CH2 region which was introduced to eliminate residual FcR binding, and a proline substitution in the hinge region, intended to enhance the stability of the heavy chain disulfide bond interaction, Algre et al, *J. Immunol.,* 148, 3461–3468, (1992); Angal et al, *Mol. Immunol.,* 30, 105–108 (1993), both of which are incorporated by reference herein. Unique restriction sites have been incorporated into the vector in order to facilitate insertion of the desired and light variable regions. Reff et al., *Blood,* (1994), 83, 435–445.

The light chain of RF-2 has been cloned into NEOSPLA in duplicate and sequenced following the method of Sanger et al, Sanger et al., *Proc. Natl. Acad. Sci.* (1977), 74, 5463–5467. The kappa chain is a member of the kappa 2 subgroup. Similarly, the human heavy chain variable region of RF-2 has been isolated and cloned in front of the human γ1 constant domain.

The light chain coding genes of RF-1 and RF-2 were readily cloned, whereas cDNA for the genes encoding the heavy chains could not be generated using the common Tac reverse transcriptase. However, this problem was obviated by substituting a high temperature, 70° C., reverse transcriptase. Thereby, intact PCR products could be generated with primers primarily derived from $V_H2$ family genes.

Figure 10:
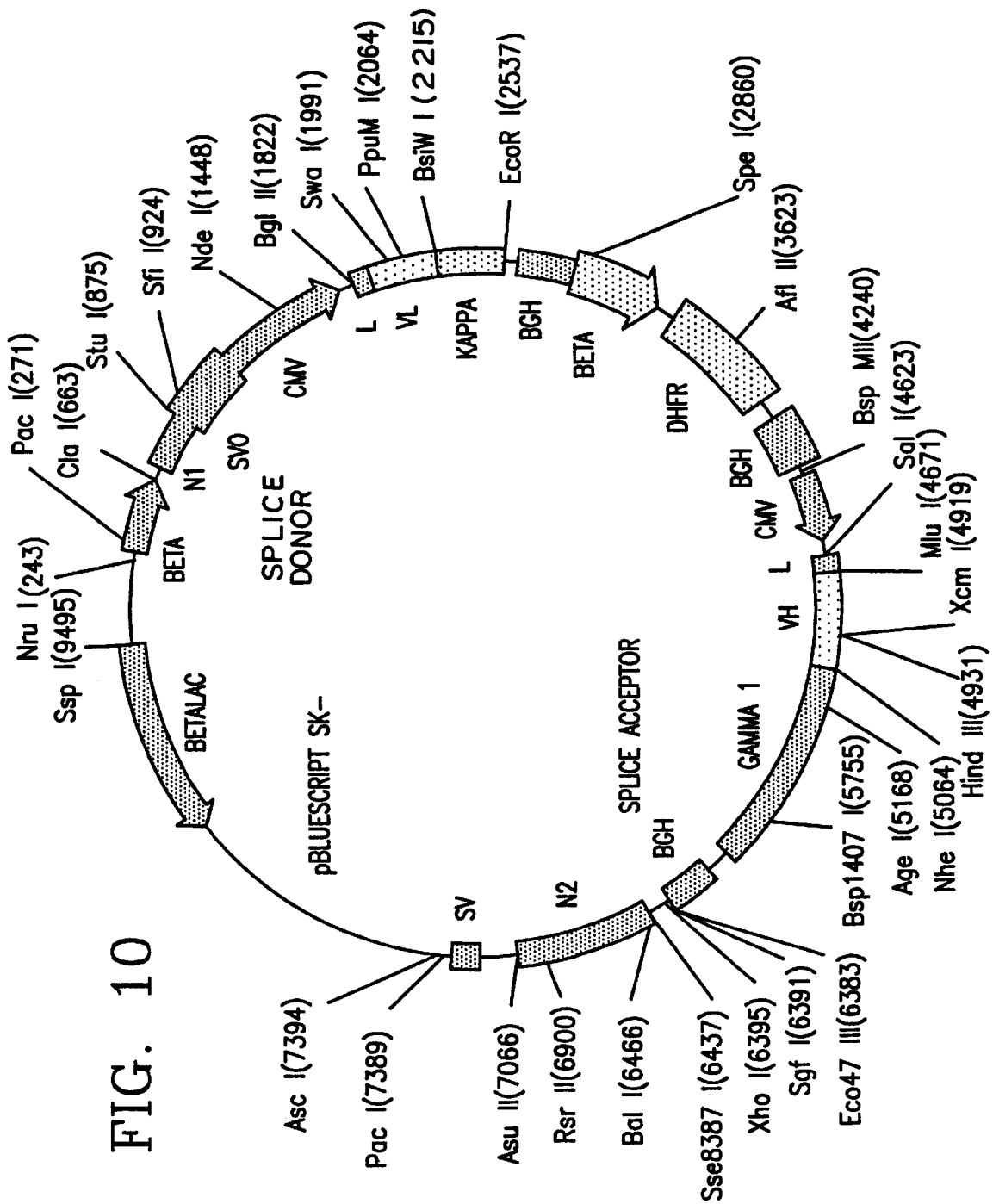
FIG. 10 depicts schematically the NEOSPLA vector, referred to as NSKE1 containing the RF-1 nucleic acid sequence and human gamma/constant domain set forth in FIGS. 9a–9c.

The amino acid sequence and the nucleic acid sequence for the RF-1 light and heavy variable domains may be found in FIGS. 7a and 7b, respectively. The amino acid sequence and the nucleic acid sequence for the light and heavy variable domains for RF-2 may be found in FIGS. 8a and 8B, respectively. FIGS. 9a–9c depict the nucleic acid and amino acid sequence of RF-1 as expressed in the subject NEOSPLA vector. FIGS. 9a and 9b depict the leader, variable light and heavy, and human constant domain sequences, i.e., the human kappa domain and the human gamma/constant domain. FIG. 9c shows the amino acid and nucleic acid sequence of the human gamma/constant domain. FIG. 10 depicts schematically an expression vector which provides for the expression of the sequences set forth in FIGS. 9a–9c and thereby recombinant RF-1 in CHO cells.

Figure 12:
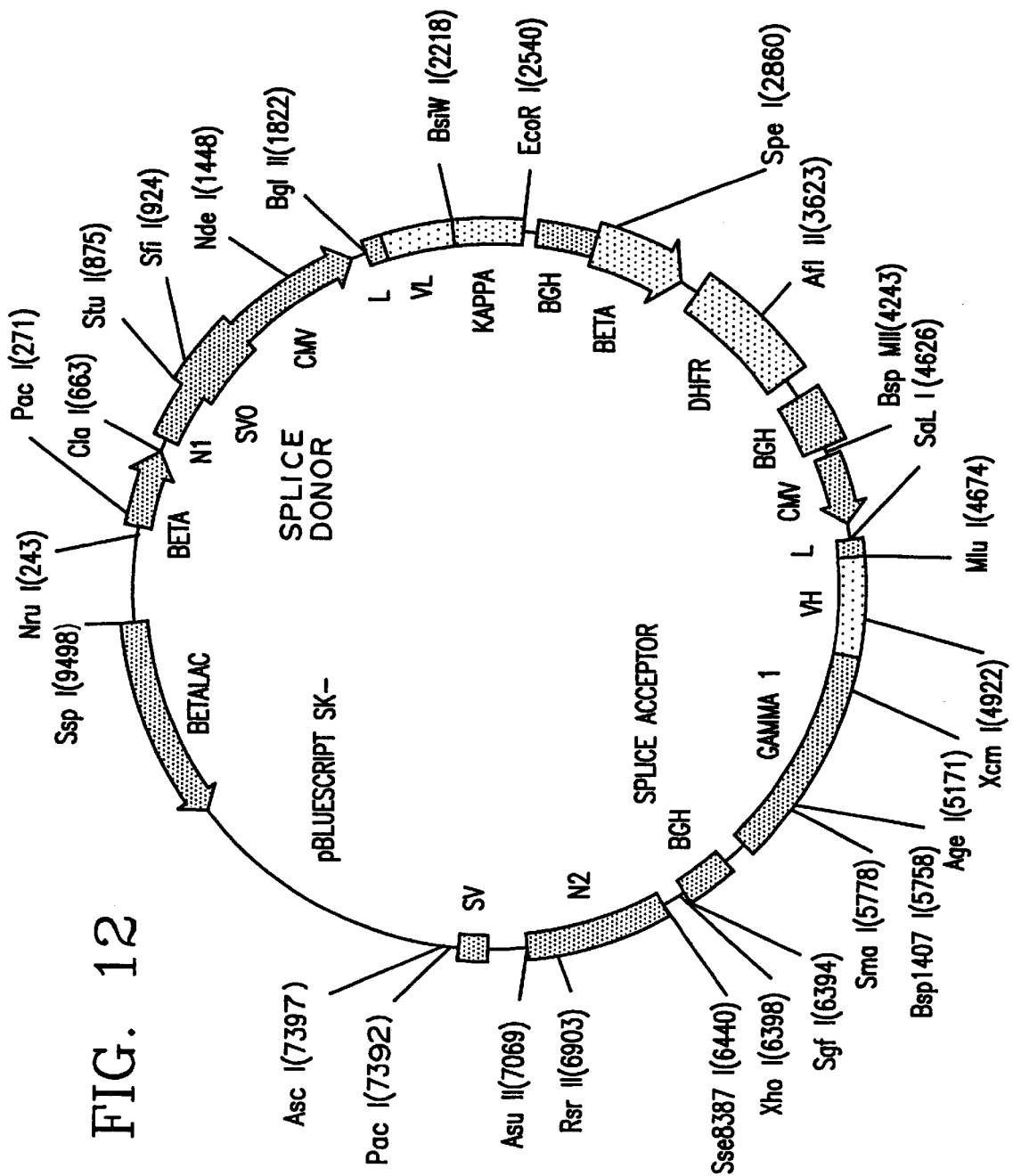
FIG. 12 depicts schematically the NEOSPLA expression vector, referred to as NSKG1 containing the RF-2 nucleic acid sequences and human gamma/constant domain sequences set forth in FIGS. 11a–11c.

FIGS. 11a–11a similarly depict the amino acid and nucleic acid sequences of the leader sequence, RF-1 variable light, human kappa constant region, RF-2 variable heavy, and human gamma/constant domain. FIG. 12 depicts schematically an expression vector which provides for the expression of recombinant RF-2 in CHO cells.

EXAMPLE 7

Development of a protocol for cloning of EBV transformed cells

Antibody production from EBV transformed cells continuously decrease, and ultimately ceases. Kozbor et al., *J. Immunol.* (1981), 127, 1275–1280. To immortalize the antibody production, it is therefore essential to extract the immunoglobulin coding genes from the cells before this event and transfer those into an appropriate expression system. In order to isolate the genes coding for the antigen binding variable domains of antibodies produced by EBV transformed cells, it is essential to ensure that the cell material is monoclonal, EBV transformed cells are, however, very difficult to clone whether by limiting dilution or in semisolid agar. Isoelectric focusing gel electrophoresis of protein A purified preparations of our two anti-F protein antibodies, RF-1 and RF-2, showed at least two populations of antibodies in the RF-2 preparation and the possibility of oligoclonality in the RF-1 preparation.

By using the mouse thyoma line EL-4 B5 Zhang et al, *J. Immunol.,* (1990), 144, 2955–2960, as feeder layer, cells were expanded from a single cell through limiting dilution. The human thyoma cell line EL-4 B5 expresses gp39 in a membrane receptor way that induces B cells to grow. $5 \times 10^4$ EL-4 B5 cells/well were plated out in a microliter plate, and cells from the cultures were plated out on the EL-4 B5 layer at various concentrations, from 0.38 cells/well and up. The number of wells with growth for each of the concentration plated were counted after an appropriate amount of time.

The supernatant was tested for presence of human IgG and for antigen-specific IgG. With this protocol we have isolated and cloned the cells that produce RF-1 (see Table V) and RF-2 (see Table VI), respectively, from the original oligoclonal preparations. The non-specific antibodies found in the cloning were only analyzed with respect to isotype, and were found to be the same as the specific antibodies, IgG1k. Based on the yield of F-protein specific clones from freezes made at various time points during the cultivation of RF-1, as well as the amount of IgG that was produced, it was estimated that the specific antibody made up approximately 1/20 of the total antibody amount shortly after the start of the culture and disappeared after approximately 8 months in culture. RF-2 made up a much higher part of the total IgG, no less than 10% at any given time. Antibody from the oligoclonal preparations was used to generate the in vitro neutralization data, resulting in an overestimation of the ED50 titers. Our affmity studies with plasmon resonance, however, were not dependent on using pure antibodies. The affinity studies using titration micro calorimetry was done with cloned material.

TABLE V*

| # cells/well | # wells | # anti-F wells (%) | # wells with growth (%) |
| --- | --- | --- | --- |
| 30 | 48 | 48(100) | 48(100) |
| 10 | 48 | 48(100) | 48(100) |
| 3.3 | 96 | 27(28) | 68(71) |

TABLE V*-continued

| # cells/well | # wells | # anti-F wells (%) | # wells with growth (%) |
|---|---|---|---|
| 1.1 | 192 | 17(9) | 112(58) |
| 0.38 | 384 | 18(5) | 116(30) |

*Legend for Table V: Cloning of RF-1 by limiting dilution. EL4-B5 cells were plated out at 5 × 1O4 cells/well in a flat bottomed 96 well plate. Approximately 24 hours later, RF-1 cells in exponential growth were plated out on the feeder layer at the described concentrations. After 2–3 weeks, the wells were scored for growth and for presence of anti-F activity.

TABLE VI*

| # cells/well | # wells | # anti-F wells (%) | # wells with growth (%) |
|---|---|---|---|
| 30 | 40 | 40(100) | 15(37.5) |
| 10 | 120 | 120(100) | 22(18) |
| 3.3 | 120 | 102(85) | 9(7.5) |
| 1.1 | 120 | 50(41.6) | 1(0.83) |
| .33 | 180 | 30(16.7) | 5(2.8) |

*Legend for Table XIV: Cloning of RF-2 by limiting dilutio/n. Done as in Table VIII.

Figure 6:
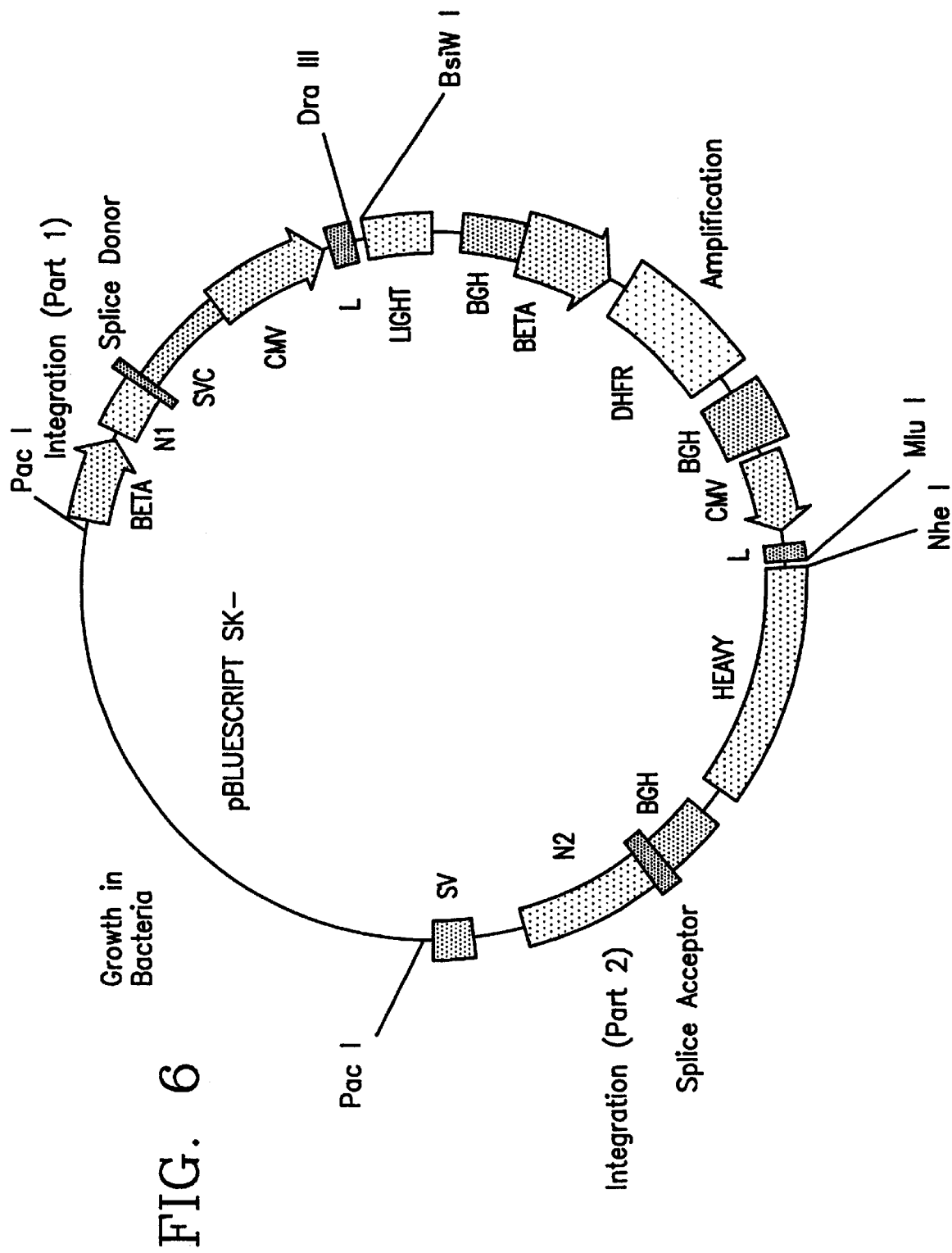
FIG. 6 depicts NEOSPLA vector used for expression of human antibodies. CMV=cytomegalovirus promoter. BETA=mouse beta globin major promoter. BGH=bovine growth hormone polyadenylation signal, SVO=SV40 origin of replication. N1=Neomycin phosphotransferase exon 1. N2=Neomycin phosphotransferase exon 2. LIGHT=Human immunoglobulin kappa constant region. Heavy=Human immunoglobulin gamma 1 or gamma 4 PE constant region. L=leader. SV=SV40 polyadenylation region.

In order to confirm the clinical applicability of the two human monoclonal antibodies with in vitro virus neutralizing activity, these antibodies are further characterized with respect to their efficacy in clearing RSV infection in two different animal models. These preclinical performance evaluations are effected with material produced by CHO cells transfected with the cloned genes coding for the antibodies inserted into a proprietary expression vector (see FIG. 6). Two antibody models, one with intact complement and Fc receptor binding domains, γ1, and one void of these domains, γ4 (PE mutant), Alegre et al., *J. Immunol.*, (1992), 148, 3461–3468; Angal et al., *Molecular Immunology,* (1993), 30, 105–108, will be tested. The rationale for testing γ4 version is based on two considerations: (i) Anti-F-protein Fabs have shown significant virus neutralizing effect in vitro Barbas et al., *Proc. Natl. Acad. Sci.* (1992), 89, 10164–10168, as well as in vivo, Crowe et al, *Proc. Natl. Acad. Sci.* (1994), 91, 1386–1390, albeit when administered directly into the lung, (ii) potentially avoiding lung damage caused by effector function activation in sensitive tissue already stressed by virus infection could be advantageous. A set of nonspecific control antibodies, one γ1 and one γ4 (PE), will be generated from an in-house non-specific hybridoma $IgG_1$ antibody.

The first animal model is a mouse model, Taylor et al., *J. Immunology* (1984), 52, 137–142; Walsh, E. E., *J. Infectious Diseases* (1994), 170, 345–350. This model is used to determine the effective dose, defined as the smallest dose resulting in a 2 log reduction in virus load in the lung tissue after 1 weeks incubation. This model is also used to determine which of the antibody models to proceed with. The second animal model is a primate model using the African green monkey, Kakuk et al, *J. Infectious Diseases* (1993), 167, 553–561. RSV causes lung damage in the African green monkey, and this model's main purpose is for evaluating the damage preventing properties of the antibodies. The number of tests with this model will be limited to test one antibody in 5 different doses. The antibody, the dose and the infusion date relative to infection date will be determined based on the findings with the mouse model. Lung section is examined for virus load in plaque assay and by light microscopy for detection of lesions caused by RSV.

It will be observed if any changes in the amino acid sequence have taken place during the process of stimulating and expanding the cells that produce the two antibodies. This is done by testing with a set of PCR primers based on the CDR3 regions of the heavy chains of RF-1 and RF-2 whether the sequences of the genes coding for RF-1 and RF-2 are present in the original frozen cell material from which the two cell lines were generated. The positive control is RF-1 and RF-2 spiked source cells. The analysis follows the principles established by Levy et al., 1989, Levy et al., *J. Exp. Med.* (1989), 169:2007 and Alegre et al., *J. Immunol.* (1992), 148, 3461–3468; Angal et al., *Molecular Immunology* (1993), 30, 105–108; Foote et al., *Nature* (1991), 352, 530–532; Rada et al., *Proc. Natl. Acad. Sci.* (1991), 88, 5508–5512; Kocks et al., *Rev. Immunol.* (1989), 7, 537–559; Wysocki et al., *Proc. Natl. Acad. Sci.* (1986), 83, 1847–1851; Kipps et al., *J. Exp. Med.* (1990), 171, 189–196; Ueki et al., *Exp. Med.* (1990), 171, 19–34.

EXAMPLE 8

Generate CHO cell lines that produce large amounts (>100 mg/liter) of RF-1 and RF-2 a. Transfect expression plasmids, isolate and expand G418 resistant CHO clones expressing the highest levels of RF-1 and RF-2

Once the RF-1 and RIF-2 variable region genes are cloned into NEOSPLA, Chinese hamster ovary (CHO) cells (DG44), Urlaub et al, *J. Somat. Cell Mol. Genet.,* (1986), 16, 555, are transformed with the plasmid DNA. CHO cells are grown in SSFM H minus hypoxanthine and thymidine (GlBCO). $4 \times 10^6$ cells are electroporated with 25 μg plasmid DNA using a BTX 600 electroporation device (BTX, San Diego, Calif.) in 0.4 ml disposable cuvettes. Prior to electroporation, the plasmid DNA will be restricted with Pac I which separates the genes expressed in mammalian cells from the portion of the plasmid used for growth in bacteria. Conditions for electroporation are 230 volts, 400 micro faradays, 13 ohms. Each electroporation is plated into a 96 well dish (about 40,000 cells/well). Dishes are fed with media containing G418 (Geneticin, GIBCO) at 400 μg/ml three days following electroporation, and thereafter, periodically, until colonies arise. Supernatant from colonies is assayed in ELISA for the presence of human IgG and for anti-F-protein activity.

b. Amplify the expression of antibody in methotrexate

The G418 resistant colonies producing the highest amount of immunoglobulin are then transferred to larger vessels and expanded. The expression of the highest secreting G418 clone is increased by gene amplification, by selection in 5 nM methotrexate (MTX) in 96 well dishes. The 5 nM colonies producing the highest amount of antibody are then expanded and then expression amplified again by selection in 50 nM MTX in 96 well dishes. Following this protocol, we have previously been able to derive CHO cells that secrete greater then 200 mgs/liter in 7 days in spinner culture (greater than 0.5 gram/liter in fermentors in 6 days). Human antibody is then purified from supernatant using protein A affinity chromatography.

c. Produce and purify antibody 100 mg of each antibody is generated. The selected antibody is produced in amounts determined from the mouse model studies. Spinner flasks with selected CHO transfectomas in CHO-S SFM II serum free medium (GIBCO Cat. No. 91-0456 DK) with 50 nM methotrexate are used to produce antibody in the required amounts. Supernatant are harvested and filtered through a set of filters to remove particular material, ending up with a 0.2 nm filter. The supernatant is run through a protein A column with a predetermined size based on the total amount of antibody. After washing, the antibody is eluted from the column with 0.1 M Glycine/HCI, pH 2.8, into a neutralization buffer, 1 M Tris./HCI, pH 7.4. The elution/neutralization buffer is exchanged extensively, $\geq 1000$ times, with sterile PBS by ultrafiltration through an Amicon Centriprep or Centricon 30 (Cat. no. 4306 and 4209). The concentration of antibody is adjusted to 2 mg/ml and sterilized by filtration through a 0.2 nm filter. The antibody is purified and stored on ice in 2 ml cryotubes until use in animals.

EXAMPLE 9

Characterize RF-1 and RF-2 in respect to performance in RSV animal models

The performance of RF-1 and RF-2 is determined using appropriate animal models. The evaluation is divided into two steps, first (a) a Balb/c model, Taylor et al., *J. Immunology* (1984), 52, 137–142; Crowe et al., *Proc. Natl. Acad. Sci.* (1994), 91, 1396–1390; Connors et al., *J. Virology* (1992), 66, 7444–7451, to determine the potency of the antibodies, as well as to determine what type of support (effector) functions are essential for the antibody to clear the virus load. From the data gained in the mouse model, one candidate is chosen for further studies in a primate model. The primate model is an African green monkey model, Kakuk et al., *J. Infectious Diseases* (1993), 167, 553–561. A primate model is especially suitable for confirming that the subject monoclonal antibodies can be used to prevent virus associated lung damage.

a. Test performance in mouse model

The rodent-model we have chosen is the Balb/c mouse. This model is well characterized, Crowe et al., *Proc. Natl. Acad. Sci.* (1994), 91, 1386–1390; Connors et al.,*J. Virology* (1992), 66, 7444–7451, for studies on passive therapy studies. Balb/c mice are highly permissive to growth of RSV in both upper and lower airways at all ages, Taylor et al., *J. Immunology* (1984), 52, 137–142. Animals are housed in groups of 5, fed standard mouse chow and water ad libitum and cared for according to the Rochester General Hospital vivarium guidelines. These guidelines are in compliance with the New York State Health Department, the Federal Animal Welfare Act and DHHS regulations. All procedures, including injections, virus infection, orbital bleeding and sacrifice by cervical dislocation, are performed under penthrane anesthesia in a vented hood.

i. Determine effective dose of antibody and compare performance of γ1 and γ4 (PE version) of RF-I and RF-2

Groups of 5 mice are infected by intranasal instillation of $10^6$ Long (subgroup A) or $10^5$ 18537 (subgroup B) plaque forming units (PFU) of RSV in a 100 μL volume on day 0. On day four, at peak virus titer, animals will be injected intraperitoneally with each of the four F-protein specific monoclonal antibody preparations or control antibody. The doses tested are initially centered around a reference dose calculated to provide a serum neutralization titer of approximately 1:300 or greater from in vitro studies. This titer has been associated with protective levels against challenge with RSV in small animals. Dose response is evaluated by treatment with 25, 5, 1, ⅕ and ¹⁄₂₅ of the reference dose. Experiments with higher or lower doses are performed if warranted. Control mice are injected with an equivalent dose of the isotype matched monoclonal antibodies, as described above. Twenty-four hours later; day 5 is the peak of virus shedding, the mice are sacrificed. Serum is obtained by intracardiac puncture and the nasal turbinates and lungs are removed, weighed and homogenized in 1 and 2 ml of NMM, respectively. Homogenates are titered for virus on HEp-2 cells, and virus titers expressed as $TCID_{50}$/gm tissue. The mean titers between groups are compared to the control group by the student t-test. Serum is obtained at the time of infection and at sacrifice for human monoclonal antibody quantification by enzyme immunoassay and neutralization assay. It is anticipated that the greatest reductions in virus titer will be in lung virus growth since IgG isotypes are not actively secreted (in contrast to IgA) in the upper respiratory tree. Should therapy on day 4 of infection prove ineffective at reducing lung virus, therapy on days 2 and/or 3 will be assessed.

The titer of each monoclonal antibody in stock solutions and in serum from injected animals is determined using an ELISA,as described supra. RSV fusion protein purified by affinity chromatography according to established methods Walsh et al. *J. Gen. Virol.* (1985), 66 409–415 is used in the solid phase. A separate assay for the RSV G protein will also be devised for evaluation of mouse IgG responses to experimental RSV infection. Rabbit antibody specific for human IgG and mouse IgG (available from Virion Systems, Inc., Bethesda, Md.) is used to detect human monoclonal antibody or mouse antibody in the ELISA.

The dose response effect of the monoclonal antibodies are determined for the antibodies as the lowest antibody titer which reduces virus titers more than 2 $\log_{10}$ or>99% reduction in virus titer. The degree of protection are correlated to the serum antibody levels achieved at the time of sacrifice. In addition, the potential synergistic effect of various combinations of human monoclonal antibodies is determined. The results of the initial in vitro studies outlined above will be used to guide the in vivo experiments. For instance, if RF-1 and RF-2 have distinct antigenic binding sites on the RSV F protein, combinations of the same isotype (γ1 or γ4) may provide for synergistic protection.

ii. Histological evaluation of lung tissue

The effect of passive therapy on lung inflammation is evaluated by standard histopathological and immunohistochemical techniques. Both peribronchiolar infiltrates and alveolar infiltrates have been described in the mouse following either primary or secondary infections, Conners et al, *J. Virology,* (1992), 66, 7444–7451. Experimental animals are treated with monoclonal antibody, as described above. Uninfected untreated control mice serve as comparisons for evaluating histological effects. On days 5 and 8 after infection, the lungs are removed and inflated with formalin under constant filling pressure (30 cm $H_2O$) for 30 minutes. After sectioning and staining with hematoxylin-eosin, the degree of inflammatory infiltrate (PMN and lymphocytic separately) in the peribronchiolar and alveolar areas is determined using a standardized scoring system. Since it is anticipated that the γ1 and γ4 monoclonal antibodies may fix and activate complement differentially, the lung sections are stained for mouse C3 deposition in areas of inflammation using a commercially available rabbit anti-mouse C3 antibody (Viron Systems, Inc. Bethesda, Md.) and peroxidase conjugated goat and-rabbit IgG.

In addition to evaluation of histological changes seen in fixed pulmonary tissues, pulmonary inflammation is assessed by evaluation of alveolar cytology. Groups of mice, treated as described above, are sacrificed and a bronchoalveolar lavage (BAL) performed by repeatedly infusing 3 ml PBS into the lower airway. Cell counts of the BAL will be performed, and the cell type identified by staining of cytocentrifuge preparations.

iii. Effect of antibody therapy on the natural immune response to infection

In the cotton rat and owl monkey models, passive therapy of RSV infection with polyclonal IgG preparations diminishes the subsequent natural antibody response to the virus, although animals are fully protected upon re challenge, Hemming et al., *J. Infectious Diseases* (1985), 152, 1083–1086; Prince et al., *Virus Research* (1985), 3, 193–206. In contrast, Graham found that treated mice had both blunted antibody responses and were susceptible to virus re challenge, Graham et al., *Ped. Research* (1993), 34, 167–172. To assess this possibility using human monoclonal antibodies, mice are infected with the Long strain of RSV and treated with a protective dose of antibody on day 4, as outlined above. Controls will include infected untreated animals, and uninfected treated animals. Mice are bled for antibody determination every other week for 8 weeks and then every 4 weeks for an additional 8 weeks. Both human monoclonal antibody and mouse antibody to the RSV F and G proteins are determined by ELISA. In addition, the neutralization titer of the serum determined at each time point. The contributions to neutralization by the residual human monoclonal antibody and actively produced mouse antibody are inferred from the ELISA results and by the results of neutralizing activity of the uninfected antibody treated controls. When human monoclonal antibody is undetectable by ELISA, animals are rechallenged with the same strain of RSV. After 4 days, the animals are sacrificed and the lungs and nasal tissues titered for virus and compared to control groups.

In order to assess the impact of monoclonal antibody therapy on cytotoxic T-cells (CTL) induction, similar experiments are carried, but six weeks after infection, mice are sacrificed and spleen cell cultures stimulated with live RSV for 5 days, Walsh, E. E., *J. Infectious Diseases* (1994), 170, 345–350. CTL activity is assessed by standard Chromium 51 release assay using persistently infected Balb/c fibroblast cell line (BCH4 cells) and compared to an uninfected Balb/c fibroblast line.

Based primarily on the effective dose studies of passive therapy of established RSV infections, it is then determined which antibody, RF-1 or RF-2, is the most efficacious for preventing or treating RSV infection. The choice between the γ1 or γ4 (PE) versions takes the lung histology studies into account, in particular whether recruitment of complement appear to be significantly enhanced with the Clq binding antibody. Massive activation of complement could potentially have adverse effects, although enhanced vascularization that follows might increase the virus-antibody confrontation.

c. Test performance in monkey model

The decisive test for the selected antibody is in a primate model. We have chosen the African green monkey (Cercopithecus aethiops) because it is highly permissive for RSV, and infection leads to enhanced lung pathology and detectable lesions, Kakuk et al., *J. Infectious Diseases* (1993), 167, 553–561. African green monkeys are also readily available and not endangered. This monkey weighs between 5 and 10 kgs. The highest expected maximal dose of antibody is 20 mgs/kg. Three animals of each 10 kgs with 20 mgs/kg equals 600 mgs of antibody. Some wild African green monkeys are naturally immune to RSV, and a requirement for entering monkeys into our study is that they are serum negative to RSV.

Based on the baseline established in the mouse model, effective dose/kg and infection time prior to therapy, a limited series of tests are performed in order to establish effective dose for virus reduction, as well as to confirm whether this correlates with prevention of lung pathology, in particular parenchymal inflammatory involvement. Only one virus strain, Long (subtype A) is tested. Initially 25, 5, 1, and 1/25 times the reference dose is tested. Two control groups, one that receive virus but no antibody, and another that receives virus and maximal dose of the isotype matched control antibody, are analyzed. Essentially, the experiments are effected as described above. Monkeys in groups of 3 are also infected by intranasal instillation with $10^6$ PFU of virus. Six to seven days after infection with virus the monkeys are sacrificed and lung and pharynx samples are taken for viral assays as described above and for histology.

Histology are performed essentially, as described above. Briefly, the lungs are perfused with 10% neutral buffered formalin under constant filing pressure. The lungs will remain in formalin for at least one week. After sectioning and staining with hematoxylin-eosin, the slides are evaluated histopathologically according to Kakuk et al., *J. Infectious Diseases* (1993), 167, 553–561. Serum samples are also be taken in order to determine the titer of human are antibody to RSV in ELISA and in Infection Neutralization assays.

EXAMPLE 10

1. Confirm tissue specificity by in vitro test on human tissue sections.

The antibody is then further tested for potential cross reactivity to normal tissues by immunohistology studies on different frozen normal tissue sections from two different individuals. Briefly, Cryostat microtome cuts of frozen tissues are subjected to 3 tests: Fixation analysis, a Nitration analysis and a specificity/distribution analysis Purified biotin labeled anti-RSV F-protein antibody in PBS with 1% BSA is added, and the slide is incubated for 30 min. in a humidified chamber at 200° C. The slide is then washed in PBS with I% BSA. The slide is subsequently incubated with Avidin-HRP in PBS with 1% BSA for 30 min. HRP is allowed to react with 3,3 diaminobenzidine-tetrahydrochloride, which forms an insoluble precipitate stain mediated by oxidation with HRP. This will identify any potential cross reactions of the subject human monoclonal antibodies. This test will be performed by Impath Laboratories, N.Y., N.Y., and is approved by the FDA for I.N.D. submissions for products destined for human therapy. This histology approach uses pre-existing tissue and is less costly than the alternative, targeting studies of RSV infected monkeys with radiolabeled antibody.

In the claims:

1. A human monoclonal antibody which specifically binds a RSV antigen and which possesses an affinity for said RSV antigen of $\leq 2\times 10^{-9}$ to $10^{-10}$ molar.

2. A pharmaceutical composition containing a human monoclonal antibody according to claim 1, and a pharmaceutically acceptable carrier.

3. The composition of claim 2, wherein said composition is suitable for administration by injection or via aerosol.

4. The composition of claim 2, wherein said carrier is buffered saline or bovine serum albumin.

5. The composition of claim 2, wherein said composition contains an amount of said antibody that provides for an effective dosage of 50 to 20,000 μg/kg upon administration.

6. The composition of claim 2, wherein said antibody is of the IgG isotype.

7. A method for producing human antibodies specific to the RSV fusion (F) protein which comprises:
   (i) priming human splenocytes in vitro in the presence of IL-2;
   (ii) transferring said primed human splenocytes into a SCID mouse;
   (iii) boosting said SCID mouse with RSV F-protein; and
   (iv) isolating human B-cells from said SCID mouse which secrete human monoclonal antibodies specific for the RSV F-protein.

* * * * *

UNITED STATES PATENT AND TRADEMARK OFFICE
CERTIFICATE OF CORRECTION

| | | |
|---|---|---|
| PATENT NO. | : 6,413,771 B1 | Page 1 of 1 |
| APPLICATION NO. | : 09/335697 | |
| DATED | : July 2, 2002 | |
| INVENTOR(S) | : Peter Brams | |

It is certified that error appears in the above-identified patent and that said Letters Patent is hereby corrected as shown below:

<u>Title page,</u>
Item [75], Inventors, delete "Peter Brams, San Diego; Phillip R. Morrow, Carlsbad, both of CA (US)", and replace with the following -- Peter Brams, San Diego, CA (US) --.

Signed and Sealed this

Twenty-seventh Day of June, 2006

JON W. DUDAS
*Director of the United States Patent and Trademark Office*